US012606863B2

(12) United States Patent
Zhou et al.

(10) Patent No.: US 12,606,863 B2
(45) Date of Patent: Apr. 21, 2026

(54) BIOLUMINESCENT DETECTION OF DNA SYNTHESIS

(71) Applicant: Promega Corporation, Madison, WI (US)

(72) Inventors: Wenhui Zhou, Madison, WI (US); Hui Wang, Madison, WI (US); Min Zhou, Madison, WI (US); Natasha Karassina, Madison, WI (US); James Cali, Madison, WI (US); Jolanta Vidugiriene, Madison, WI (US)

(73) Assignee: Promega Corporation, Madison, WI (US)

( * ) Notice: Subject to any disclaimer, the term of this patent is extended or adjusted under 35 U.S.C. 154(b) by 991 days.

(21) Appl. No.: 17/744,255

(22) Filed: May 13, 2022

(65) Prior Publication Data

US 2022/0396830 A1 Dec. 15, 2022

Related U.S. Application Data

(60) Provisional application No. 63/188,259, filed on May 13, 2021.

(51) Int. Cl.

*C12Q 1/6841* (2018.01)
*C07H 19/06* (2006.01)
*C07H 19/14* (2006.01)
*C12N 9/14* (2006.01)

(52) U.S. Cl.

CPC .......... *C12Q 1/6841* (2013.01); *C07H 19/06* (2013.01); *C07H 19/14* (2013.01); *C12N 9/14* (2013.01); *C12Y 308/01005* (2013.01); *C07K 2319/00* (2013.01)

(58) Field of Classification Search

CPC .... C07H 21/04; C07H 19/173; C07H 19/073; C12Q 1/34; C12Q 1/6806
See application file for complete search history.

(56) References Cited

U.S. PATENT DOCUMENTS

| | | | |
|---|---|---|---|
| 5,703,224 A | 12/1997 | Ohgi et al. |
| 7,238,842 B2 | 7/2007 | Wood et al. |
| 7,425,436 B2 | 9/2008 | Darzins et al. |
| 7,429,472 B2 | 9/2008 | Darzins et al. |
| 7,867,726 B2 | 1/2011 | Wood et al. |

(Continued)

FOREIGN PATENT DOCUMENTS

| | | |
|---|---|---|
| JP | 2007126412 A | 5/2007 |
| WO | 9640711 A1 | 12/1996 |

(Continued)

OTHER PUBLICATIONS

Wang et al., Primer Extension Reaction Assays for Incorporation of Deoxynucleotide Analogue into DNA Chin J Chem vol. 33 pp. 192-198, DOI:10.1002/cjoc.201400731 (Year: 2015).*

(Continued)

*Primary Examiner* — Andrea Olson
(74) *Attorney, Agent, or Firm* — David W. Staple; Casimir Jones, S.C.

(57) ABSTRACT

Provided herein are reagents and methods for incorporating modified nucleotides into DNA and detecting DNA synthesis. In particular, haloalkyl-modified nucleobases are provided for incorporation into nucleic acids for detection by bioluminescent binding agents.

14 Claims, 8 Drawing Sheets

Specification includes a Sequence Listing.

(56) References Cited

U.S. PATENT DOCUMENTS

| | | | |
|---|---|---|---|
| 8,557,970 B2 | 10/2013 | Encell et al. | |
| 8,669,103 B2 | 3/2014 | Binkowski et al. | |
| 9,797,889 B2 | 10/2017 | Dixon et al. | |
| 10,024,862 B2 | 7/2018 | Hitko et al. | |
| 10,067,149 B2 | 9/2018 | Hitko et al. | |
| 2007/0037832 A1 | 2/2007 | Isobe et al. | |
| 2007/0232626 A1 | 10/2007 | Jacobson et al. | |
| 2008/0248511 A1 | 10/2008 | Daily et al. | |
| 2011/0201024 A1* | 8/2011 | Wood | C07D 495/04 435/174 |
| 2012/0107849 A1 | 5/2012 | Klaubert et al. | |
| 2013/0317207 A1 | 11/2013 | Kirkland et al. | |
| 2014/0099654 A1 | 4/2014 | Cali et al. | |
| 2017/0088830 A1* | 3/2017 | LaBaer | C12N 9/96 |
| 2017/0233789 A1 | 8/2017 | Shakhmin et al. | |
| 2018/0030059 A1 | 2/2018 | Hall et al. | |
| 2019/0008976 A1 | 1/2019 | Ziv et al. | |
| 2019/0064192 A1 | 2/2019 | Hitko et al. | |
| 2020/0270586 A1 | 8/2020 | Hall et al. | |
| 2021/0262941 A1 | 8/2021 | Kincaid et al. | |

FOREIGN PATENT DOCUMENTS

| | | |
|---|---|---|
| WO | 9849177 A1 | 11/1998 |
| WO | WO 2003/040100 | 5/2003 |
| WO | WO 2010/127368 | 11/2010 |
| WO | WO 2012/061529 | 5/2012 |
| WO | WO 2012/061530 | 5/2012 |
| WO | WO 2014/093677 | 6/2014 |
| WO | WO 2014/151736 | 9/2014 |
| WO | 2017058953 A1 | 4/2017 |
| WO | 2019178393 A1 | 9/2019 |
| WO | WO 2019/241438 | 12/2019 |
| WO | 2020210658 A1 | 10/2020 |
| WO | 2021031109 A1 | 2/2021 |
| WO | WO 2021/108765 | 6/2021 |

OTHER PUBLICATIONS

International Search Report and Written Opinion for PCT/US2022/029245. Mailed Sep. 23, 2022. 16 pages.

Feng et al., Improved split fluorescent proteins for endogenous protein labeling. Nat Commun. Aug. 29, 2017;8(1):370.

Foglieni et al., Split GFP technologies to structurally characterize and quantify functional biomolecular interactions of FTD-related proteins. Sci Rep. Oct. 25, 2017;7(1):14013.

Koraichi et al., High-content tripartite split-GFP cell-based assays to screen for modulators of small GTPase activation. J Cell Sci. Jan. 8, 2018;131(1):jcs210419.

PGM Wuts and TW Greene, Protective Groups in Organic Synthesis (5th ed.), John Wiley & Sons, NY. 2014. TOC only. 9 pages.

Pubchem SID349939874. Available Date: Dec. 18, 2017. Retrieved from the internet. Feb. 17, 2023. Https://pubchem.ncbi.nlm.nih.gov/substance/349939874. 5 pages.

Koudelakova T., et al., "Substrate Specificity of Haloalkane Dehalogenases", Biochemical Journal, vol. 435, No. 2, Apr. 15, 2011, pp. 345-354, XP055249571, GB, ISSN: 0264-6021, DOI: 10.1042/BJ20101405, the whole document, 19 pages.

Los G.V., et al., "HaloTag: A Novel Protein Labeling Technology for Cell Imaging and Protein Analysis," ACS Chemical Biology, vol. 3, No. 6, pp. 373-382, Jun. 1, 2008, DOI:10.1021/cb800025k, ISSN 1554-8929, XP055027634.

Ogilvie K.K., et al., "Fluoride lon Catalyzed Alkylation of Purines, Pyrimidines, Nucleosides and Nucleotides Using Alky Halides", Nucleic Acids Research, Apr. 4, 1979, XP093261284, pp. 1695-1708, p. 1698, compounds 2d and 2f.

Schmid M., et al., "Synthesis and Evaluation of a Radiometal-labeled Macrocyclic Chelator-derivatised Thymidine Analog", Nuclear Medicine and Biology, Elsevier, NY, US, vol. 33, No. 3, Apr. 1, 2006, pp. 359-366, XP025103493, ISSN: 0969-8051, DOI: 10.1016/J.NUCMEDBIO.2005.12.010, p. 362, compound 2.

Supplementary European Search Report for European Application No. 22808429.9, mailed Apr. 24, 2025, 16 Pages.

* cited by examiner

#7931

#7960

SEQUENCE LISTING

<160> NUMBER OF SEQ ID NOS: 19

<210> SEQ ID NO 1
<211> LENGTH: 170
<212> TYPE: PRT
<213> ORGANISM: Oplophorus gracilirostris

<400> SEQUENCE: 1

Met Phe Thr Leu Ala Asp Phe Val Gly Asp Trp Gln Gln Thr Ala Gly
1 5 10 15

Tyr Asn Gln Asp Gln Val Leu Glu Gln Gly Gly Leu Ser Ser Leu Phe
20 25 30

Gln Ala Leu Gly Val Ser Val Thr Pro Ile Gln Lys Val Val Leu Ser
35 40 45

Gly Glu Asn Gly Leu Lys Ala Asp Ile His Val Ile Ile Pro Tyr Glu
50 55 60

Gly Leu Ser Gly Phe Gln Met Gly Leu Ile Glu Met Ile Phe Lys Val
65 70 75 80

Val Tyr Pro Val Asp Asp His His Phe Lys Ile Ile Leu His Tyr Gly
85 90 95

Thr Leu Val Ile Asp Gly Val Thr Pro Asn Met Ile Asp Tyr Phe Gly
100 105 110

Arg Pro Tyr Pro Gly Ile Ala Val Phe Asp Gly Lys Gln Ile Thr Val
115 120 125

Thr Gly Thr Leu Trp Asn Gly Asn Lys Ile Tyr Asp Glu Arg Leu Ile
130 135 140

Asn Pro Asp Gly Ser Leu Leu Phe Arg Val Thr Ile Asn Gly Val Thr
145 150 155 160

Gly Trp Arg Leu Cys Glu Asn Ile Leu Ala
165 170

<210> SEQ ID NO 2
<211> LENGTH: 147
<212> TYPE: PRT
<213> ORGANISM: Oplophorus gracilirostris

<400> SEQUENCE: 2

Met Phe Thr Leu Ala Asp Phe Val Gly Asp Trp Gln Gln Thr Ala Gly

```
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Ile Pro Tyr Glu
    50                  55                  60

Gly Leu Ser Gly Phe Gln Met Gly Leu Ile Glu Met Ile Phe Lys Val
65                  70                  75                  80

Val Tyr Pro Val Asp Asp His His Phe Lys Ile Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
        115                 120                 125

Thr Gly Thr Leu Trp Asn Gly Asn Lys Ile Tyr Asp Glu Arg Leu Ile
    130                 135                 140

Asn Pro Asp
145


<210> SEQ ID NO 3
<211> LENGTH: 10
<212> TYPE: PRT
<213> ORGANISM: Oplophorus gracilirostris

<400> SEQUENCE: 3

Gly Ser Leu Leu Phe Arg Val Thr Ile Asn
1               5                   10


<210> SEQ ID NO 4
<211> LENGTH: 13
<212> TYPE: PRT
<213> ORGANISM: Oplophorus gracilirostris

<400> SEQUENCE: 4

Gly Val Thr Gly Trp Arg Leu Cys Glu Asn Ile Leu Ala
1               5                   10


<210> SEQ ID NO 5
<211> LENGTH: 171
<212> TYPE: PRT
<213> ORGANISM: Artificial sequence
<220> FEATURE:
<223> OTHER INFORMATION: Synthetic polypeptide

<400> SEQUENCE: 5

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95
```

-continued

```
Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170


<210> SEQ ID NO 6
<211> LENGTH: 148
<212> TYPE: PRT
<213> ORGANISM: Artificial sequence
<220> FEATURE:
<223> OTHER INFORMATION: Synthetic polypeptide

<400> SEQUENCE: 6

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp
145


<210> SEQ ID NO 7
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 7

Gly Ser Leu Leu Phe Arg Val Thr Ile Asn Val
1               5                   10


<210> SEQ ID NO 8
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 8

Gly Val Thr Gly Trp Arg Leu Cys Glu Arg Ile Leu Ala
```

1 5 10

<210> SEQ ID NO 9
<211> LENGTH: 158
<212> TYPE: PRT
<213> ORGANISM: Artificial sequence
<220> FEATURE:
<223> OTHER INFORMATION: Synthetic polypeptide

<400> SEQUENCE: 9

Met Val Phe Thr Leu Glu Asp Phe Val Gly Asp Trp Arg Gln Thr Ala
1 5 10 15

Gly Tyr Asn Leu Asp Gln Val Leu Glu Gln Gly Gly Val Ser Ser Leu
20 25 30

Phe Gln Asn Leu Gly Val Ser Val Thr Pro Ile Gln Arg Ile Val Leu
35 40 45

Ser Gly Glu Asn Gly Leu Lys Ile Asp Ile His Val Ile Ile Pro Tyr
50 55 60

Glu Gly Leu Ser Gly Asp Gln Met Gly Gln Ile Glu Lys Ile Phe Lys
65 70 75 80

Val Val Tyr Pro Val Asp Asp His His Phe Lys Val Ile Leu His Tyr
85 90 95

Gly Thr Leu Val Ile Asp Gly Val Thr Pro Asn Met Ile Asp Tyr Phe
100 105 110

Gly Arg Pro Tyr Glu Gly Ile Ala Val Phe Asp Gly Lys Lys Ile Thr
115 120 125

Val Thr Gly Thr Leu Trp Asn Gly Asn Lys Ile Ile Asp Glu Arg Leu
130 135 140

Ile Asn Pro Asp Gly Ser Leu Leu Phe Arg Val Thr Ile Asn
145 150 155

<210> SEQ ID NO 10
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 10

Val Thr Gly Tyr Arg Leu Phe Glu Glu Ile Leu
1 5 10

<210> SEQ ID NO 11
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 11

Val Ser Gly Trp Arg Leu Phe Lys Lys Ile Ser
1 5 10

<210> SEQ ID NO 12
<211> LENGTH: 155
<212> TYPE: PRT
<213> ORGANISM: Artificial sequence
<220> FEATURE:
<223> OTHER INFORMATION: Synthetic polypeptide

<400> SEQUENCE: 12

Met Lys His His His His His His Val Phe Thr Leu Asp Asp Phe Val

-continued 1 5 10 15

Gly Asp Trp Glu Gln Thr Ala Ala Tyr Asn Leu Asp Gln Val Leu Glu
20 25 30

Gln Gly Gly Val Ser Ser Leu Leu Gln Asn Leu Ala Val Ser Val Thr
35 40 45

Pro Ile Met Arg Ile Val Arg Ser Gly Glu Asn Ala Leu Lys Ile Asp
50 55 60

Ile His Val Ile Ile Pro Tyr Glu Gly Leu Ser Ala Asp Gln Met Ala
65 70 75 80

Gln Ile Glu Glu Val Phe Lys Val Val Tyr Pro Val Asp Asp His His
85 90 95

Phe Lys Val Ile Leu Pro Tyr Gly Thr Leu Val Ile Asp Gly Val Thr
100 105 110

Pro Asn Lys Leu Asn Tyr Phe Gly Arg Pro Tyr Glu Gly Ile Ala Val
115 120 125

Phe Asp Gly Lys Lys Ile Thr Thr Thr Gly Thr Leu Trp Asn Gly Asn
130 135 140

Lys Ile Ile Asp Glu Arg Leu Ile Thr Pro Asp
145 150 155

<210> SEQ ID NO 13
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 13

Gly Ser Met Leu Phe Arg Val Thr Ile Asn Ser
1 5 10

<210> SEQ ID NO 14
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 14

Gly Ser Met Leu Phe Arg Val Thr Ile Asn Ser Val Ser Gly Trp Arg
1 5 10 15

Leu Phe Lys Lys Ile Ser
20

<210> SEQ ID NO 15
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 15

Val Ser Gly Trp Arg Leu Phe Lys Lys Ile Ser
1 5 10

<210> SEQ ID NO 16
<211> LENGTH: 297
<212> TYPE: PRT
<213> ORGANISM: Artificial sequence
<220> FEATURE:
<223> OTHER INFORMATION: Synthetic polypeptide

<400> SEQUENCE: 16

Met Ala Glu Ile Gly Thr Gly Phe Pro Phe Asp Pro His Tyr Val Glu
1 5 10 15

Val Leu Gly Glu Arg Met His Tyr Val Asp Val Gly Pro Arg Asp Gly
20 25 30

Thr Pro Val Leu Phe Leu His Gly Asn Pro Thr Ser Ser Tyr Val Trp
35 40 45

Arg Asn Ile Ile Pro His Val Ala Pro Thr His Arg Cys Ile Ala Pro
50 55 60

Asp Leu Ile Gly Met Gly Lys Ser Asp Lys Pro Asp Leu Gly Tyr Phe
65 70 75 80

Phe Asp Asp His Val Arg Phe Met Asp Ala Phe Ile Glu Ala Leu Gly
85 90 95

Leu Glu Glu Val Val Leu Val Ile His Asp Trp Gly Ser Ala Leu Gly
100 105 110

Phe His Trp Ala Lys Arg Asn Pro Glu Arg Val Lys Gly Ile Ala Phe
115 120 125

Met Glu Phe Ile Arg Pro Ile Pro Thr Trp Asp Glu Trp Pro Glu Phe
130 135 140

Ala Arg Glu Thr Phe Gln Ala Phe Arg Thr Thr Asp Val Gly Arg Lys
145 150 155 160

Leu Ile Ile Asp Gln Asn Val Phe Ile Glu Gly Thr Leu Pro Met Gly
165 170 175

Val Val Arg Pro Leu Thr Glu Val Glu Met Asp His Tyr Arg Glu Pro
180 185 190

Phe Leu Asn Pro Val Asp Arg Glu Pro Leu Trp Arg Phe Pro Asn Glu
195 200 205

Leu Pro Ile Ala Gly Glu Pro Ala Asn Ile Val Ala Leu Val Glu Glu
210 215 220

Tyr Met Asp Trp Leu His Gln Ser Pro Val Pro Lys Leu Leu Phe Trp
225 230 235 240

Gly Thr Pro Gly Val Leu Ile Pro Pro Ala Glu Ala Ala Arg Leu Ala
245 250 255

Lys Ser Leu Pro Asn Cys Lys Ala Val Asp Ile Gly Pro Gly Leu Asn
260 265 270

Leu Leu Gln Glu Asp Asn Pro Asp Leu Ile Gly Ser Glu Ile Ala Arg
275 280 285

Trp Leu Ser Thr Leu Glu Ile Ser Gly
290 295

<210> SEQ ID NO 17
<211> LENGTH: 170
<212> TYPE: PRT
<213> ORGANISM: Artificial sequence
<220> FEATURE:
<223> OTHER INFORMATION: Synthetic polypeptide

<400> SEQUENCE: 17

Met Val Phe Thr Leu Asp Asp Phe Val Gly Asp Trp Glu Gln Thr Ala
1 5 10 15

Ala Tyr Asn Leu Asp Gln Val Leu Glu Gln Gly Gly Val Ser Ser Leu
20 25 30

Leu Gln Asn Leu Ala Val Ser Val Thr Pro Ile Met Arg Ile Val Arg
35 40 45

Ser Gly Glu Asn Ala Leu Lys Ile Asp Ile His Val Ile Ile Pro Tyr

-continued

```
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser Val
145                 150                 155                 160

Thr Gly Tyr Arg Leu Phe Glu Glu Ile Leu
                165                 170


<210> SEQ ID NO 18
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 18

Gly Ser Met Leu Phe Arg Val Thr Ile Asn Ser Val Thr Gly Tyr Arg
1               5                   10                  15

Leu Phe Glu Glu Ile Leu
            20


<210> SEQ ID NO 19
<211> LENGTH: 148
<212> TYPE: PRT
<213> ORGANISM: Artificial sequence
<220> FEATURE:
<223> OTHER INFORMATION: Synthetic polypeptide

<400> SEQUENCE: 19

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp
145
```

BIOLUMINESCENT DETECTION OF DNA SYNTHESIS

CROSS-REFERENCE TO RELATED APPLICATIONS

This application claims the benefit of U.S. Provisional Patent Application No. 63/188,259, filed on May 13, 2021, which is incorporated by reference herein.

FIELD

Provided herein are reagents and methods for incorporating modified nucleotides into DNA and detecting DNA synthesis. In particular, haloalkyl-modified nucleobases are provided for incorporation into nucleic acids for detection by bioluminescent binding agents.

BACKGROUND

Several methods and kits are available for measuring cell proliferation including measuring the changes in the number of live cells using various viability assays. However, the most direct and accurate method for measuring cell proliferation is by measuring the synthesis of new DNA. Initially, this was performed by incorporation of radioactive nucleosides (e.g., H-thymidine). However, to avoid radioactivity, other non-radioactive methods using modified nucleoside analogs, for example, bromo-deoxyuridine (BrdU) and 5-ethynyl-2'-deoxyuridine (Edu), have been developed. During cell replication, the deoxyuridine nucleoside analogs are incorporated into the replicating DNA in place of thymidine. Incorporation of BrdU is detected by anti-BrdU antibodies using standard ELISAs. Edu contains an alkyne group and is detected thru chemical reaction with azide containing fluorescent probes.

SUMMARY

Provided herein are reagents and methods for incorporating modified nucleotides into DNA and detecting DNA synthesis (and/or cell proliferation). In particular, haloalkyl-modified nucleobases are provided for incorporation into nucleic acids for detection by bioluminescent binding agents.

In some embodiments, provided herein are compounds of formula (I):

(I)

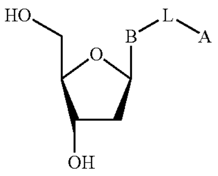

or a salt thereof, wherein: B is nucleobase or modified nucleobase, including but not limited to modified adenine, guanine, uracil, or cytosine; L is a linker; and A is a haloalkyl group. In some embodiments, a compound, or a salt thereof, comprises one of:

(ii)

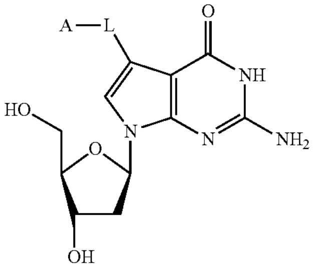

(III)

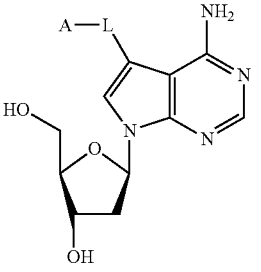

(IV)

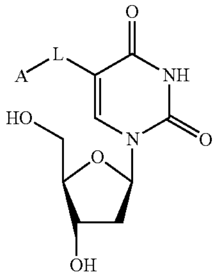

(V)

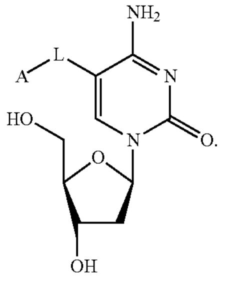

In some embodiments, L comprises one or more groups independently selected from alkyl, cyclic alkyl, alkylene, alkenylene, alkynylene, arylene, —O—, —NH—, and —C(O)—. In some embodiments, L comprises one or more groups selected from $-(CH_2)_m-$, —CH═CH—, —C≡C—, —C(O)NH—, —OC(O)NH—, $-CH_2CH_2O-$, and $-CH_2O-$, wherein m is 1-6. In some embodiments, L is selected from:

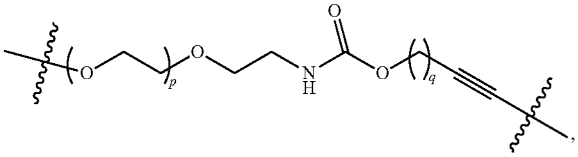
,
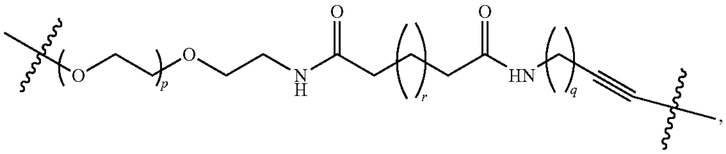
,
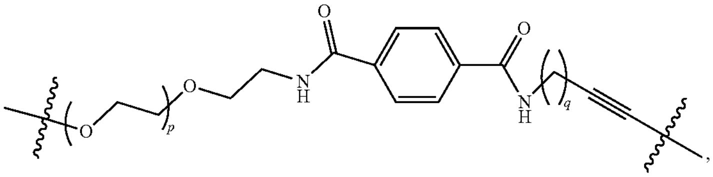
,
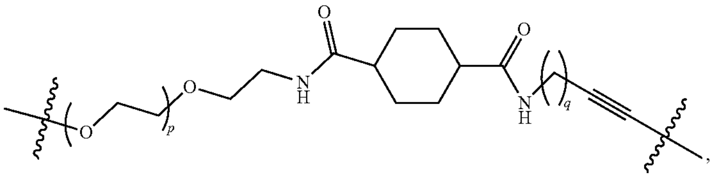
,
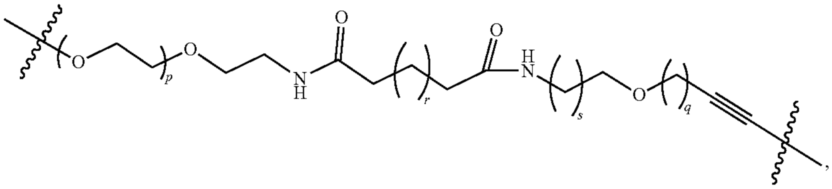
,
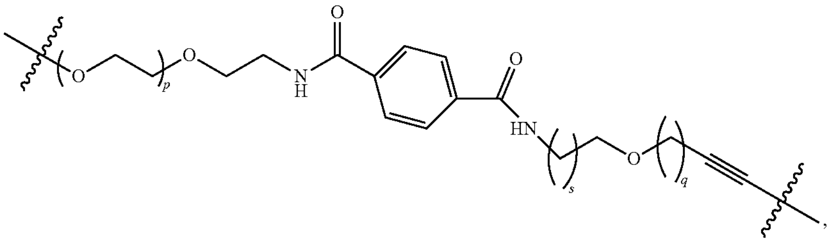
,
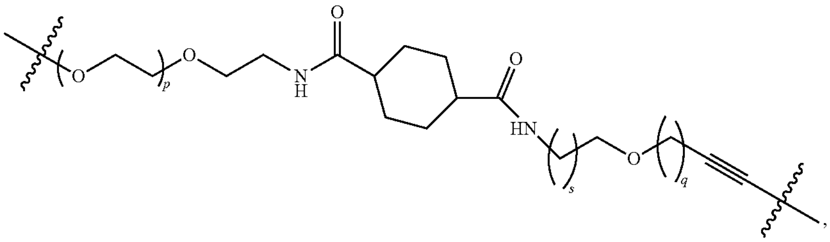
,
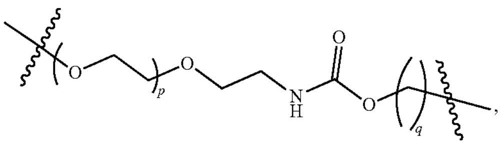
,
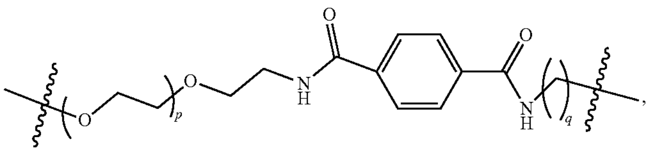
, -continued

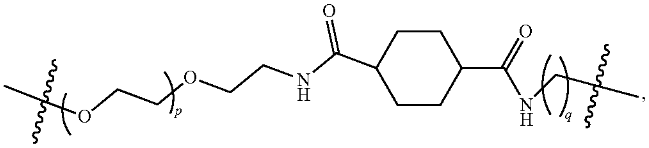,

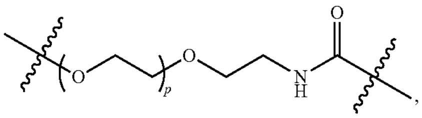,

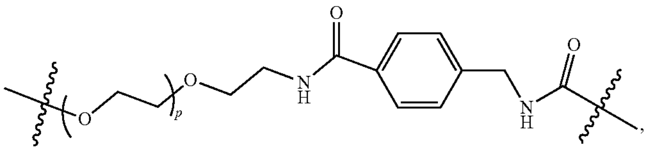,

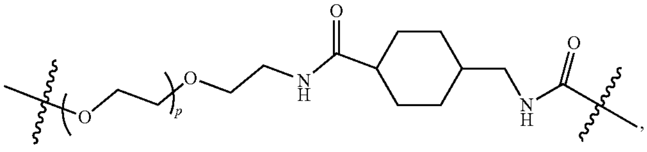,

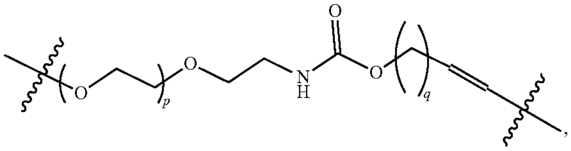,

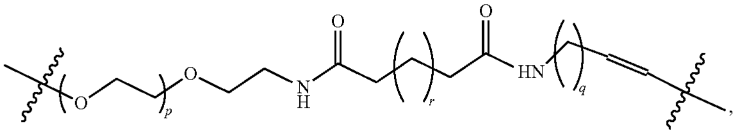,

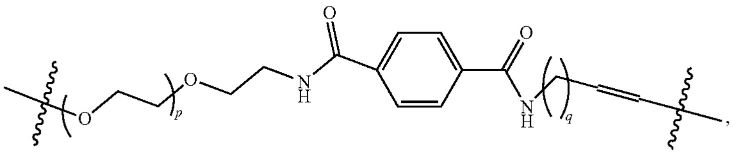,

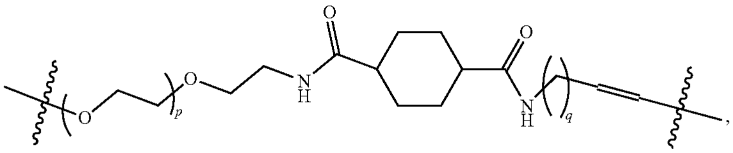, wherein p, q, r, and s are each independently 1-6. In some embodiments, L is C≡C-L', wherein L' is selected from alkyl, cyclic alkyl, alkylene, alkenylene, alkynylene, arylene, —O—, —NH—, —C(O)—, $-(CH_2)_m-$, —CH═CH—, —C≡C—, —C(O)NH—, —OC(O)NH—, $-CH_2CH_2O-$, and $-CH_2O-$, wherein m is 1-6. In some embodiments, A is a $C_2$-$C_{12}$ haloalkyl group. In some embodiments, A is $-(CH_2)_n$-X, wherein n is 4, 5, 6, 7, or 8, and X is halo. In some embodiments, X is Cl or Br. In some embodiments, n is 6. In some embodiments, X is Cl.

In some embodiments, a compound of formula (II) is selected from:

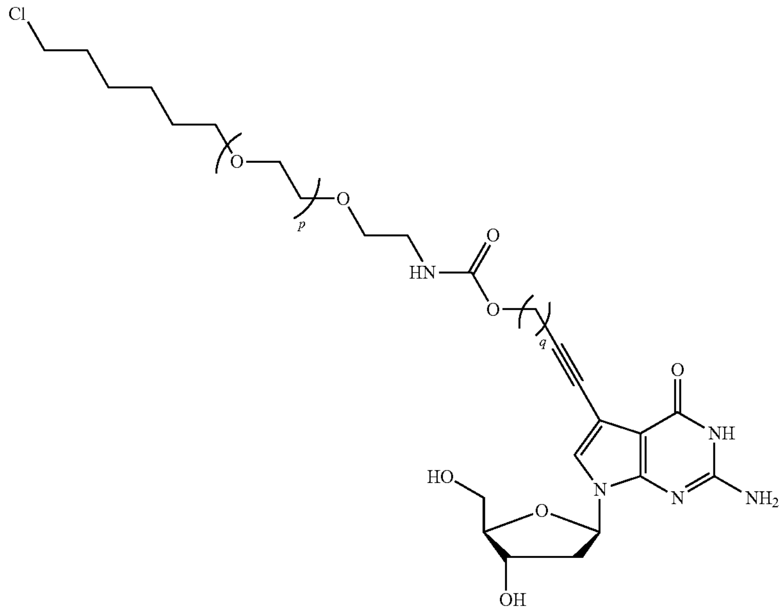
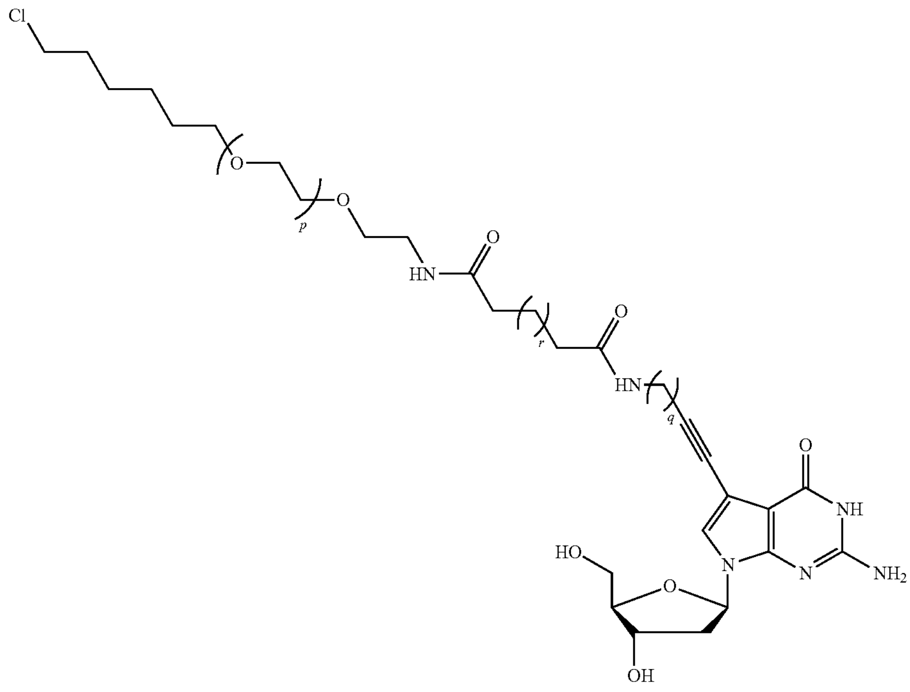

-continued
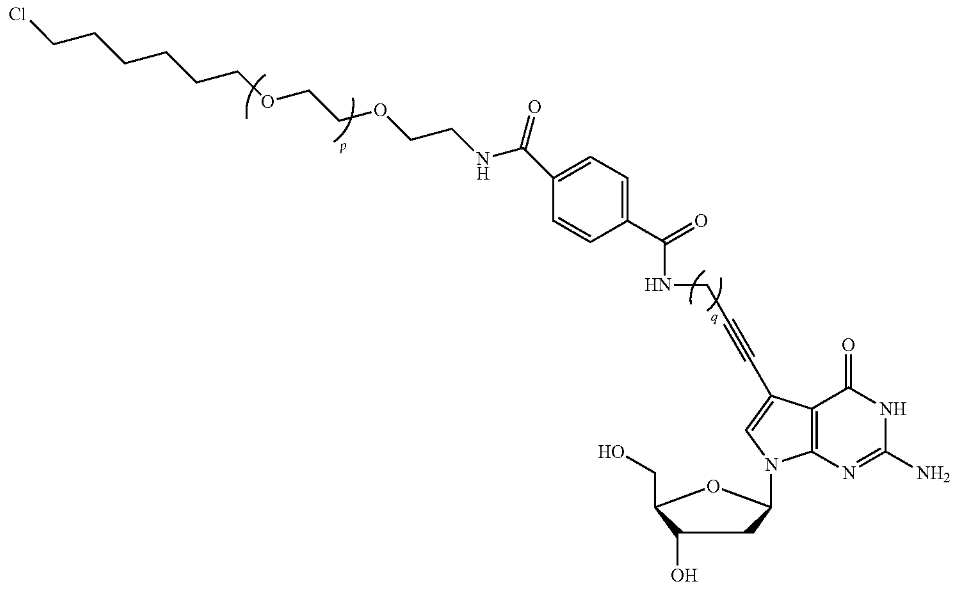
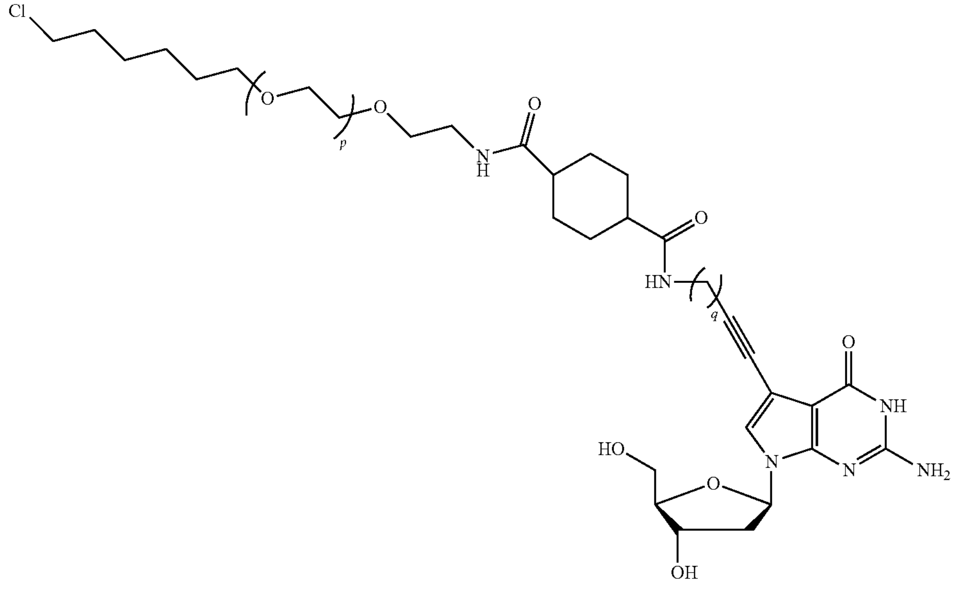

-continued
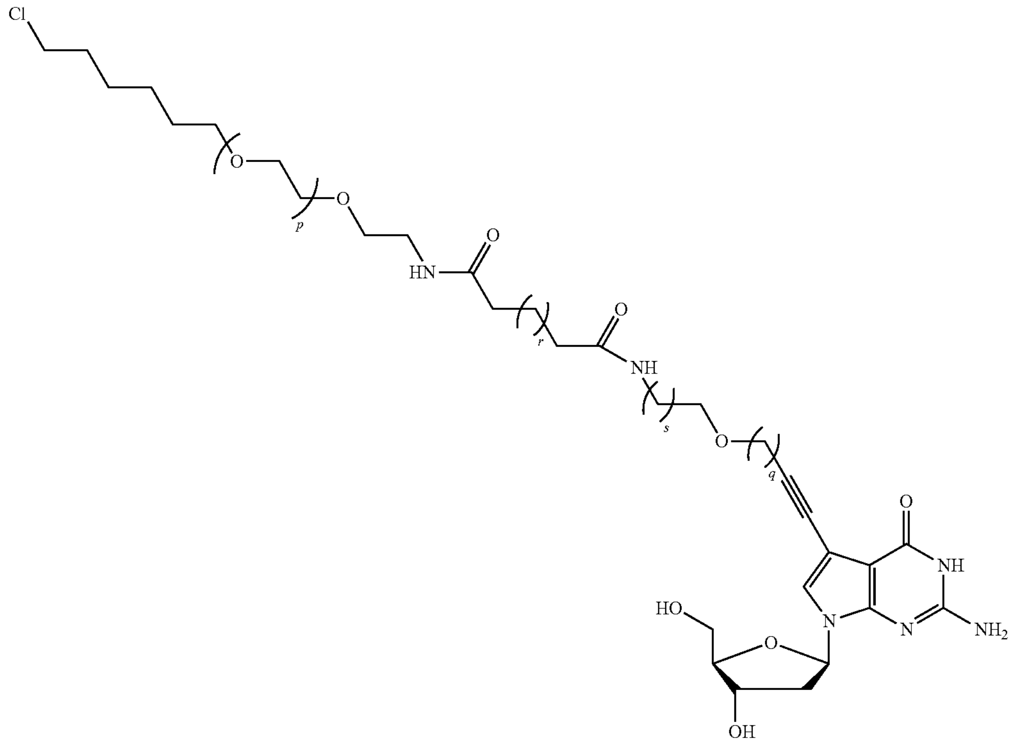
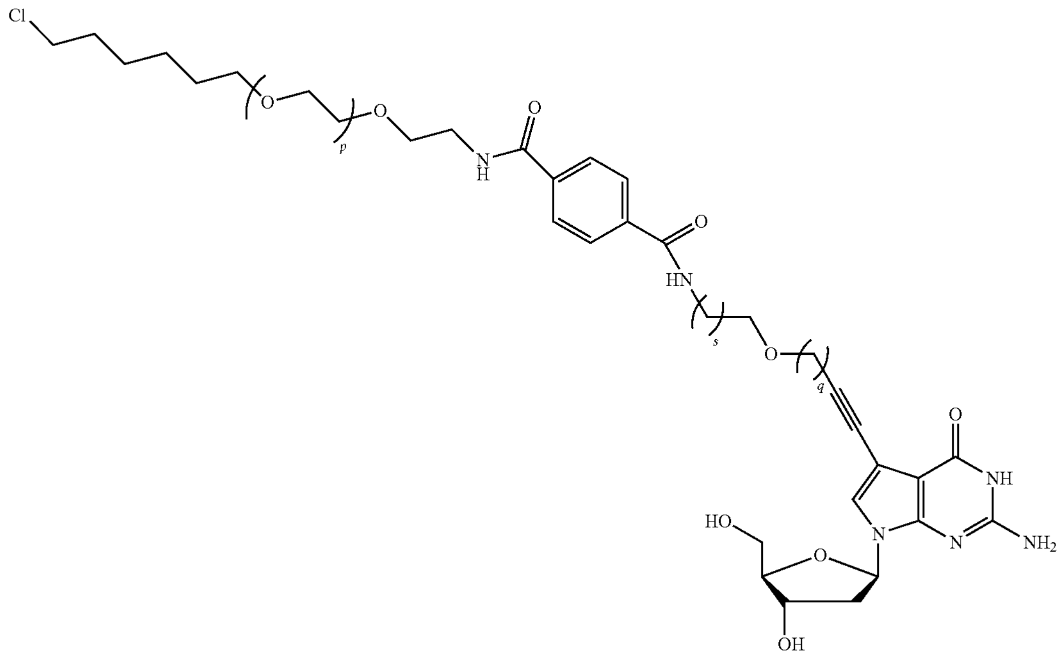

-continued
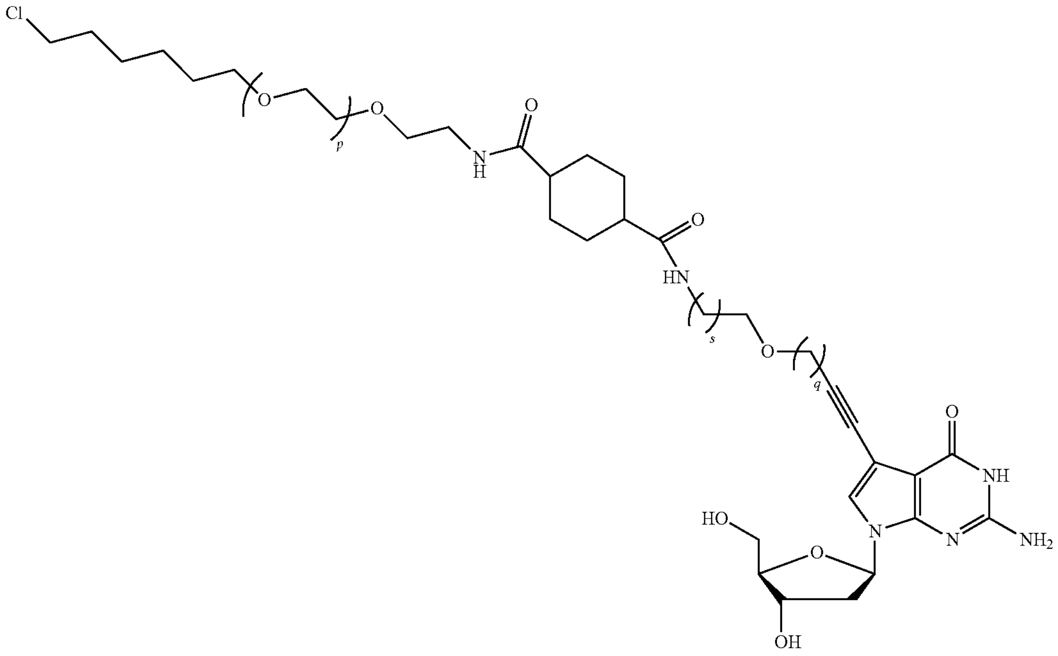
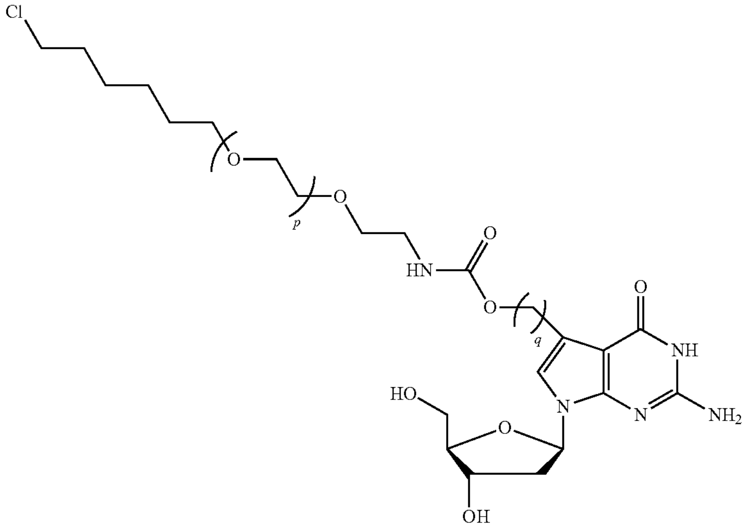

-continued
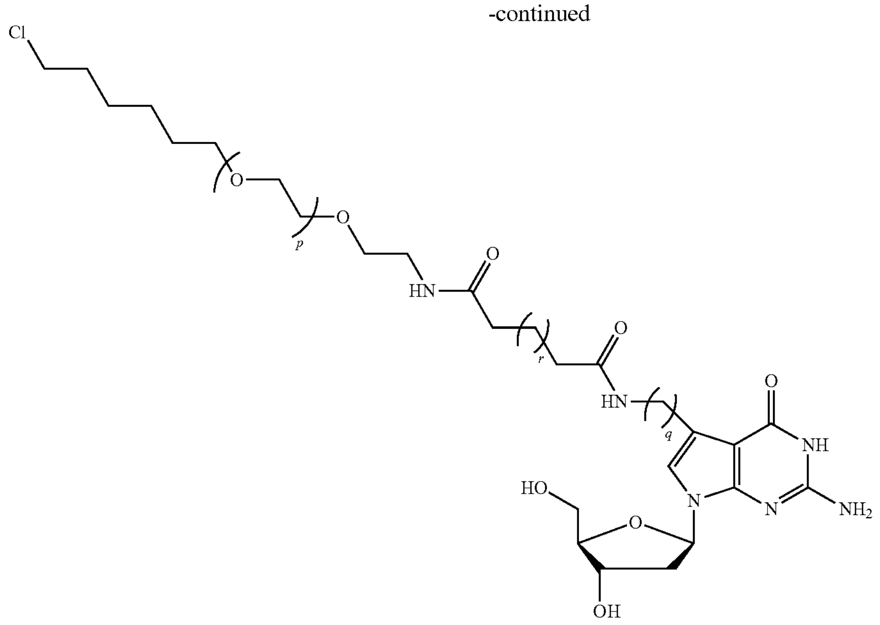
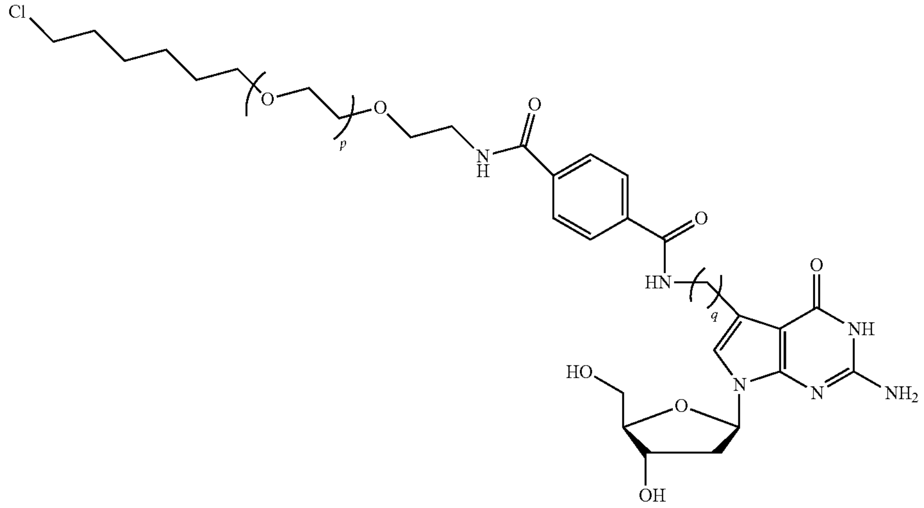
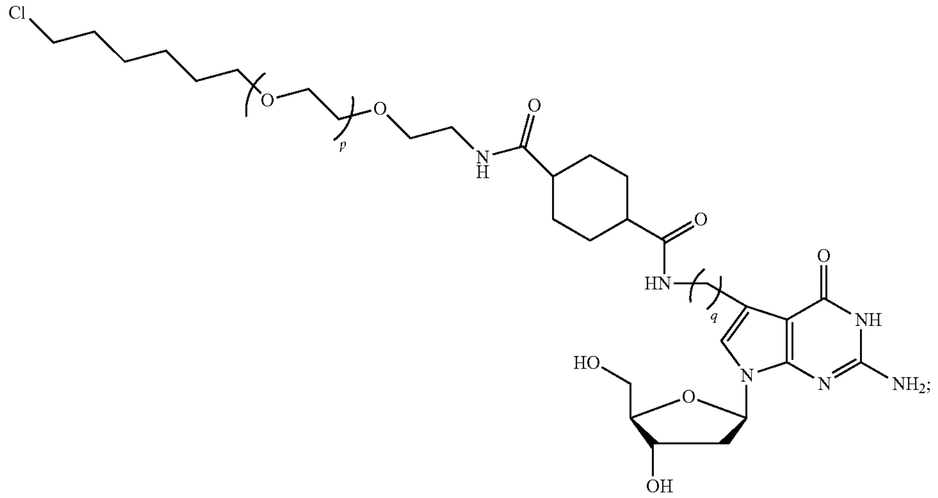

-continued
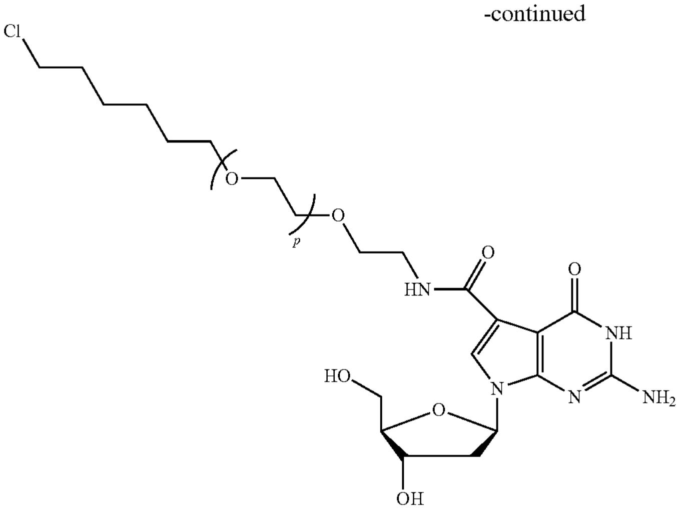
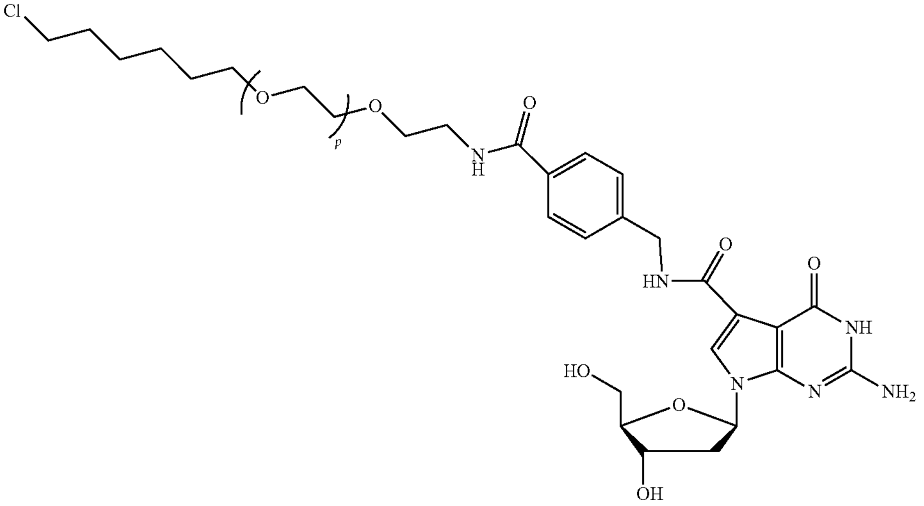
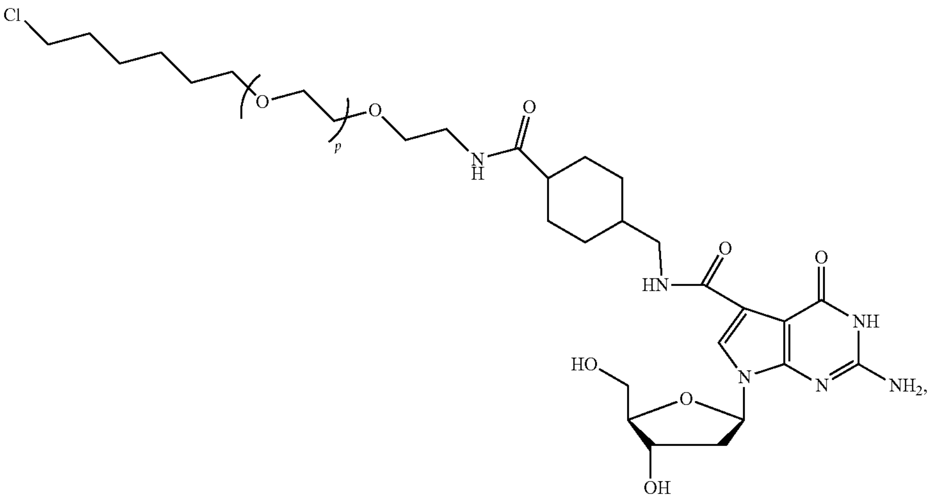
wherein p, q, r, and s are independently 1-6.

In some embodiments, a compound of formula (III) is selected from:
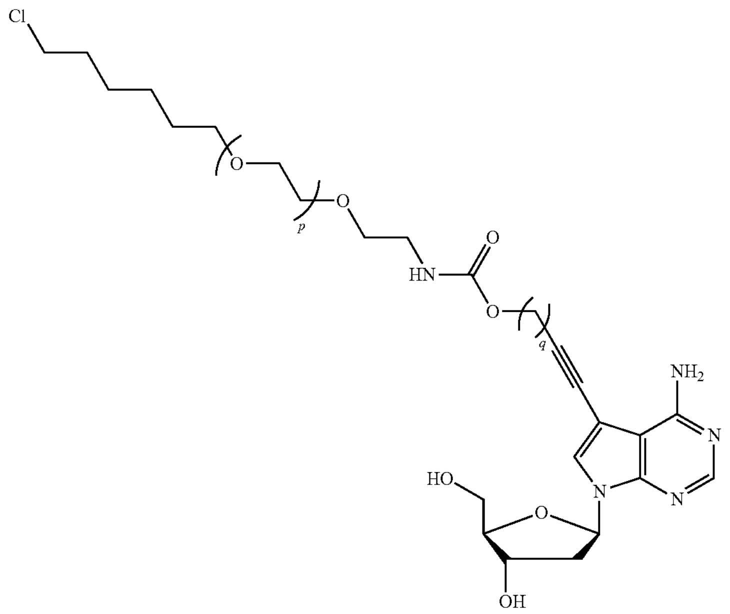
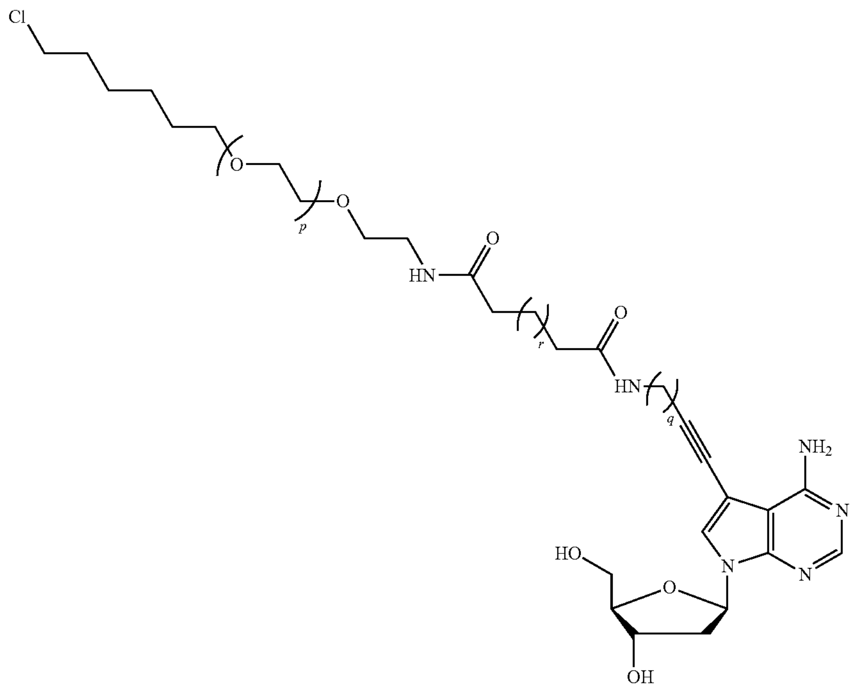

-continued
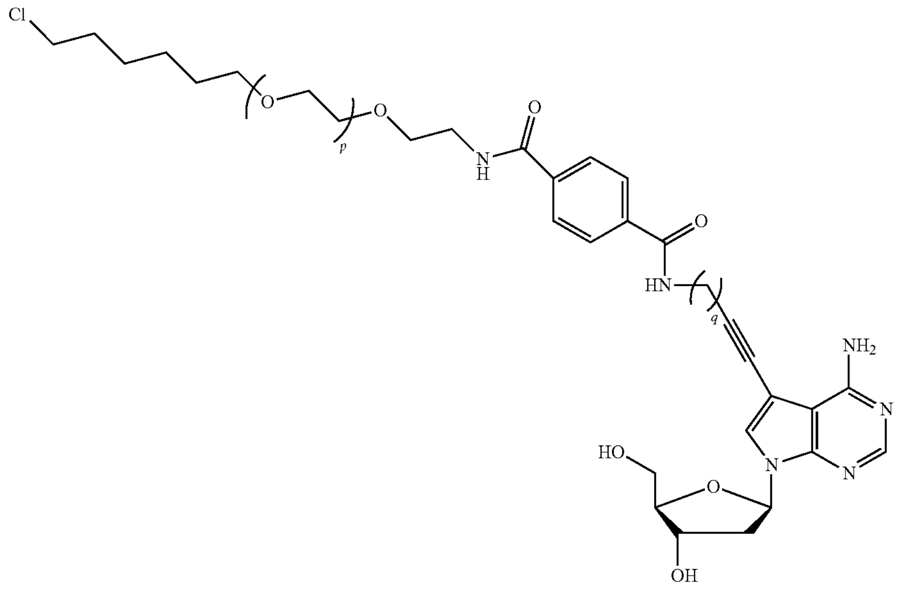
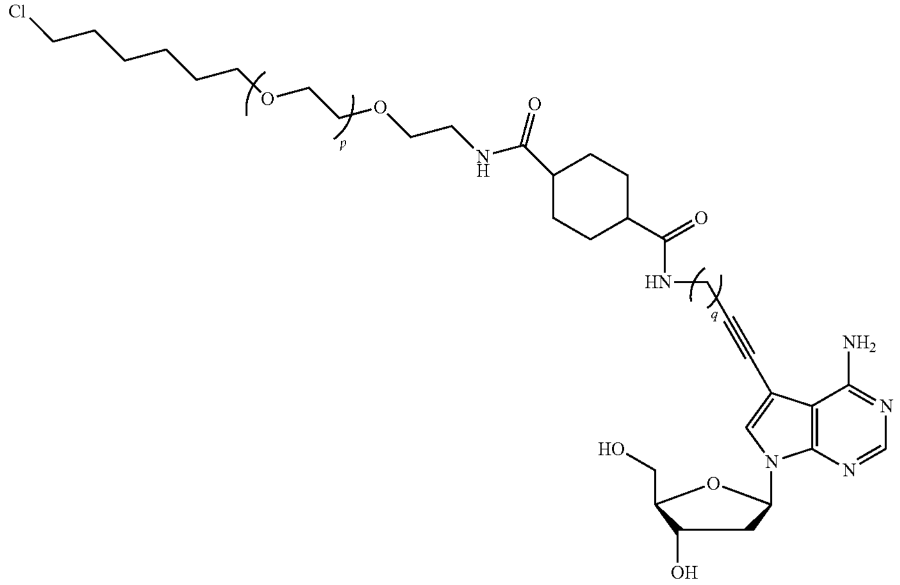

-continued
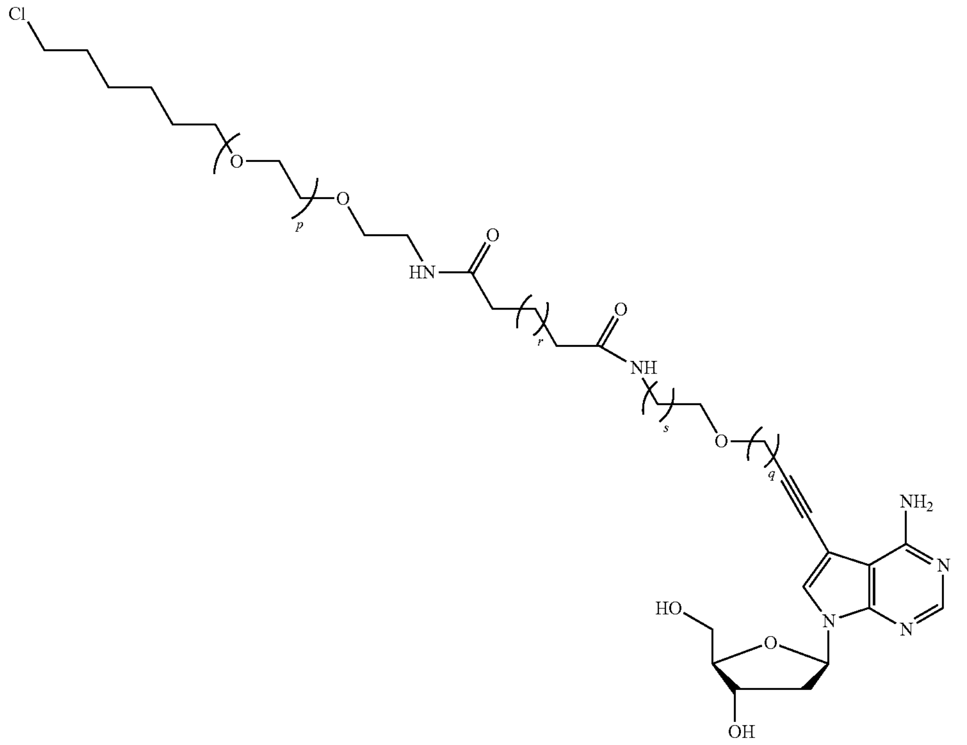
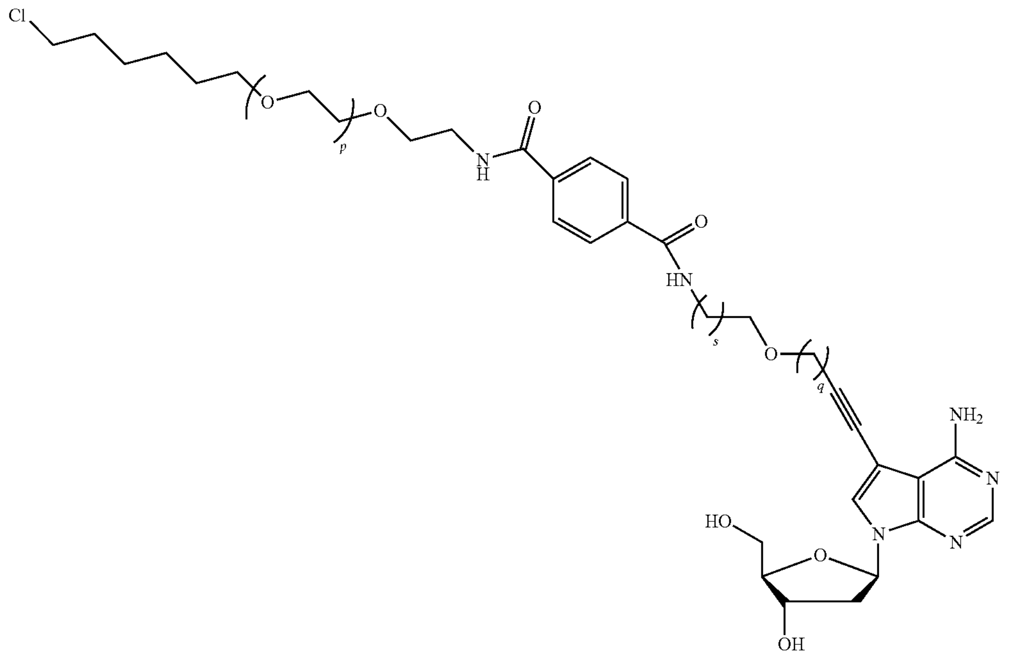

-continued
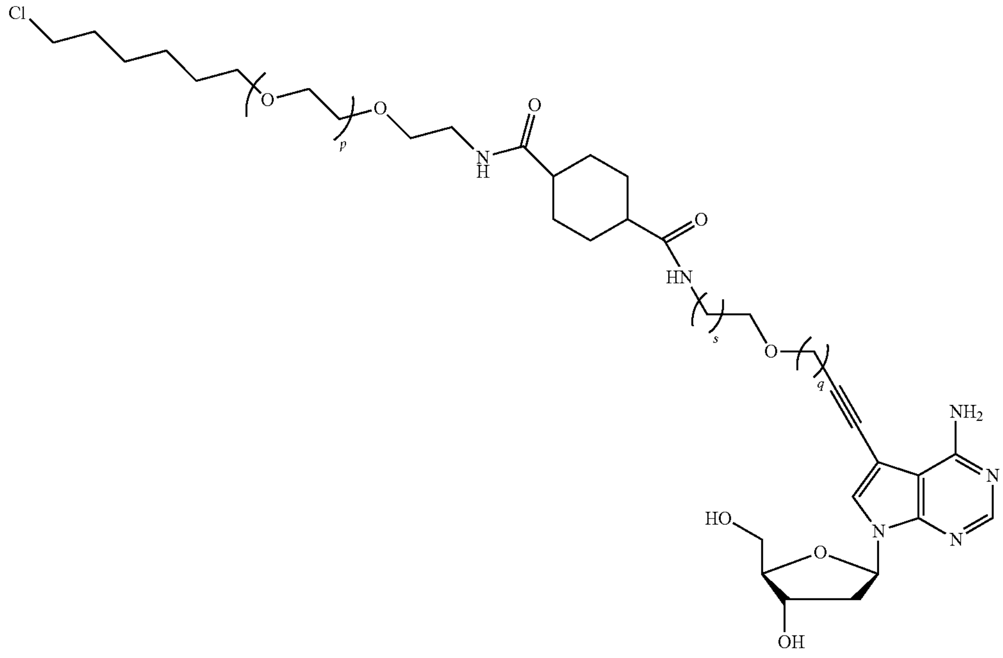
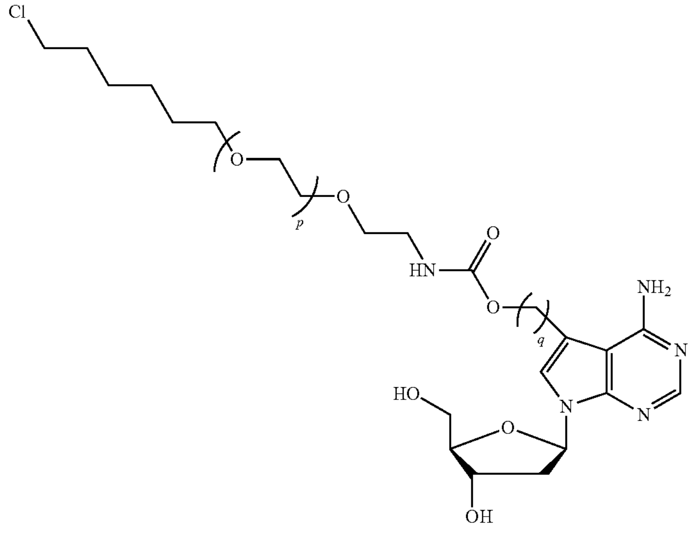

-continued
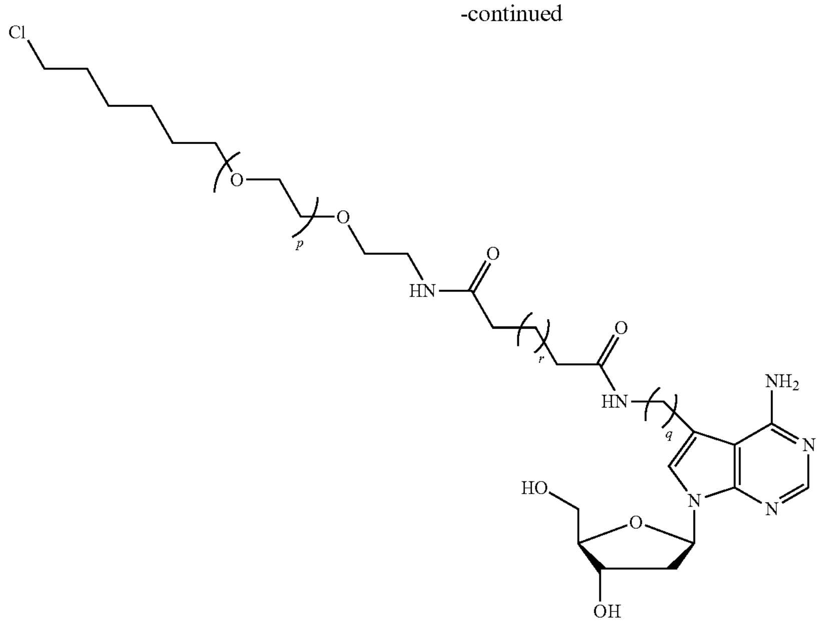
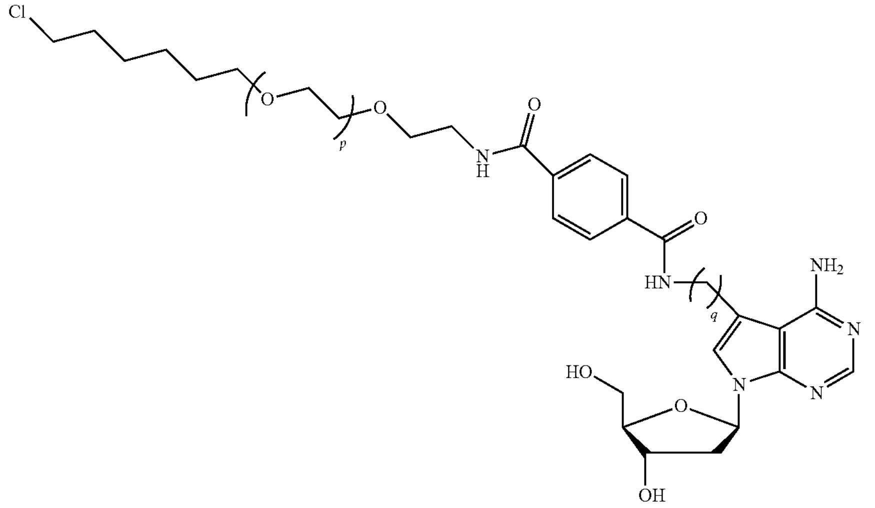
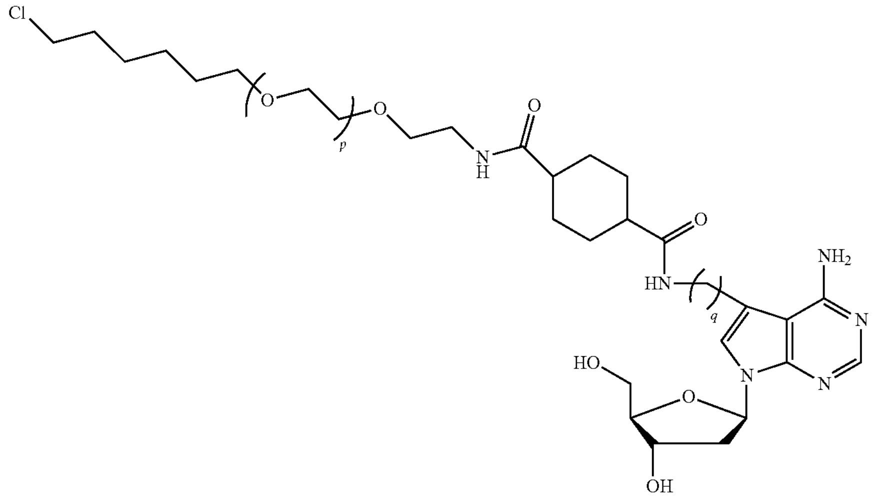

-continued
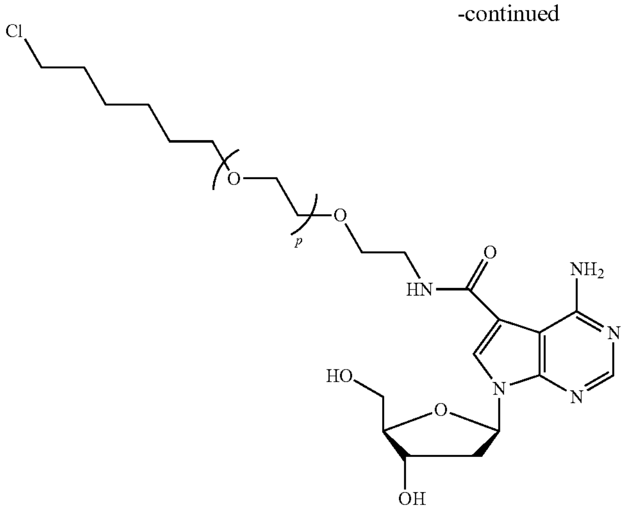
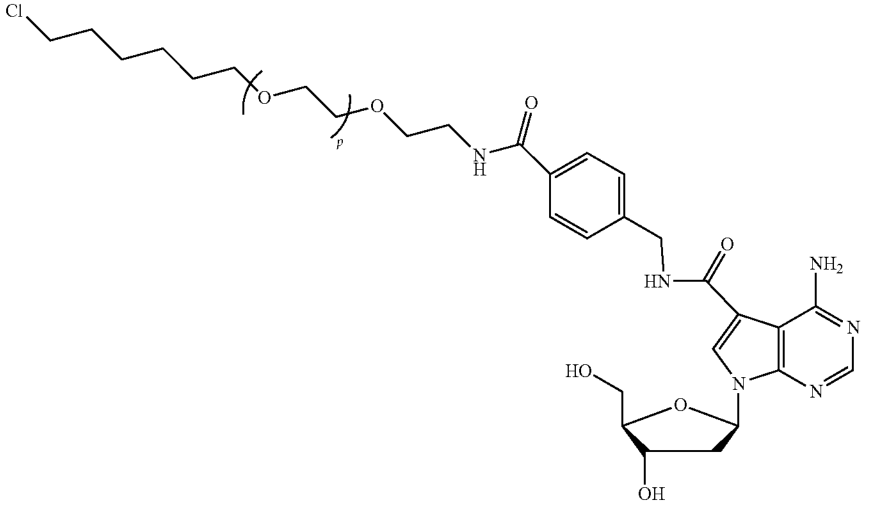
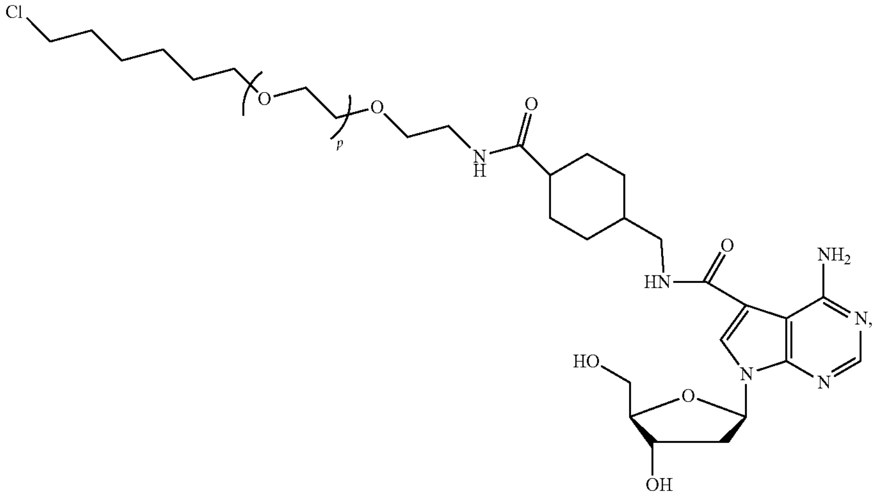
wherein p, q, r, and s are independently 1-6.

In some embodiments, a compound of formula (IV) is selected from:
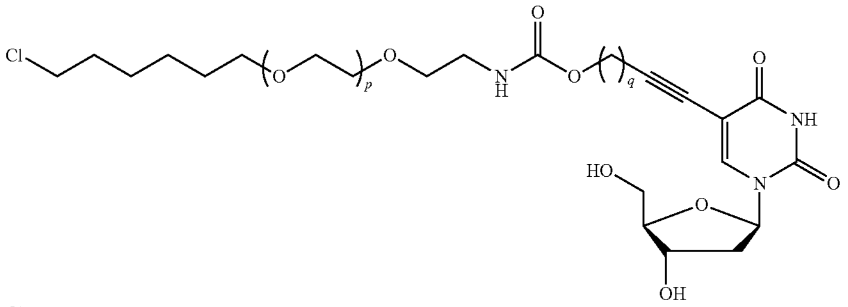
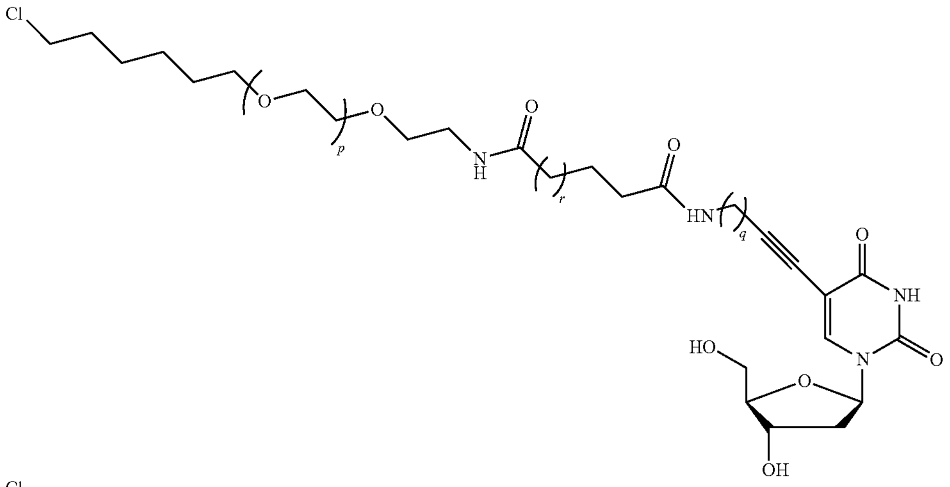
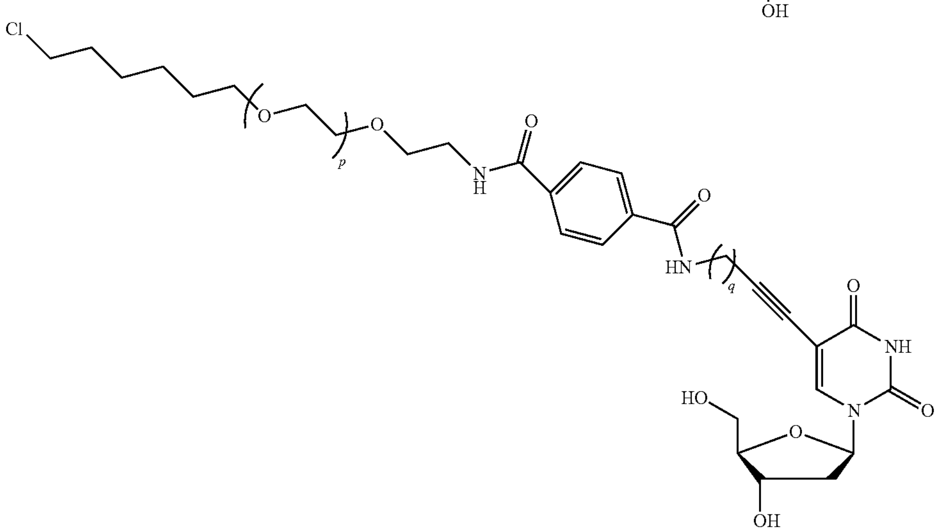
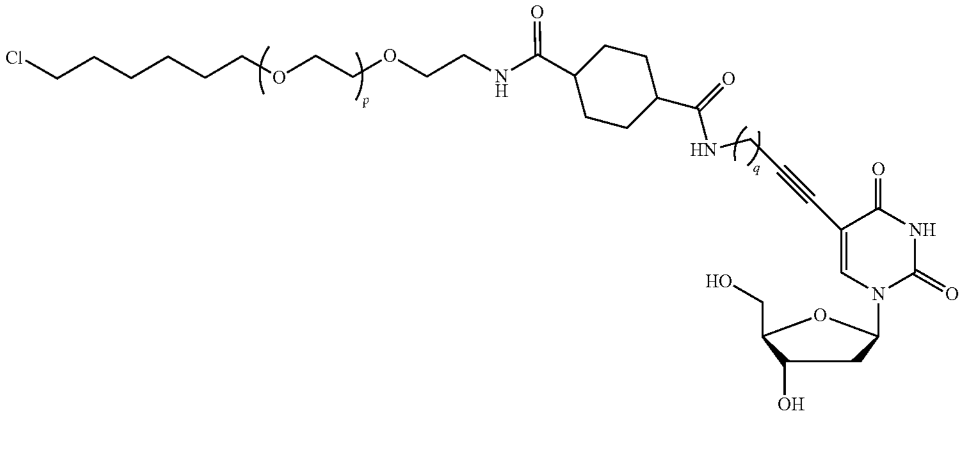

-continued
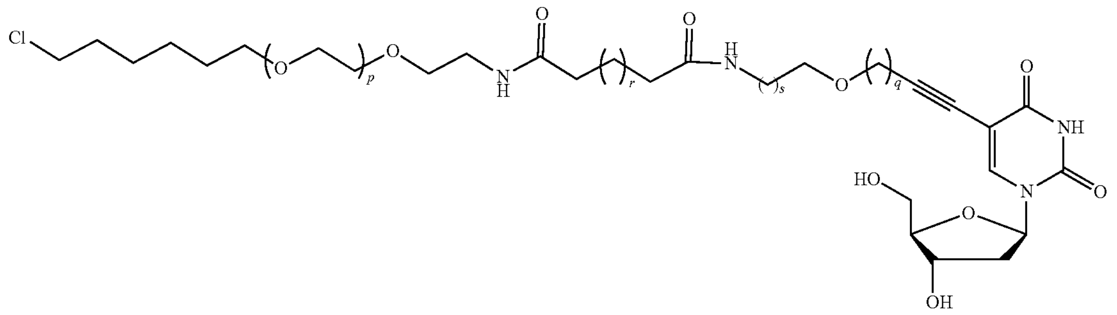
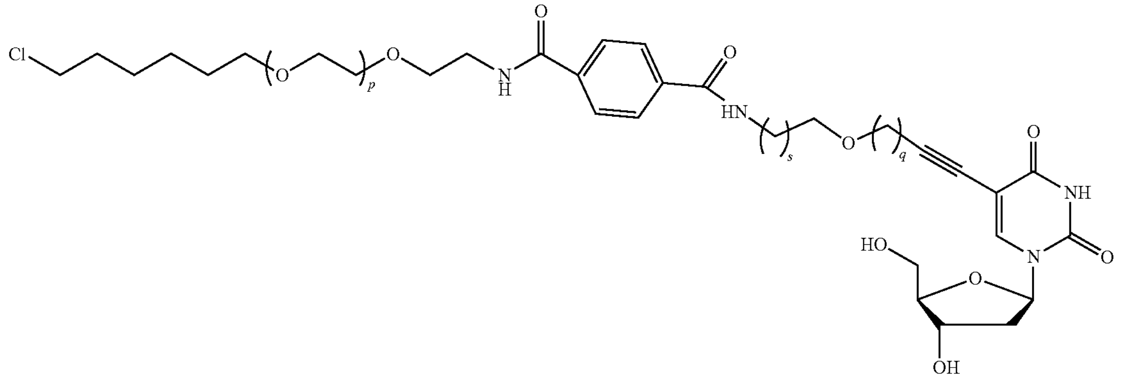
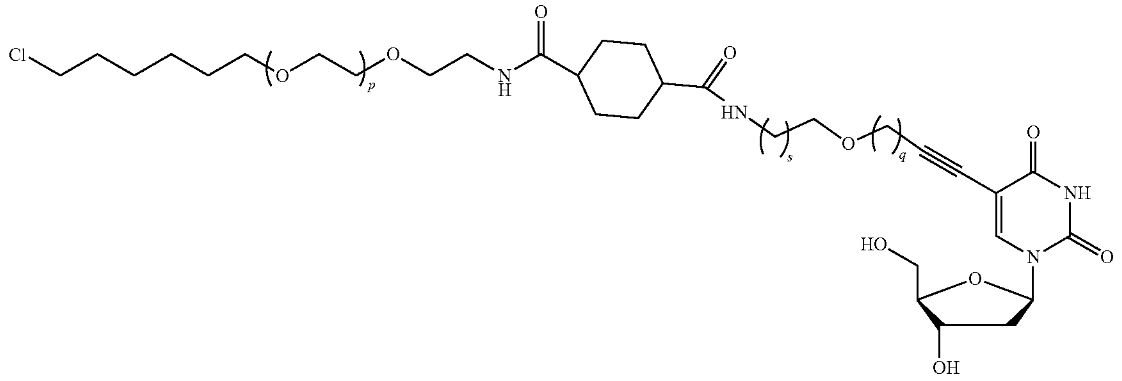
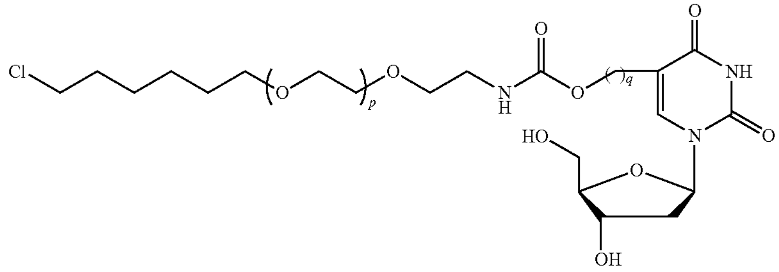

-continued
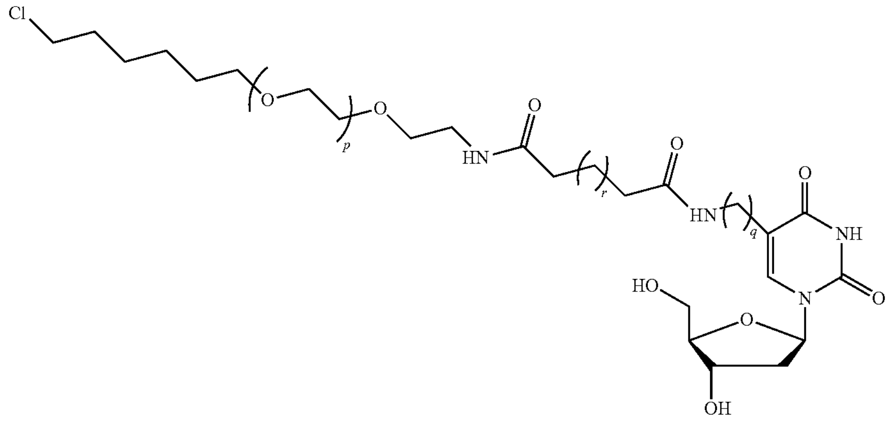
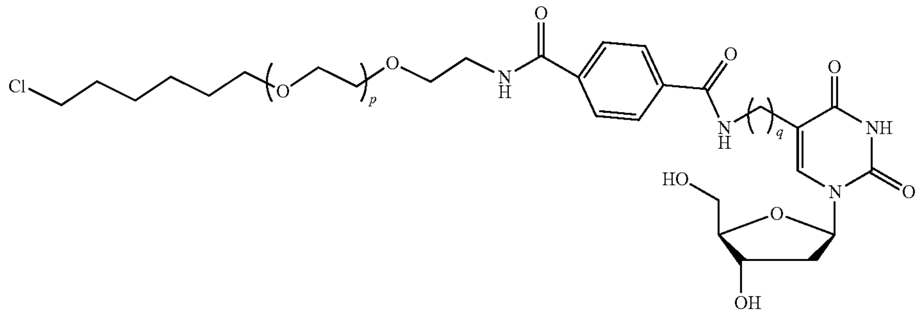
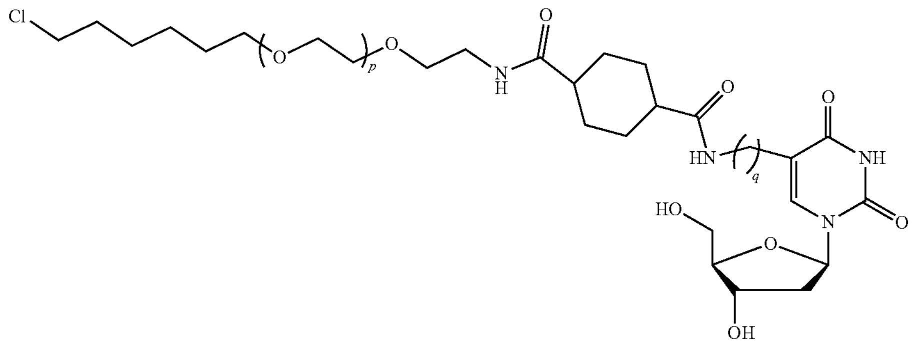
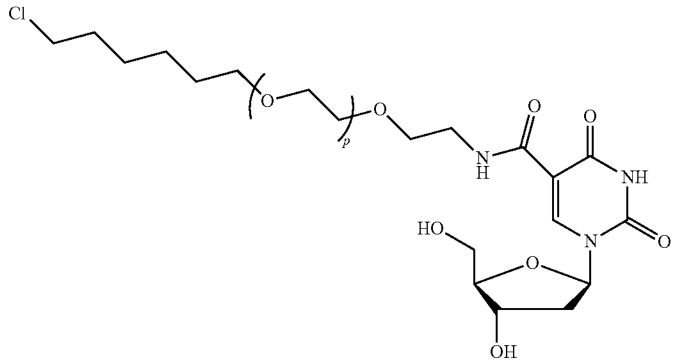

-continued
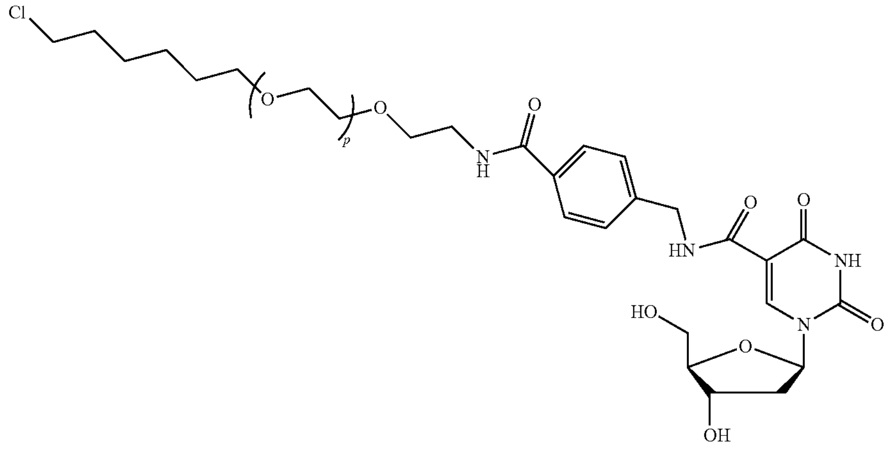
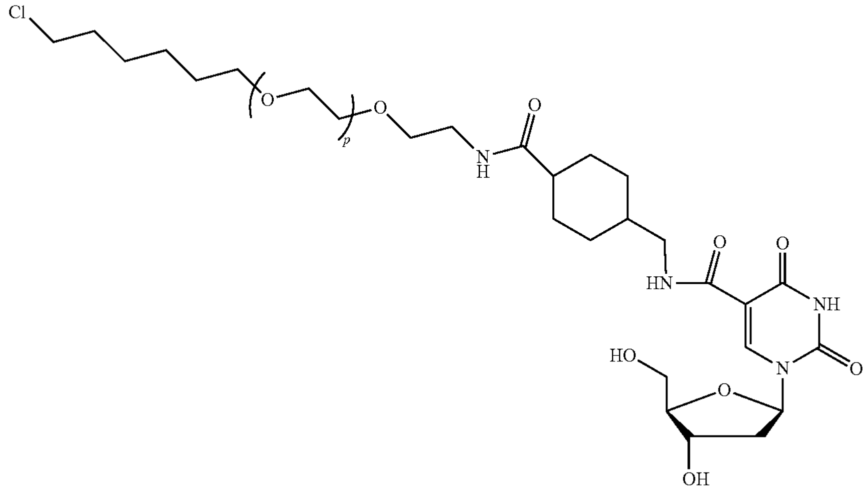
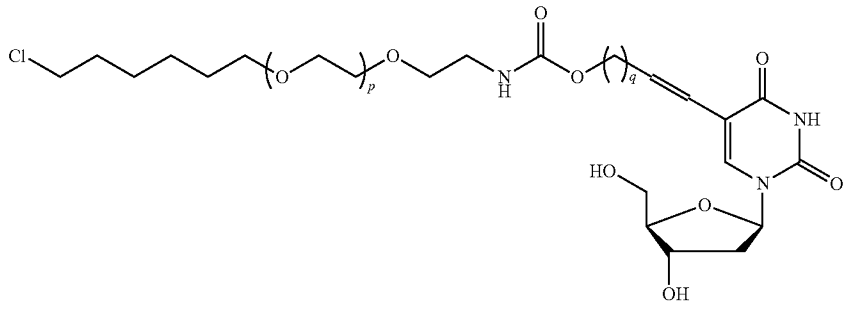
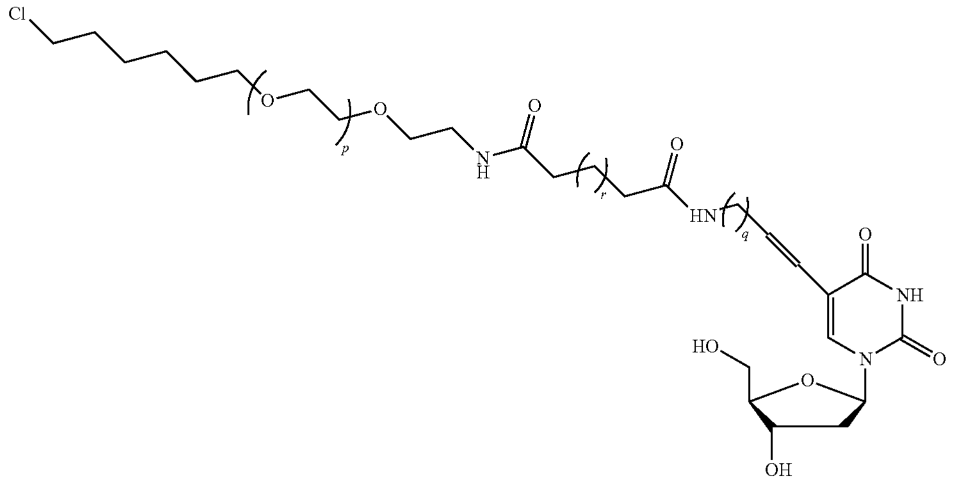

-continued
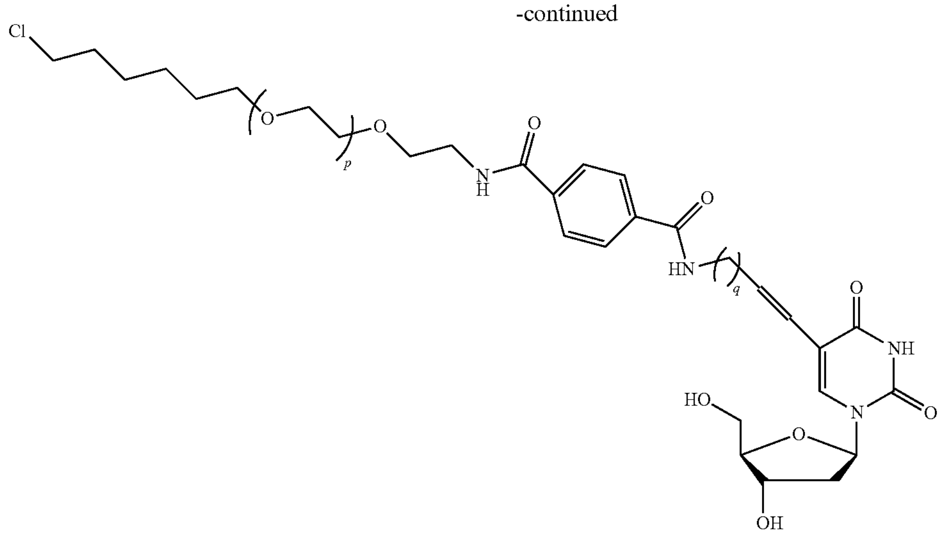
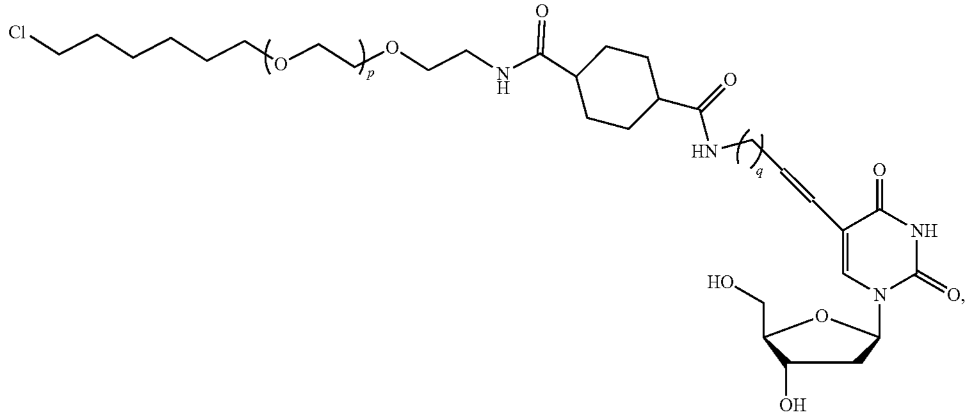
wherein p, q, r, and s are independently 1-6.
In some embodiments, a compound of formula (V) is selected from:
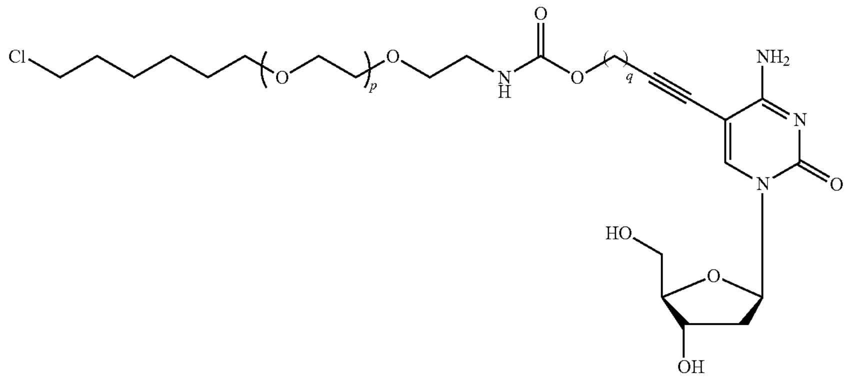

-continued
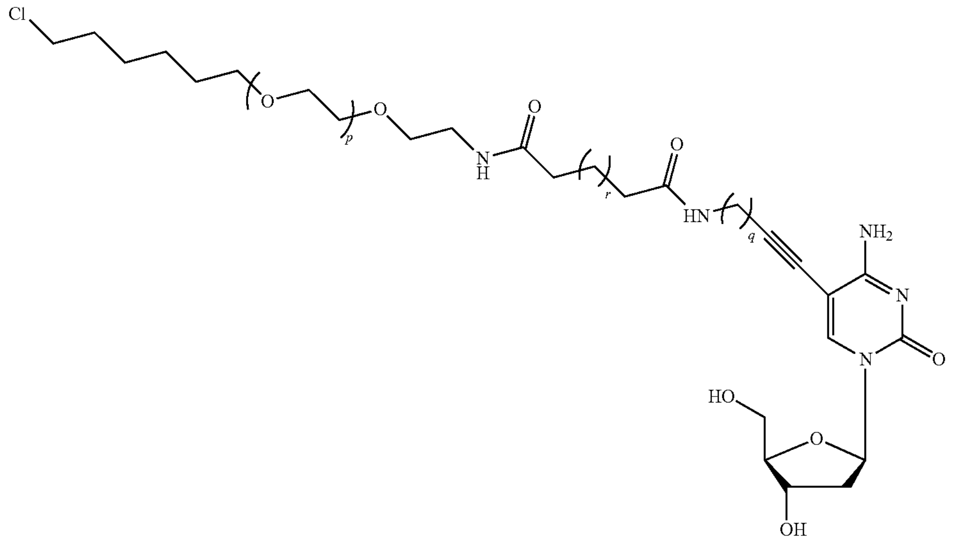
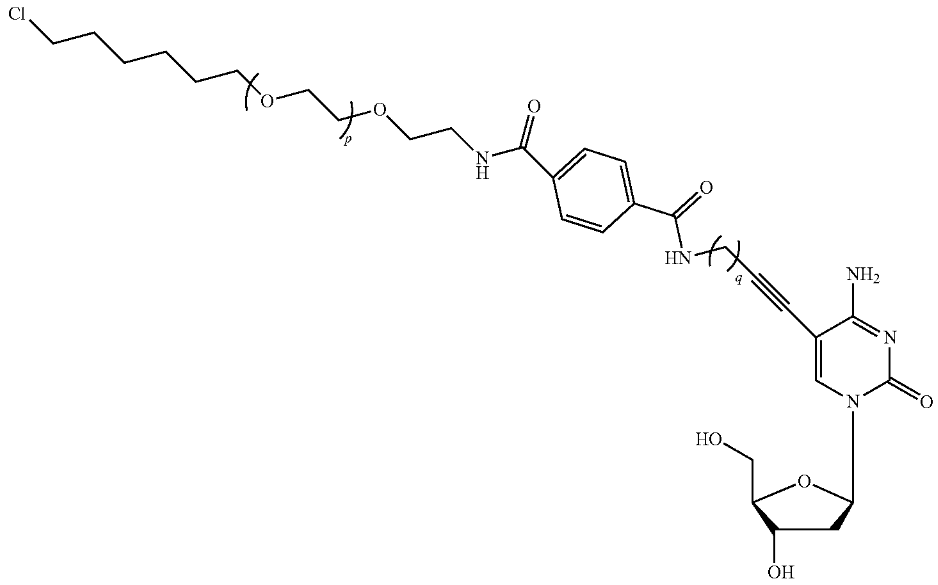
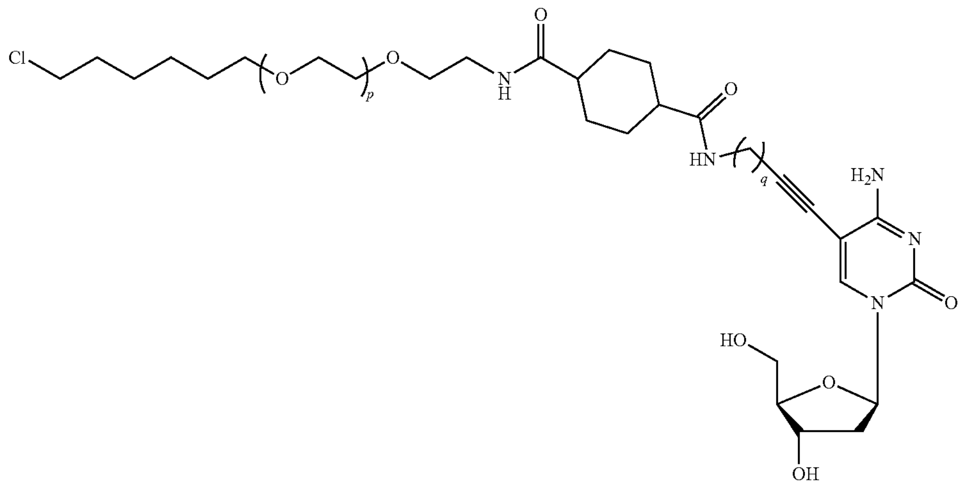

-continued
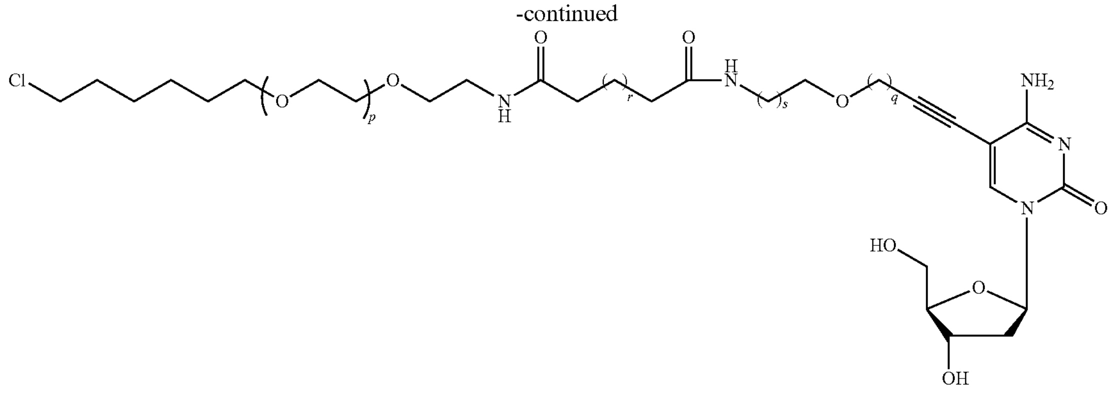
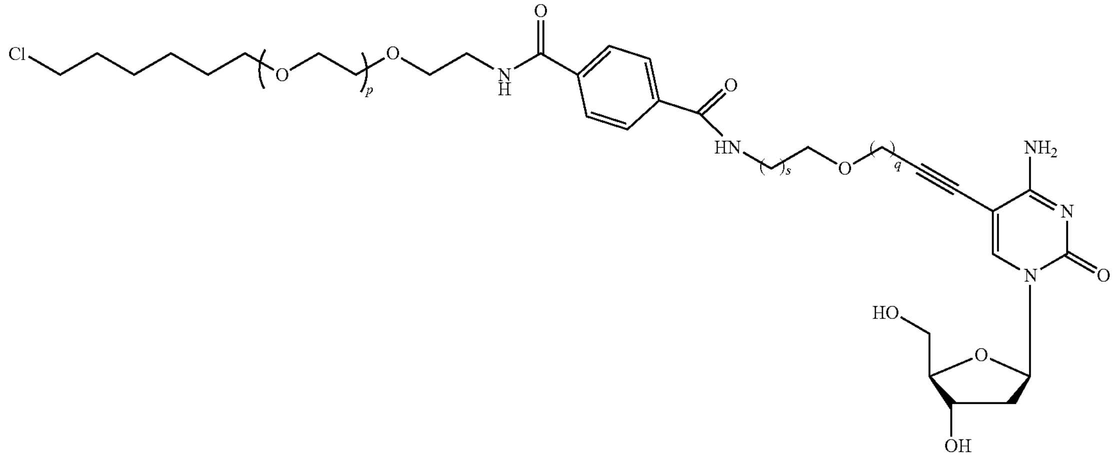
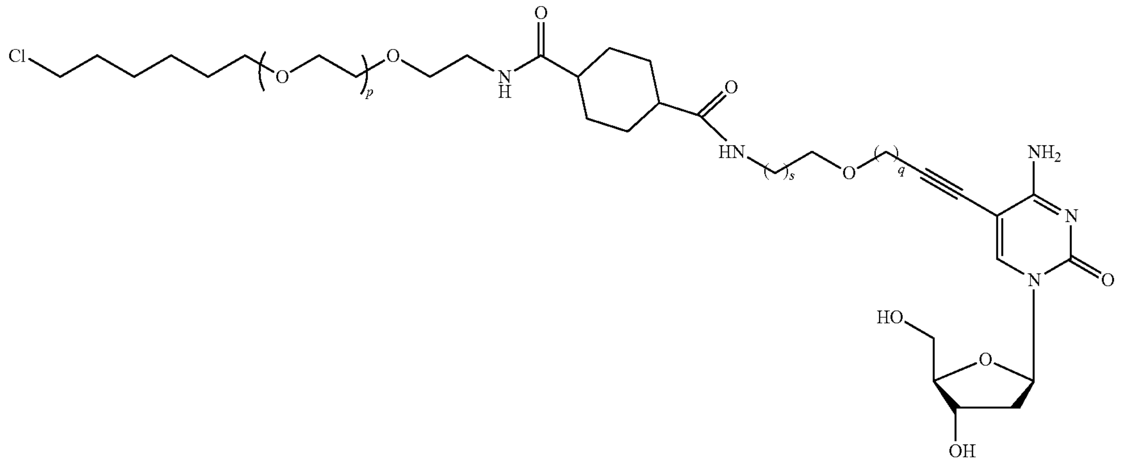
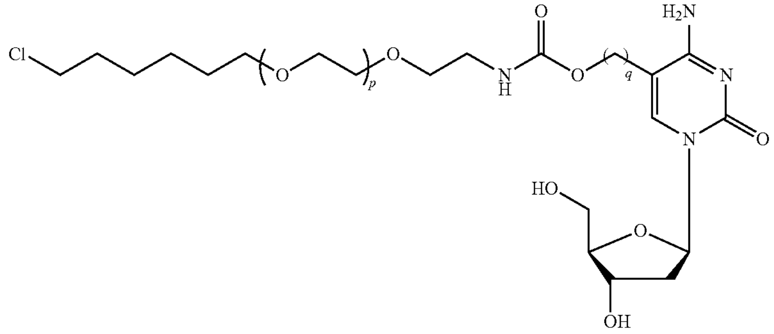

-continued
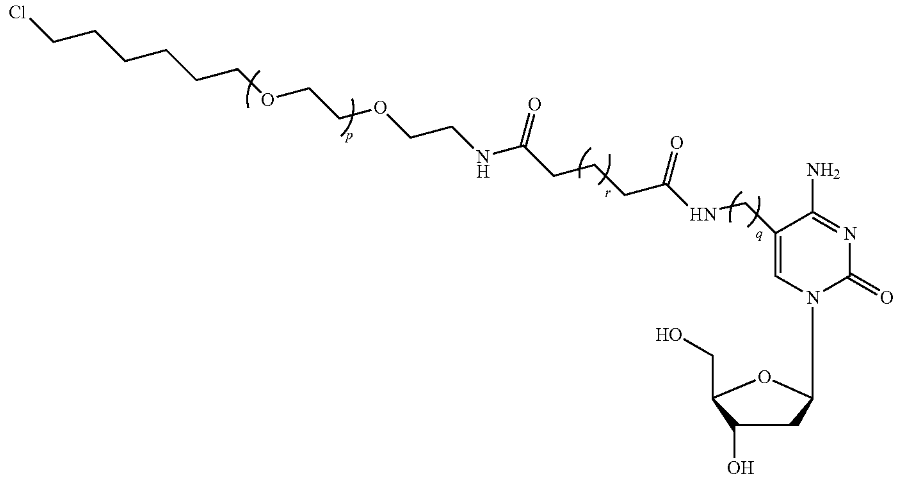
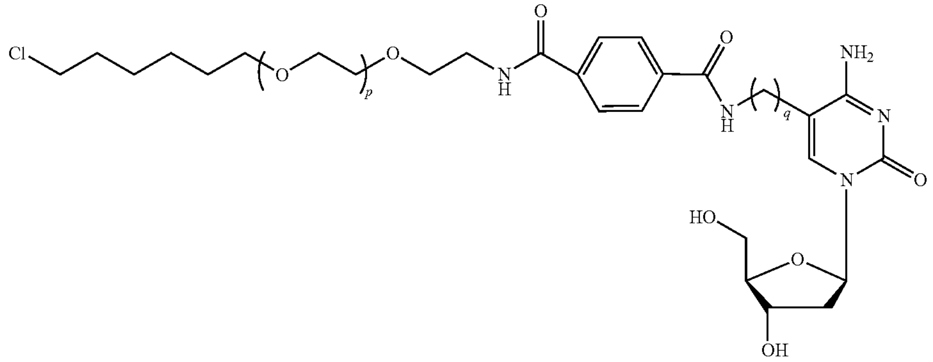
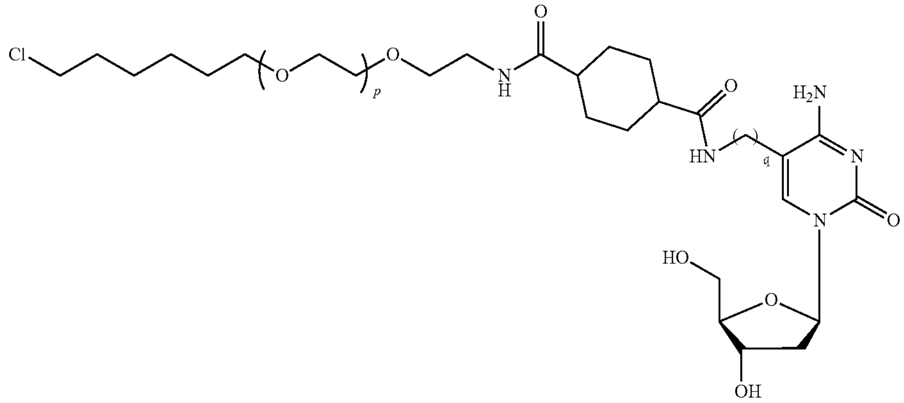
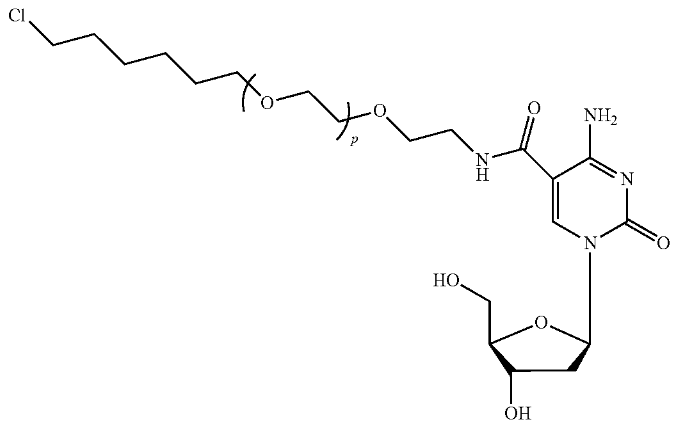

-continued
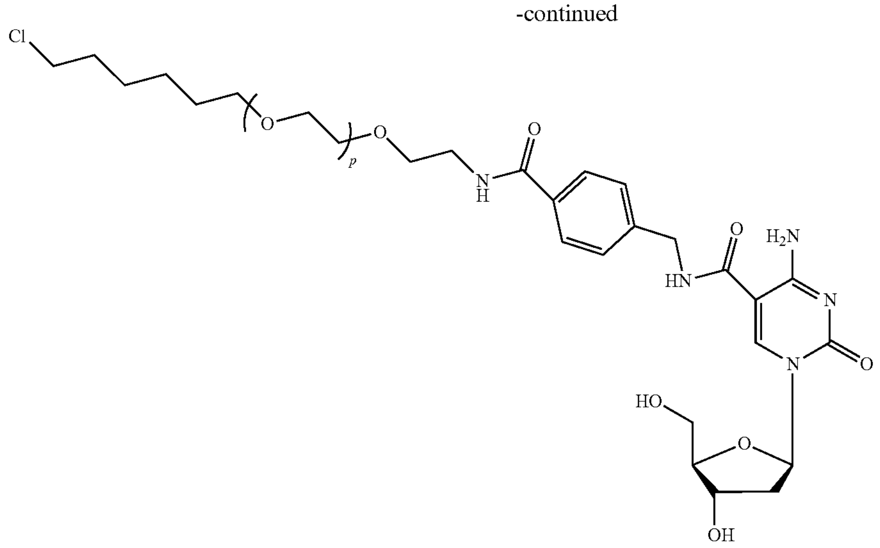
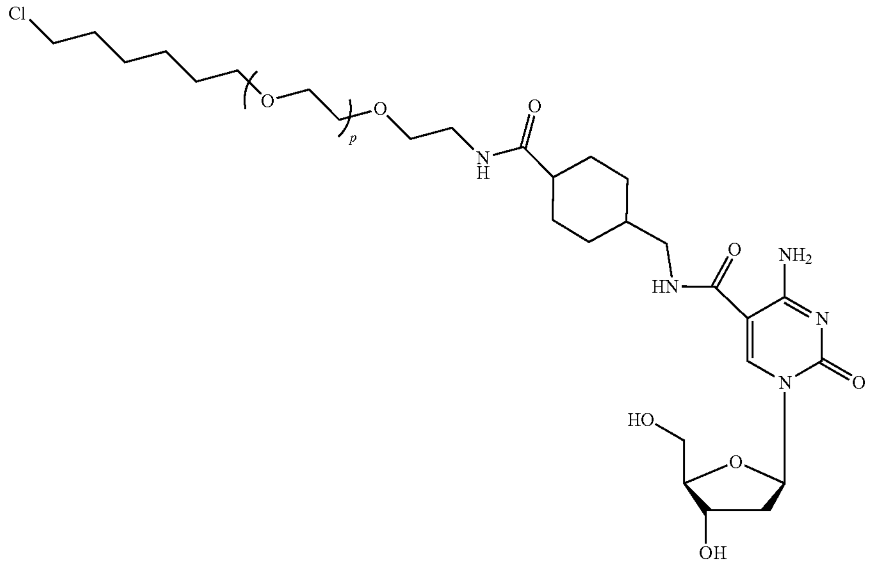
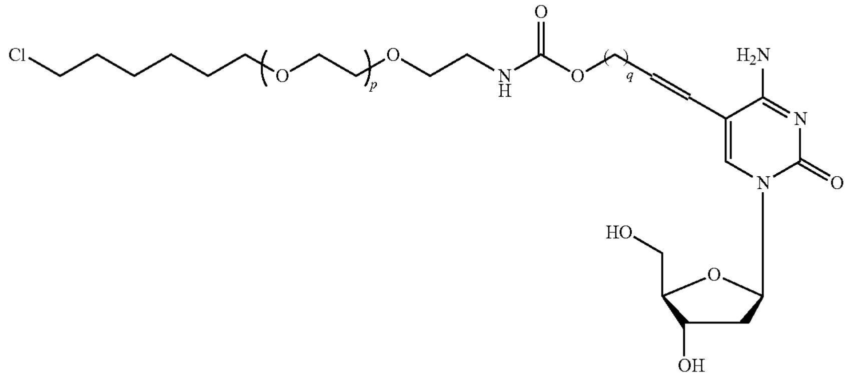

-continued
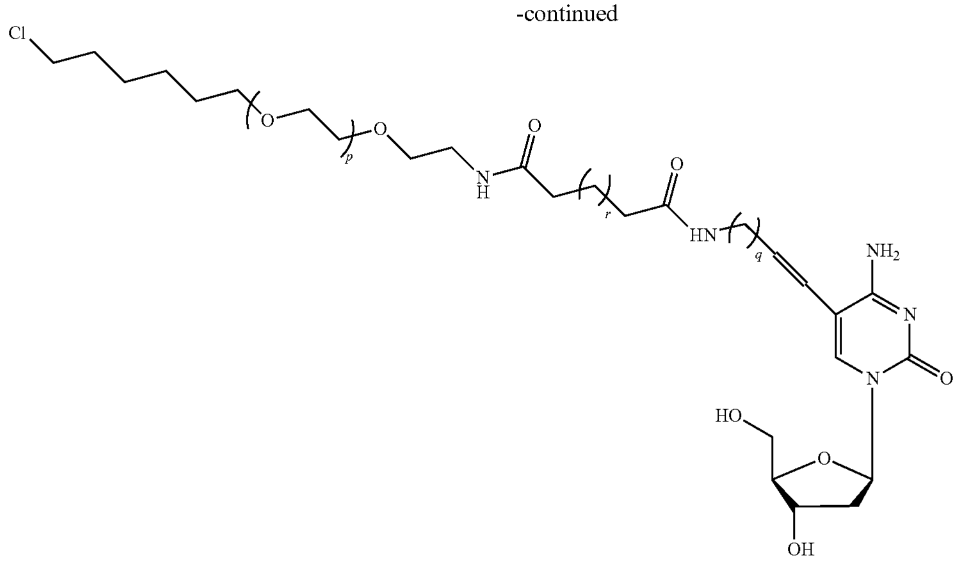
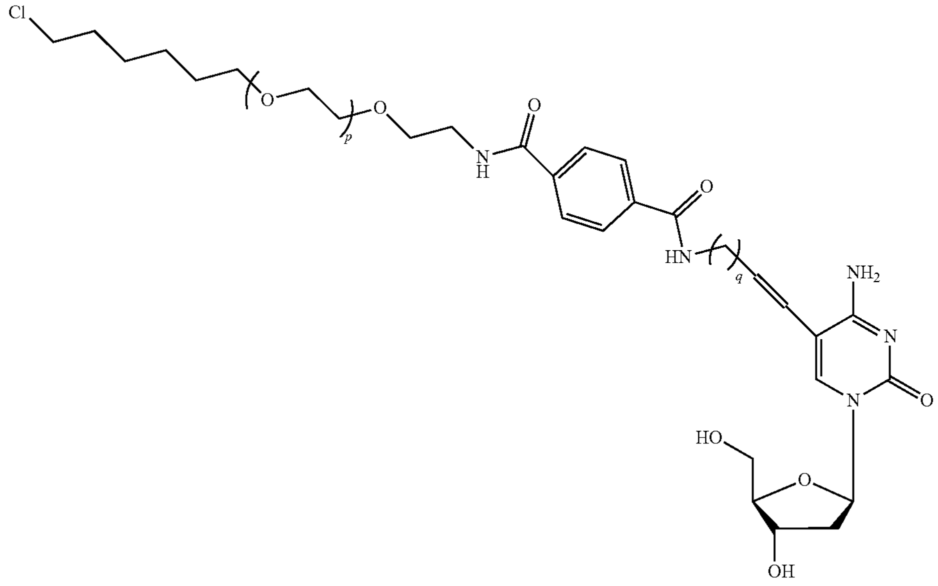
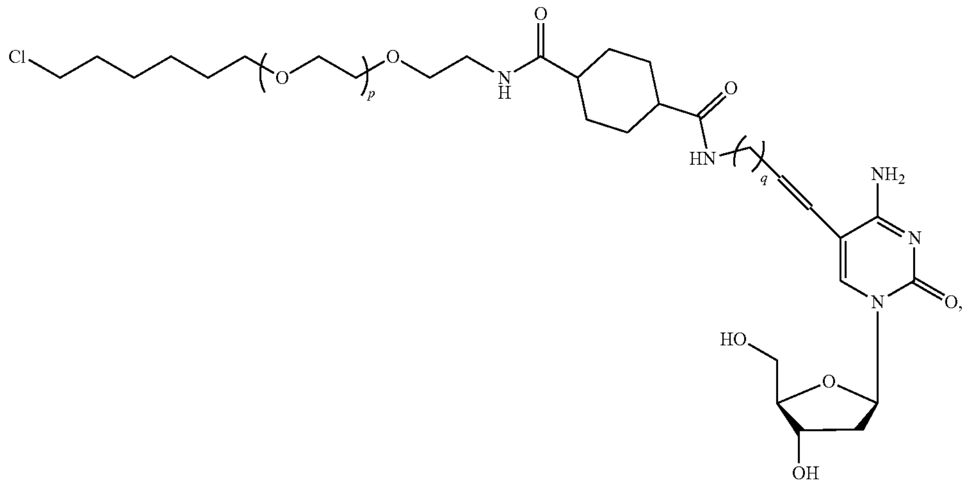
wherein p, q, r, and s are independently 1-6.

In some embodiments, the compound is selected from:
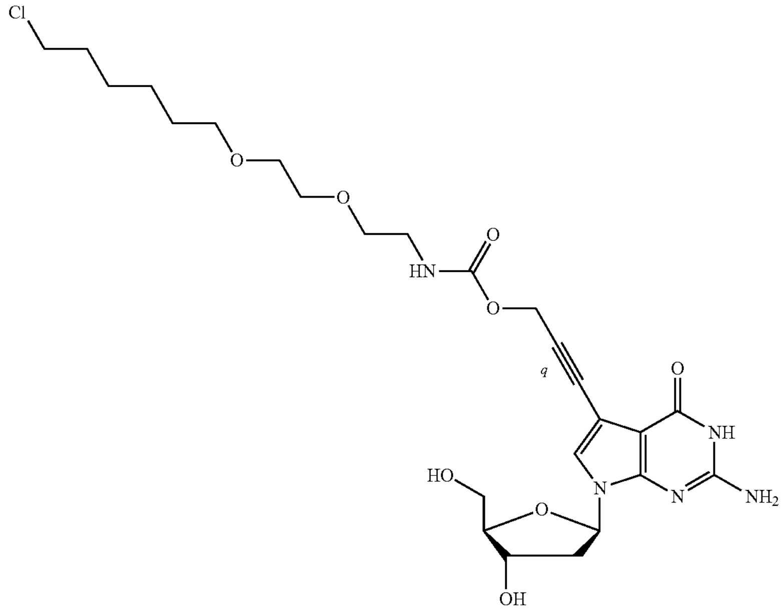
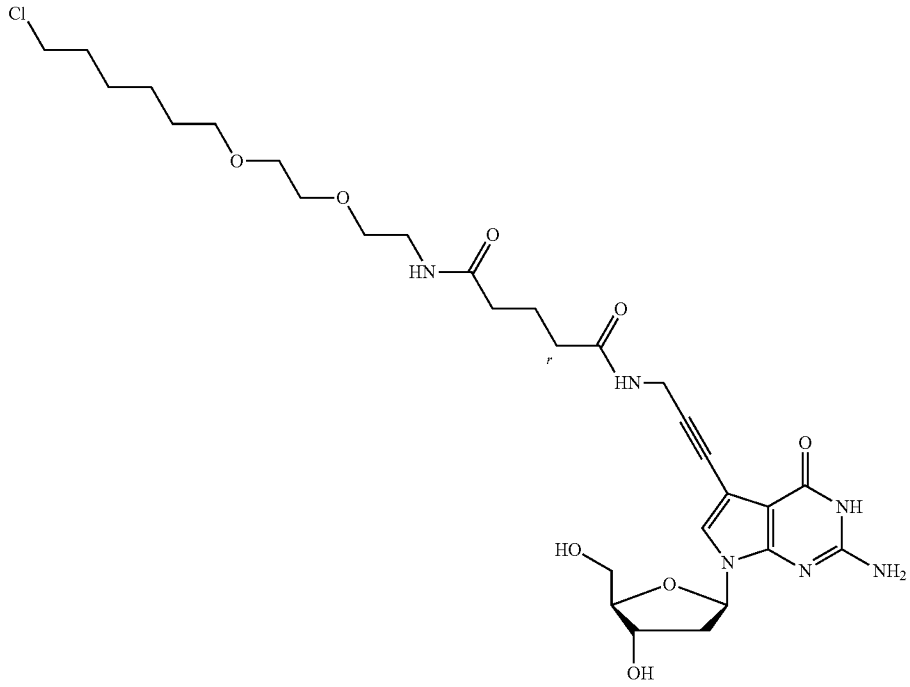

-continued
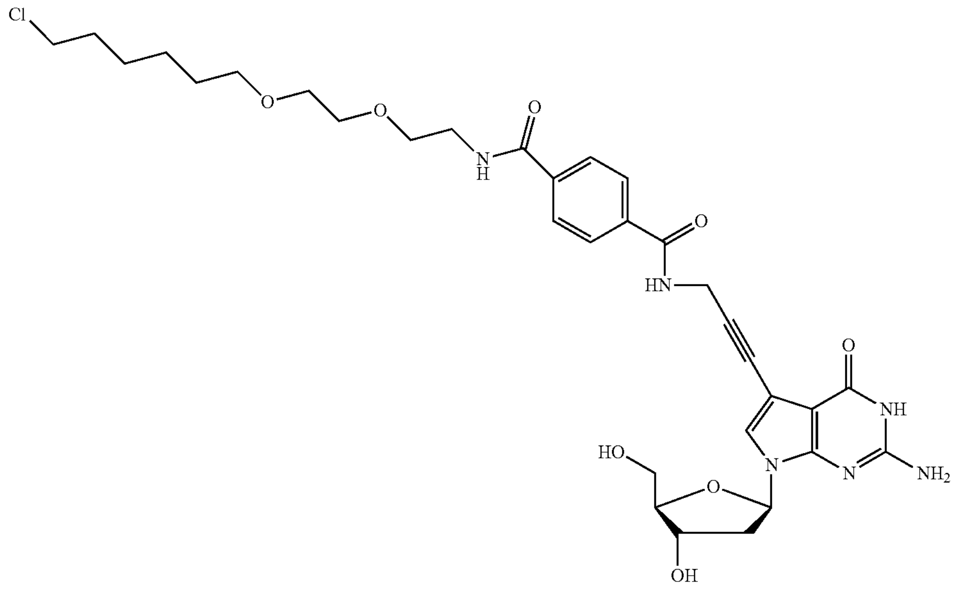
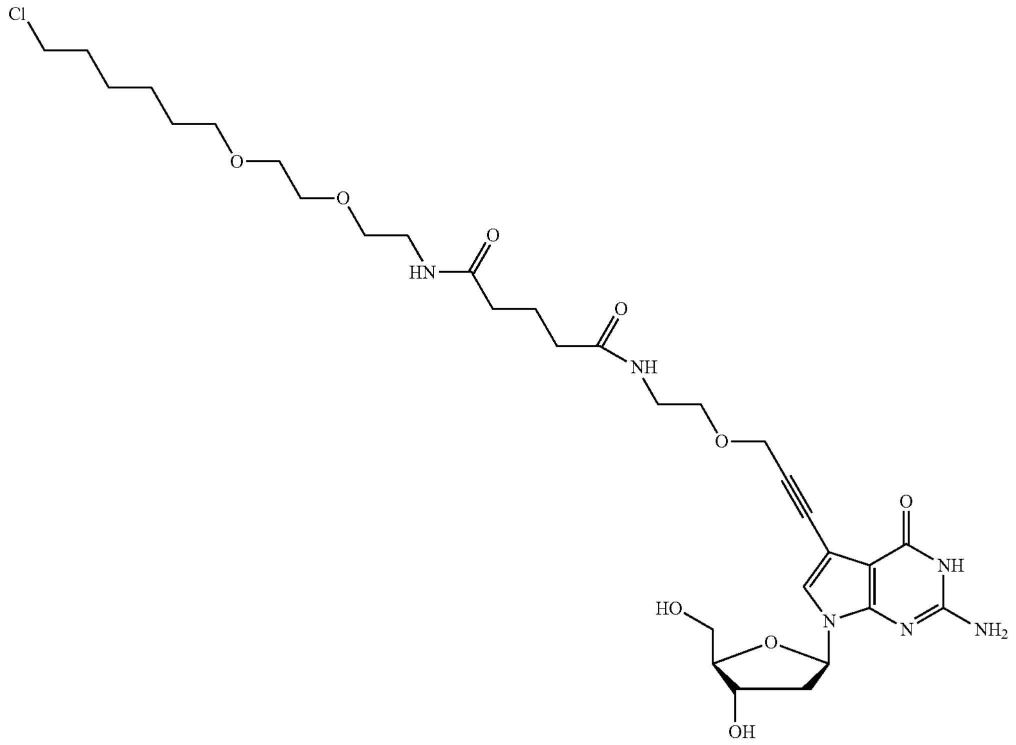

-continued
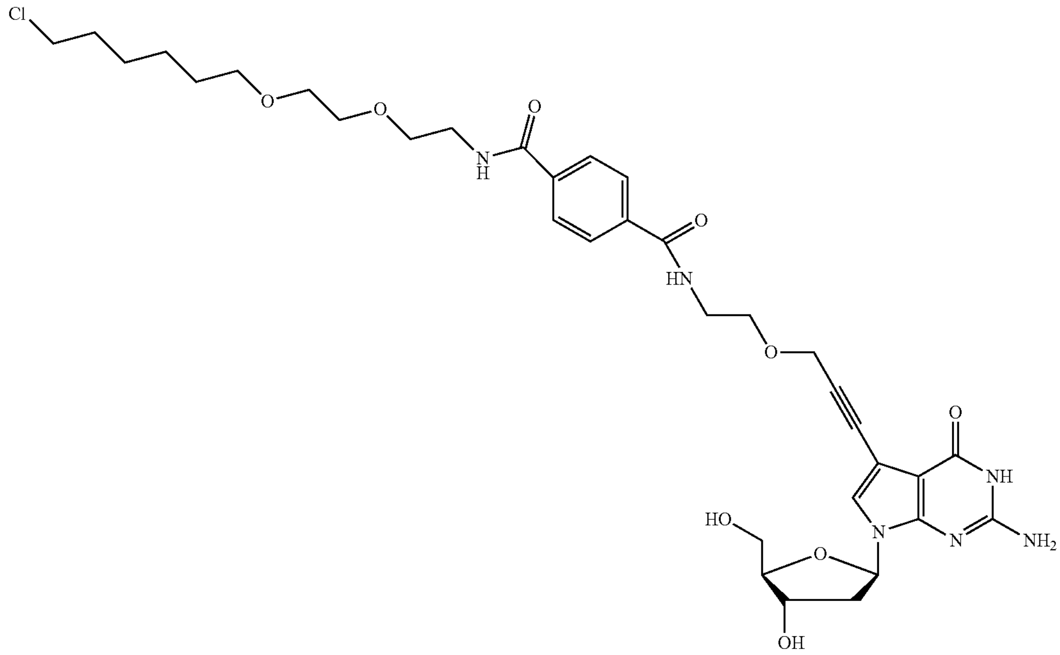
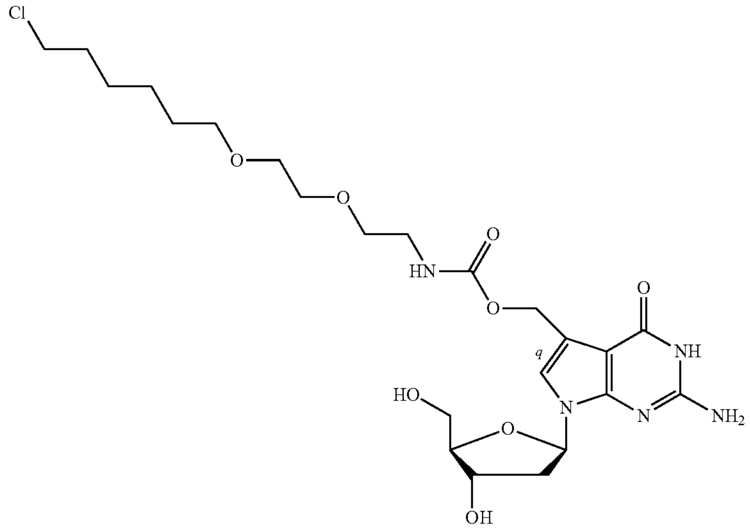

-continued
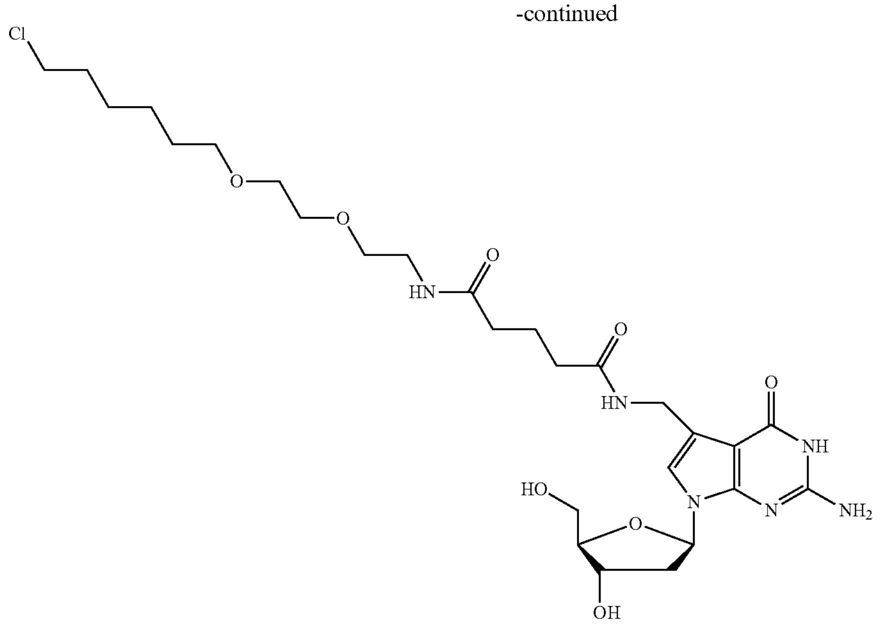
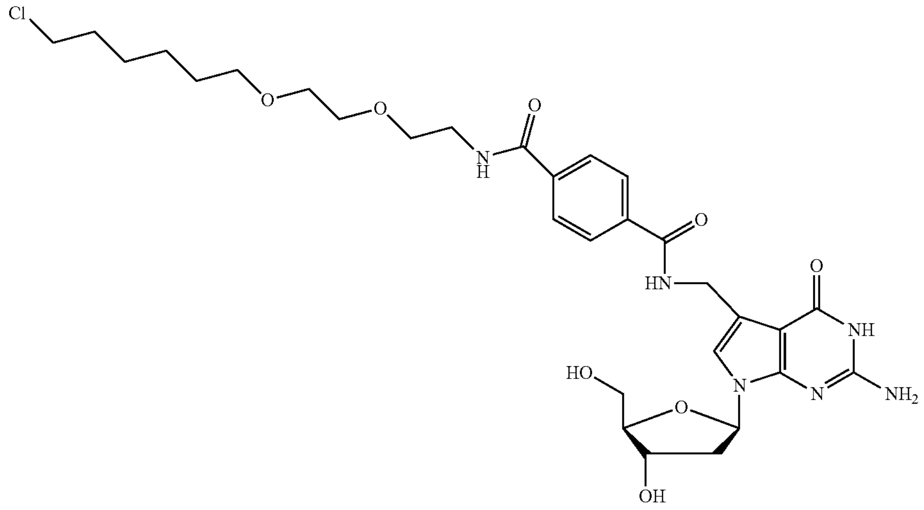
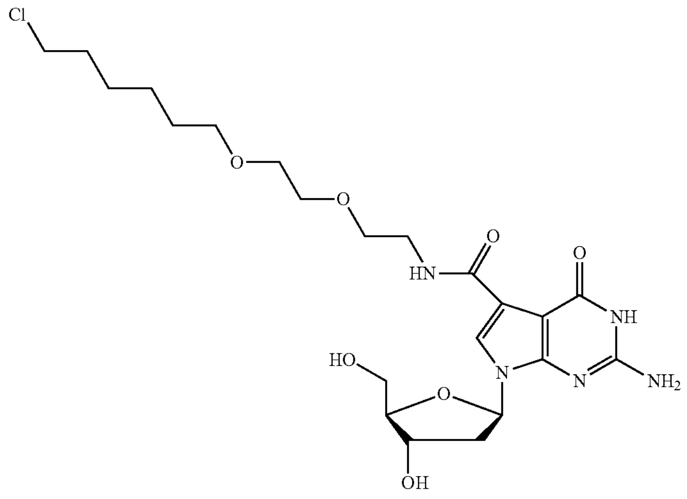

-continued
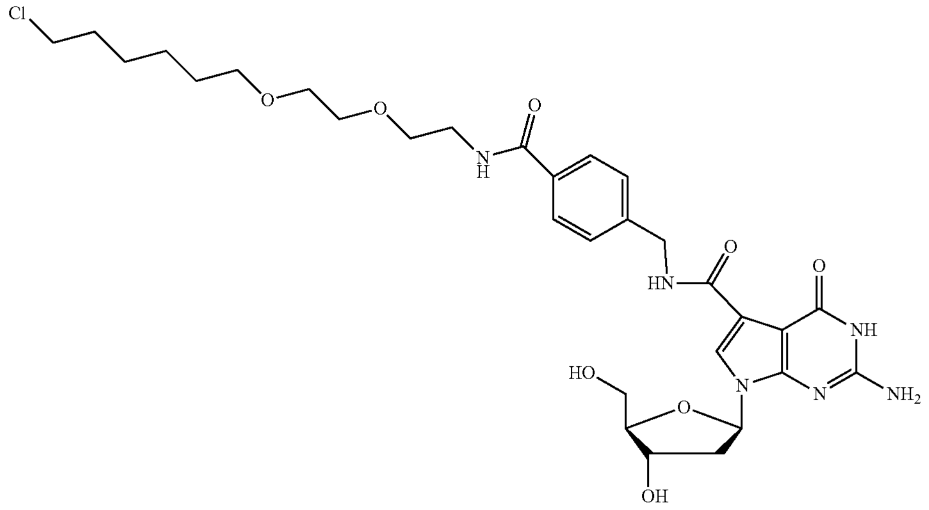
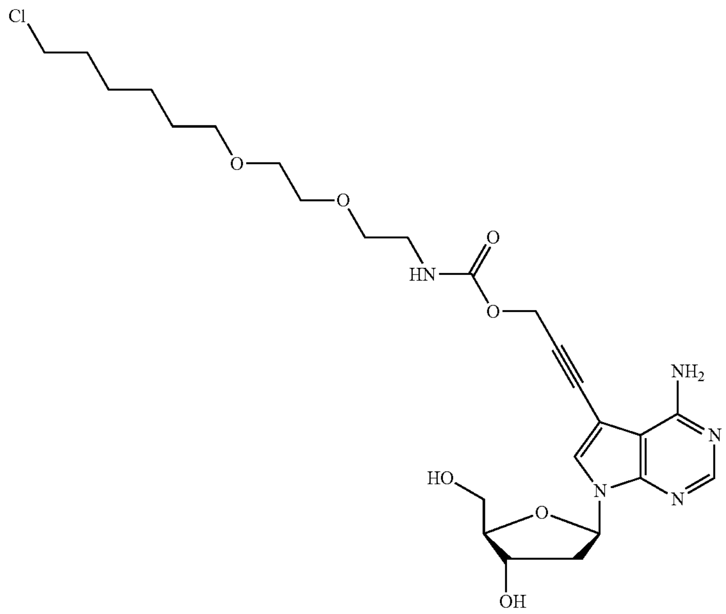

-continued
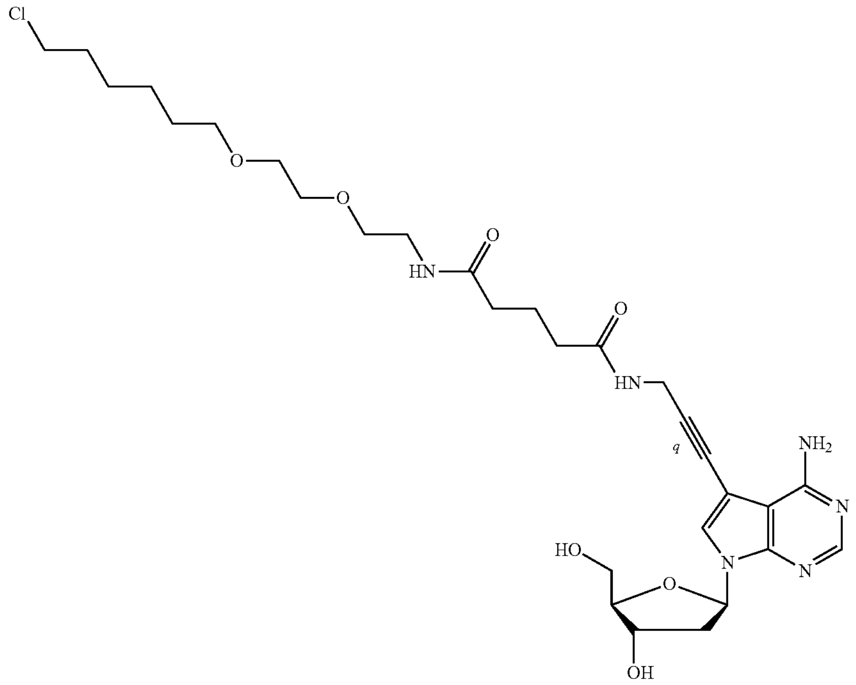
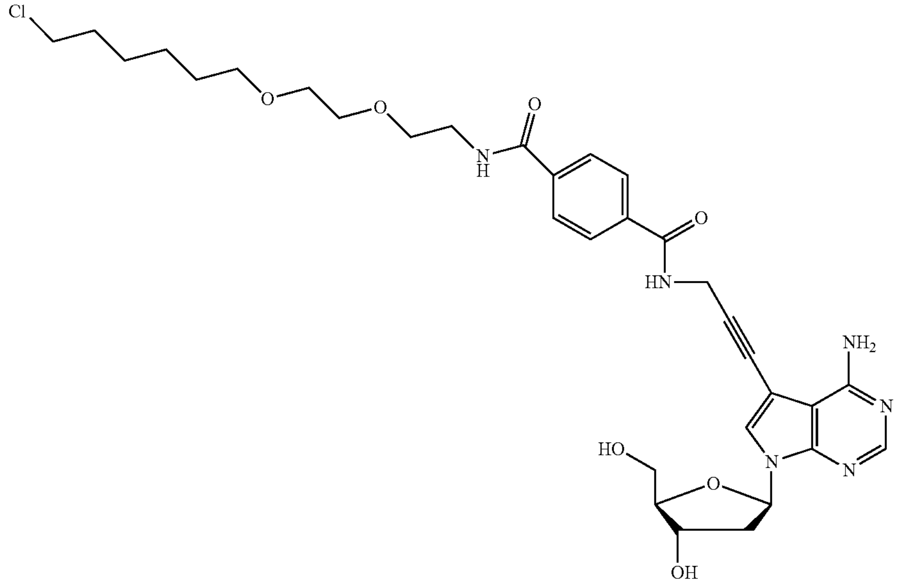

-continued
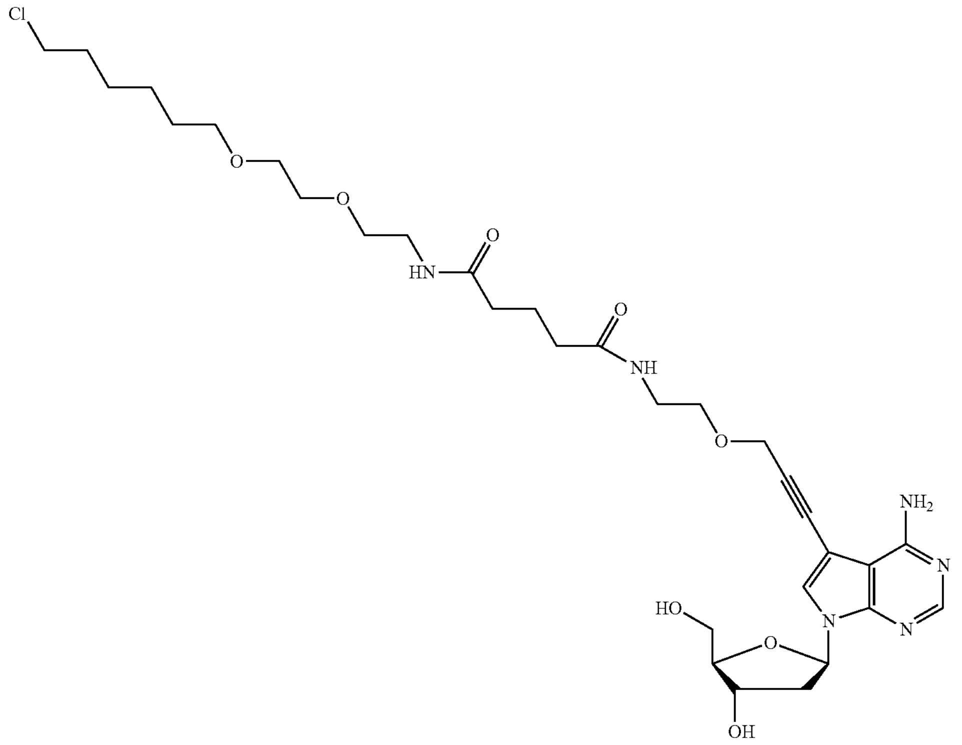
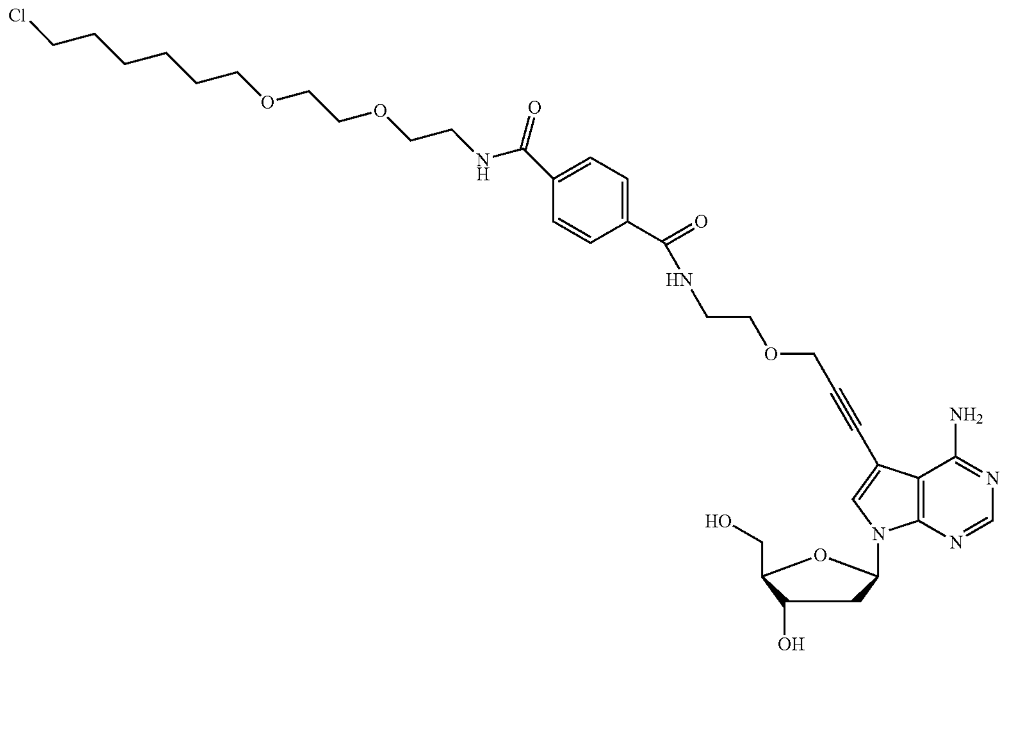

-continued
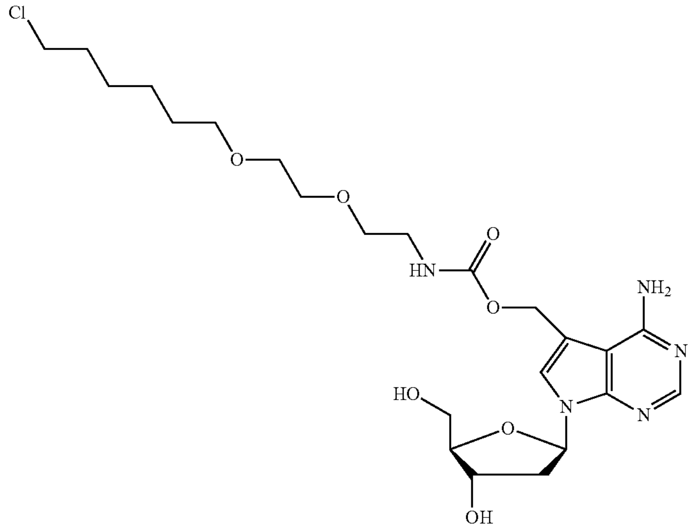
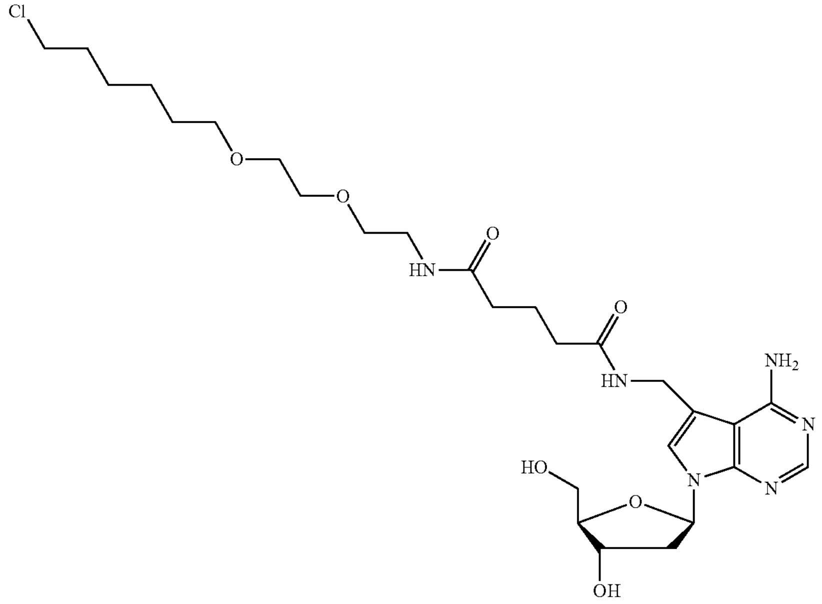
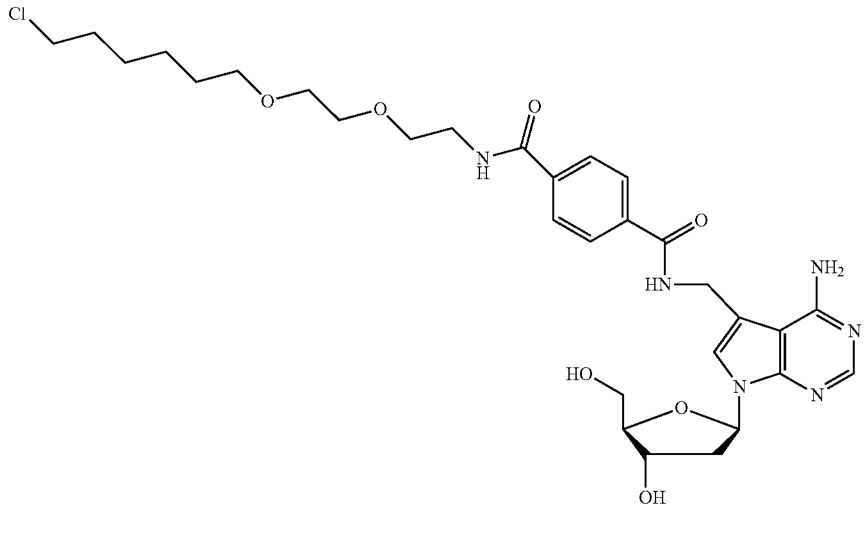

-continued
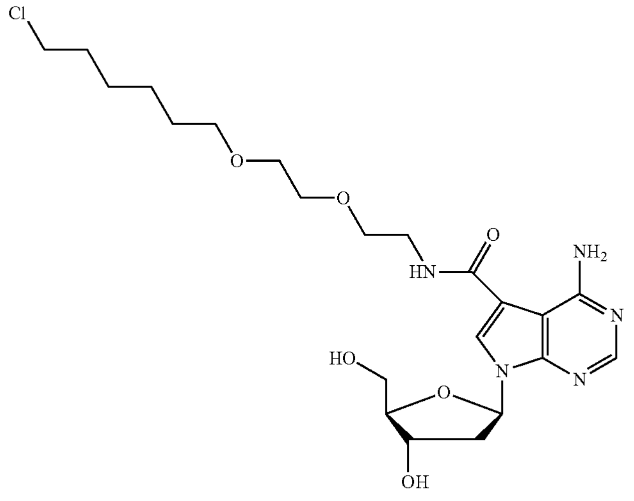
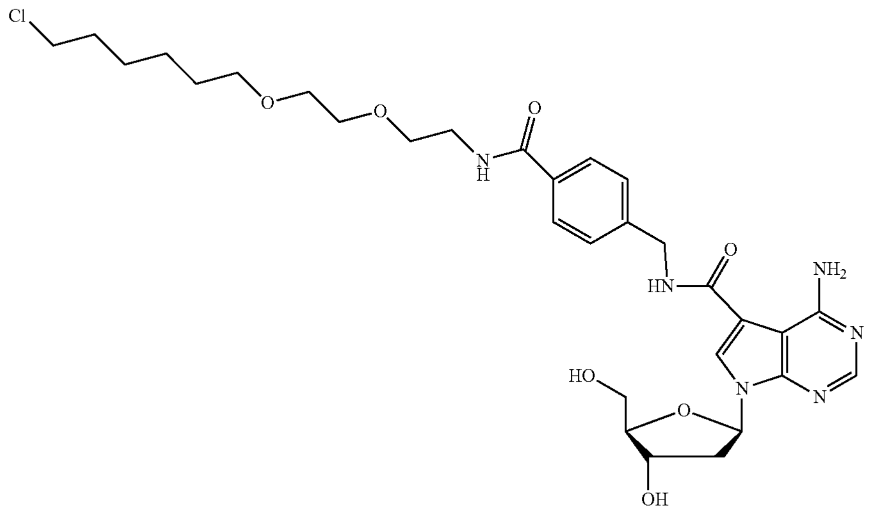
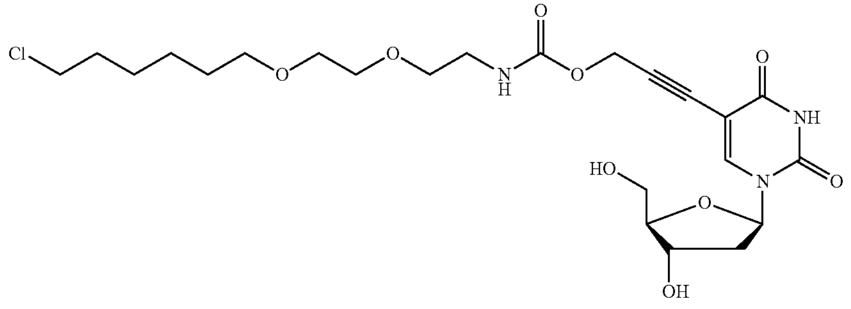

-continued
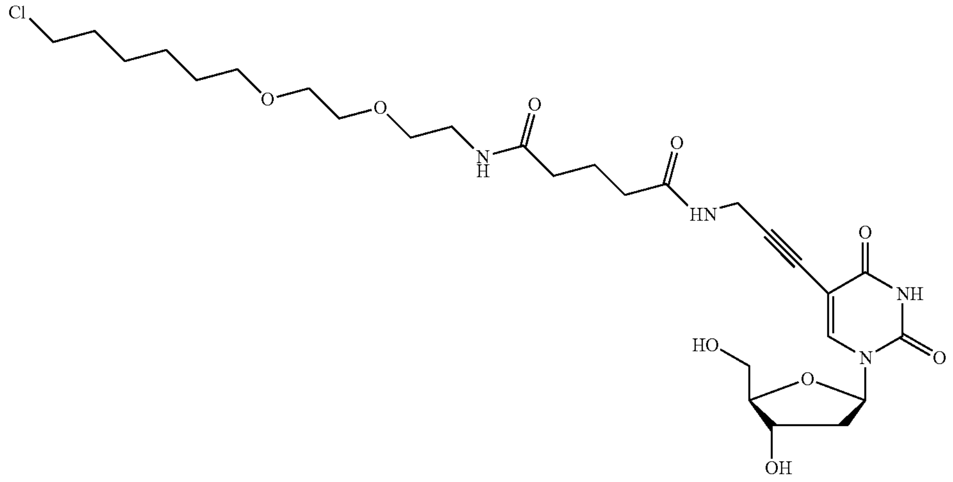
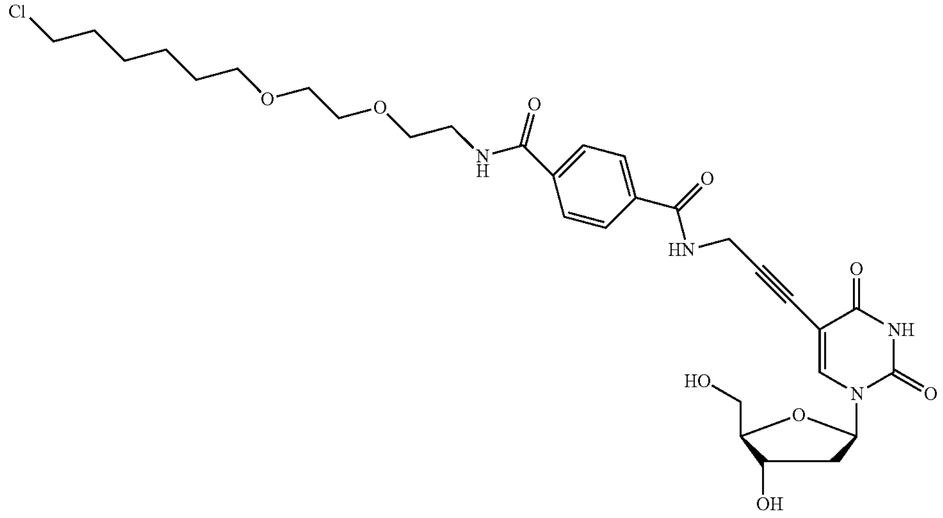
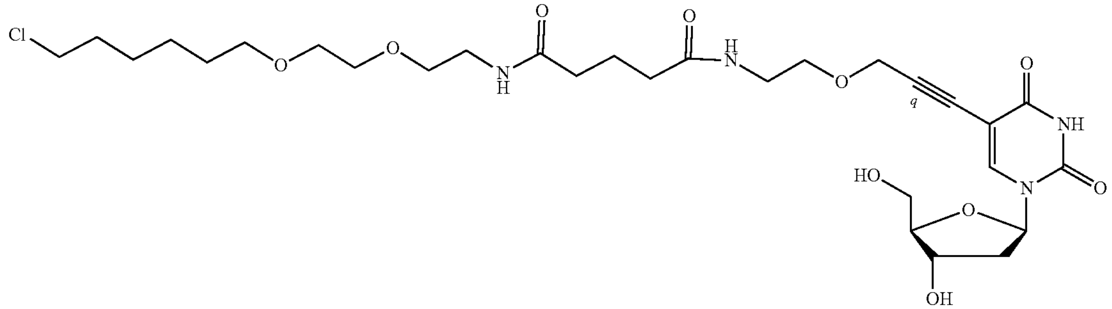
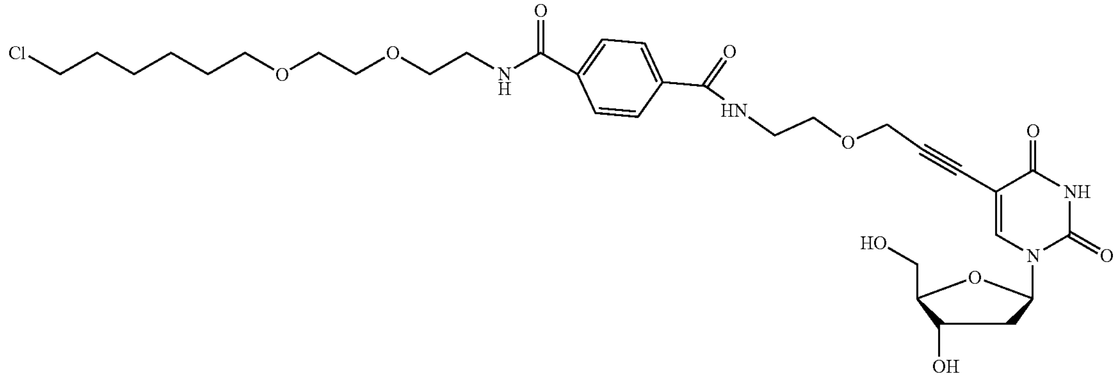

-continued
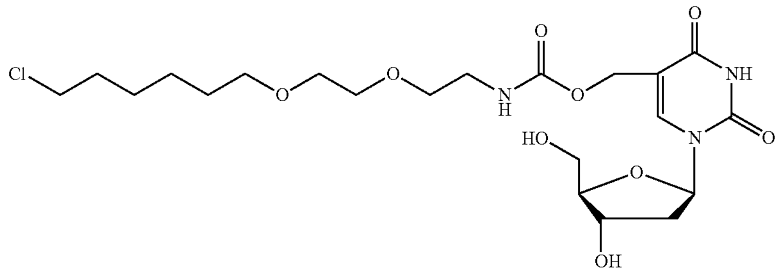
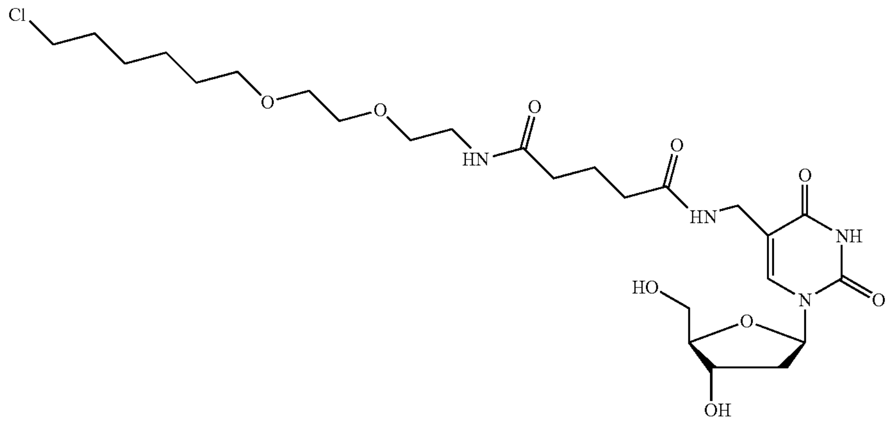
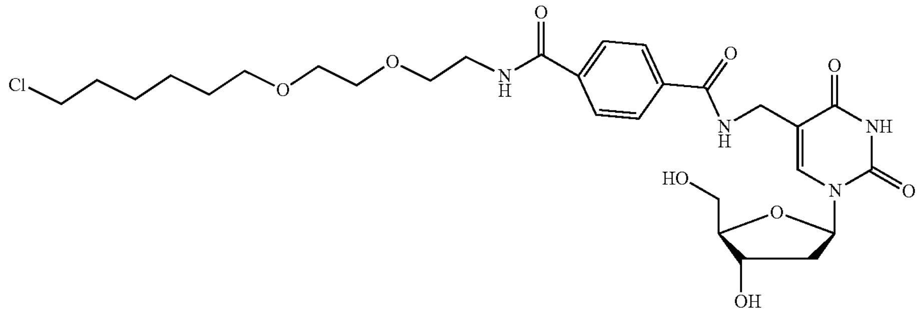
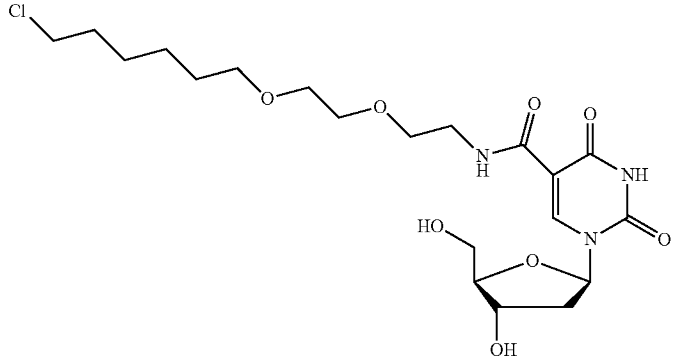

-continued
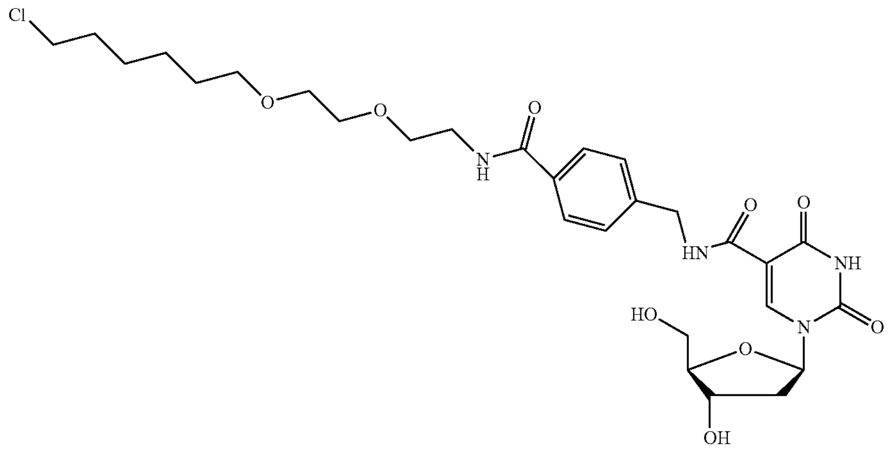
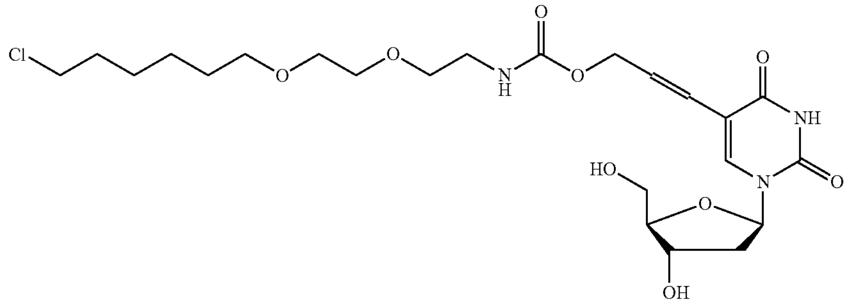
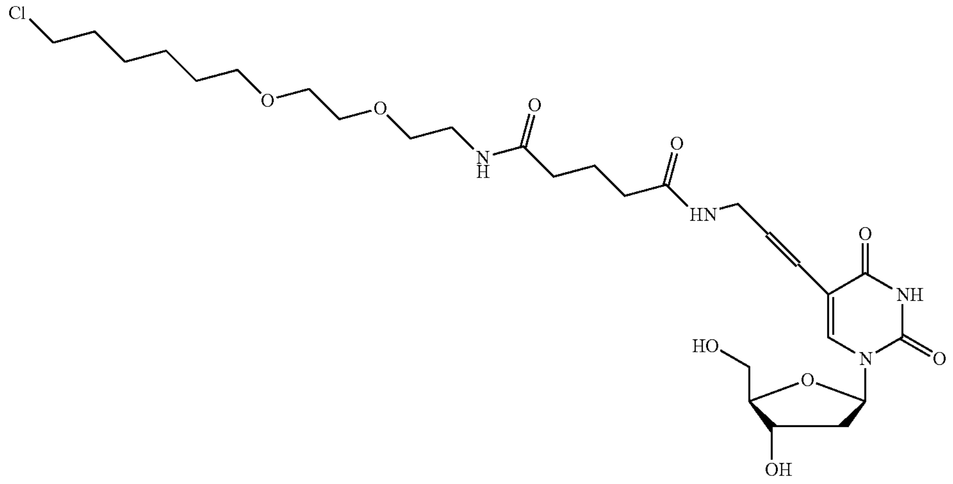

-continued
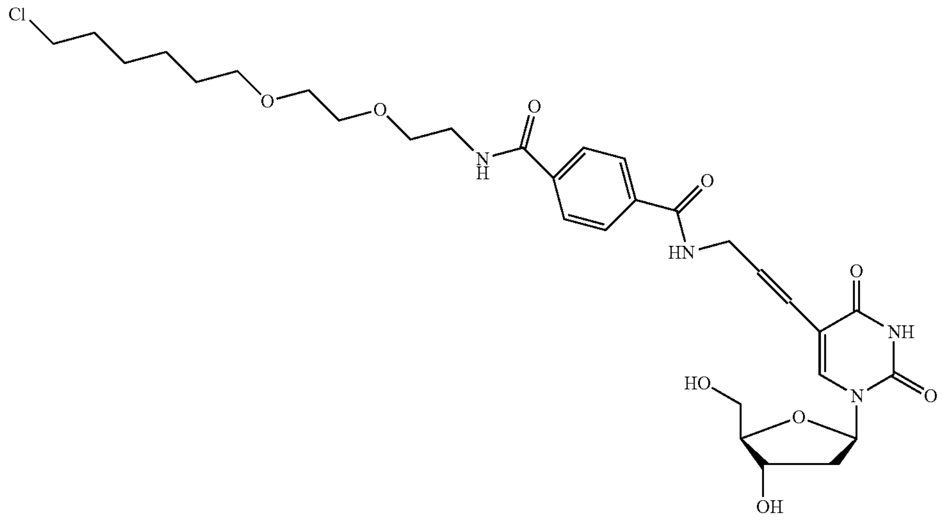
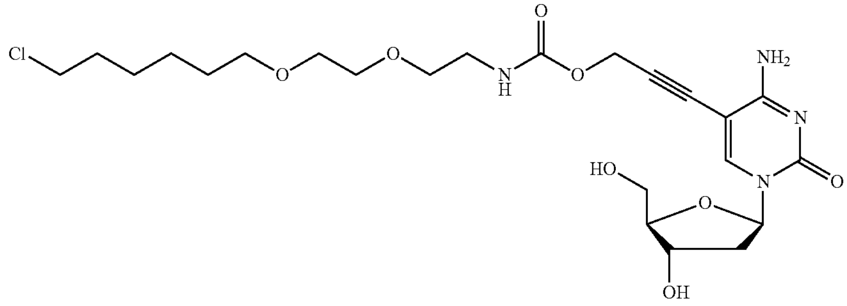
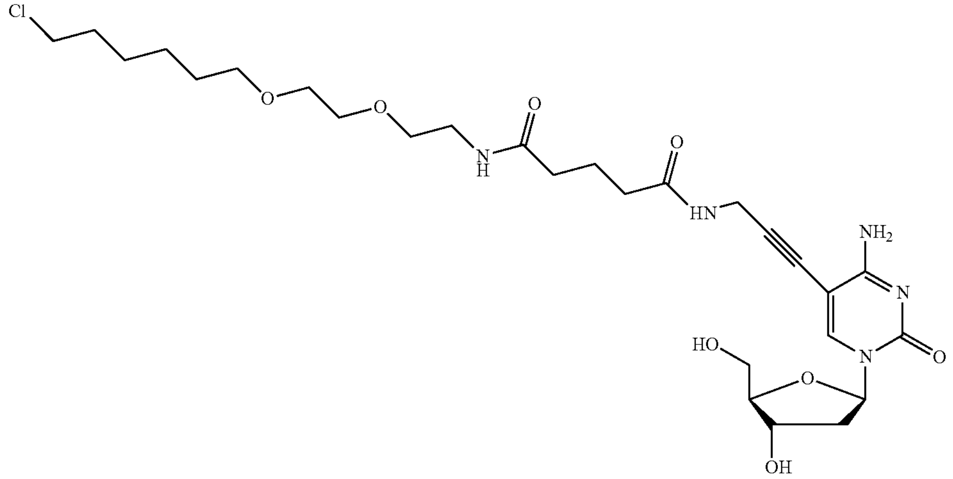

-continued
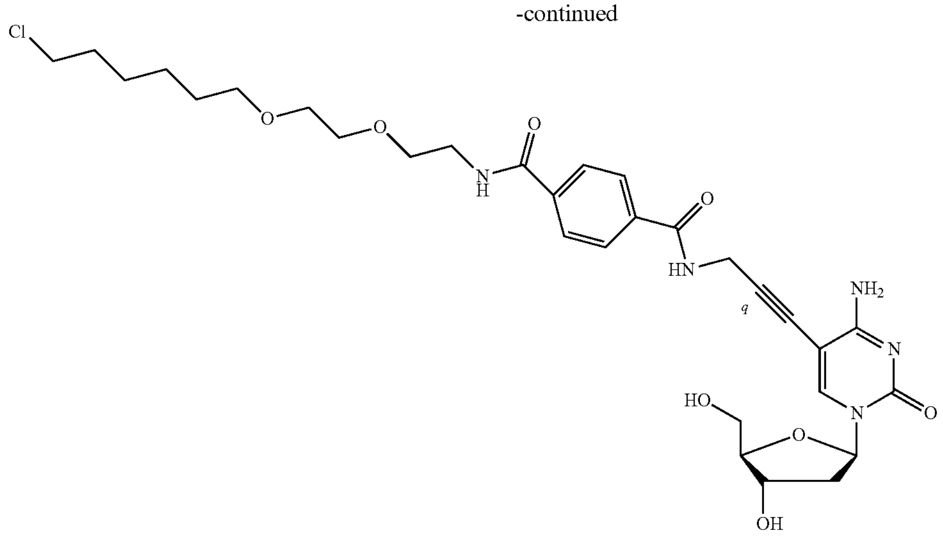
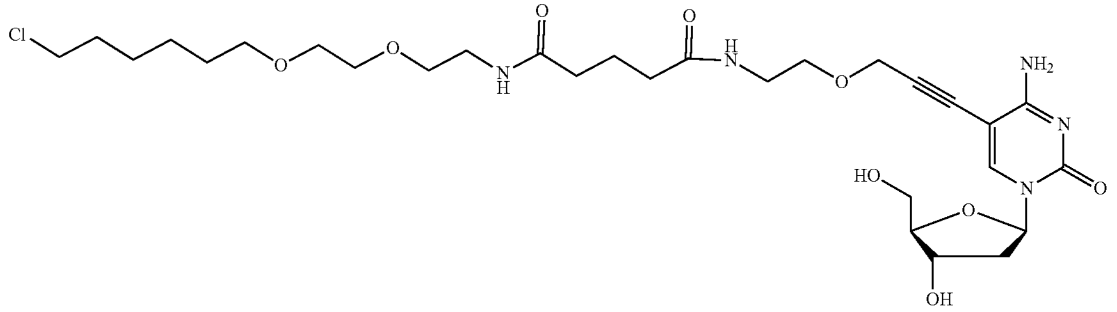
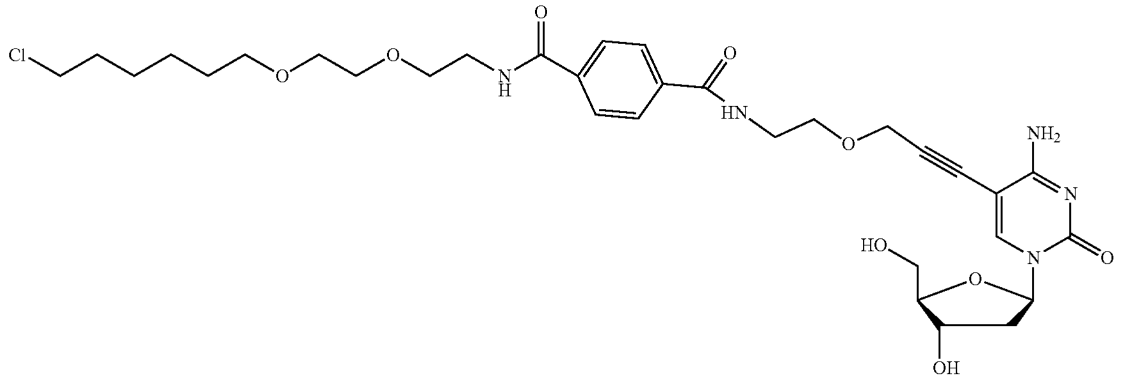
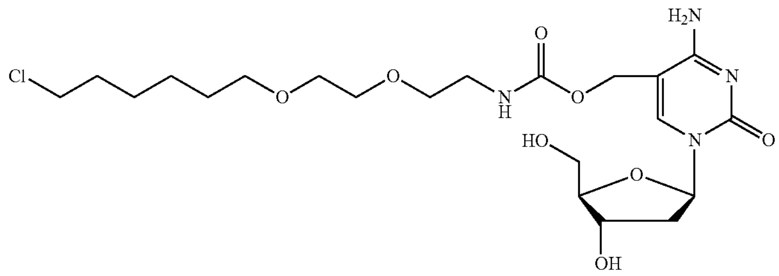

-continued
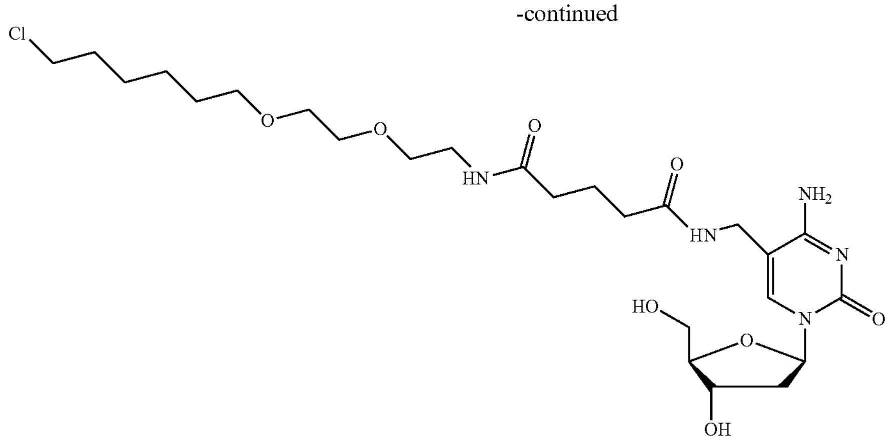
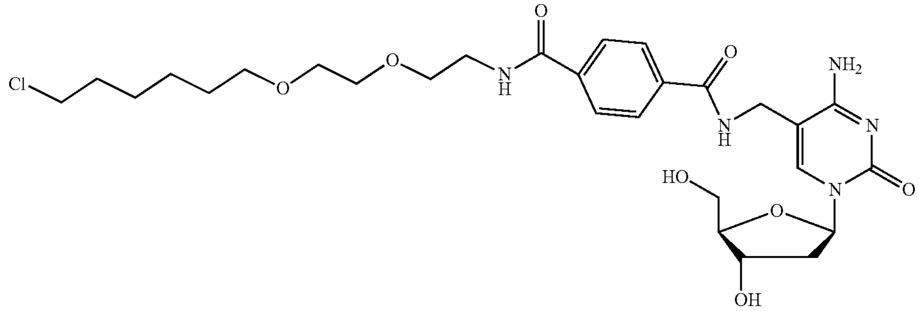
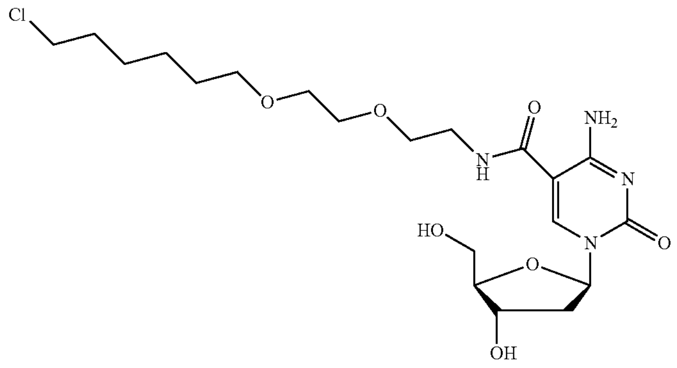
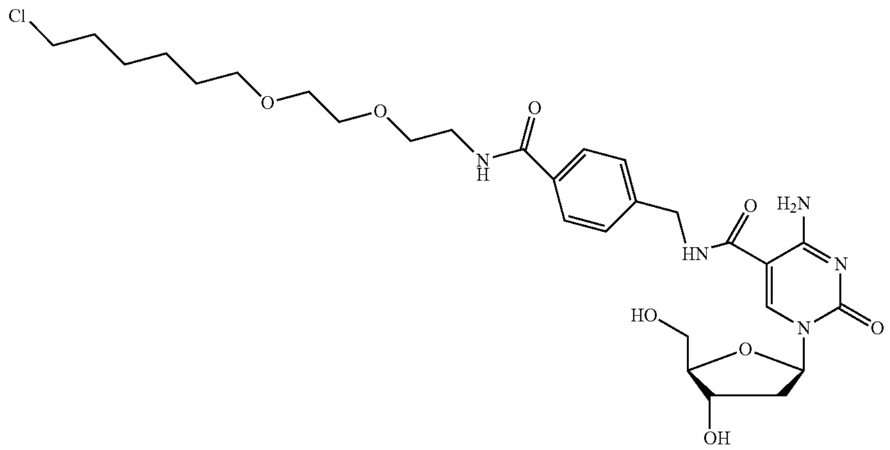

-continued
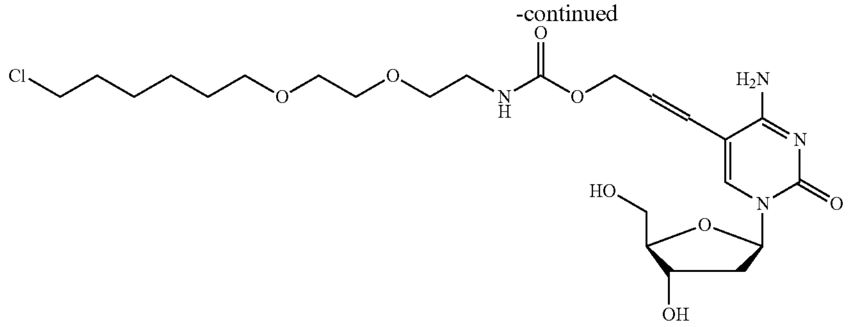
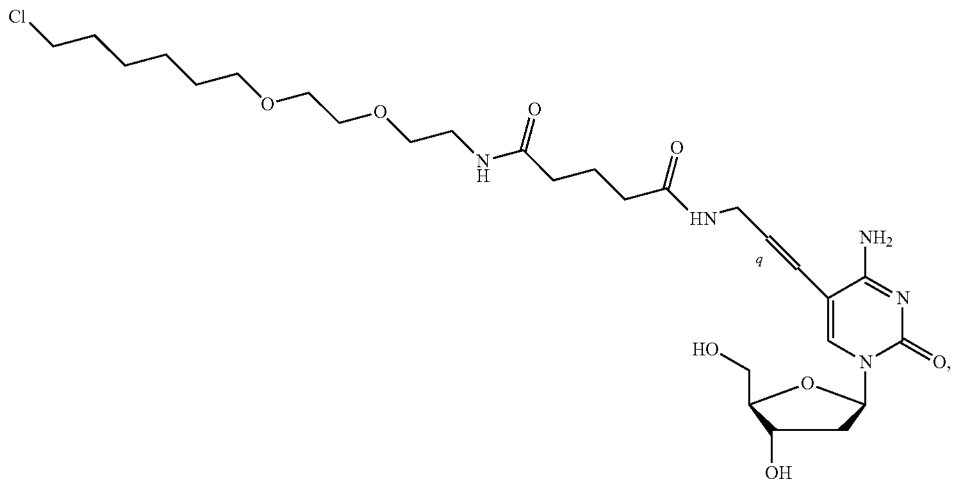
, and
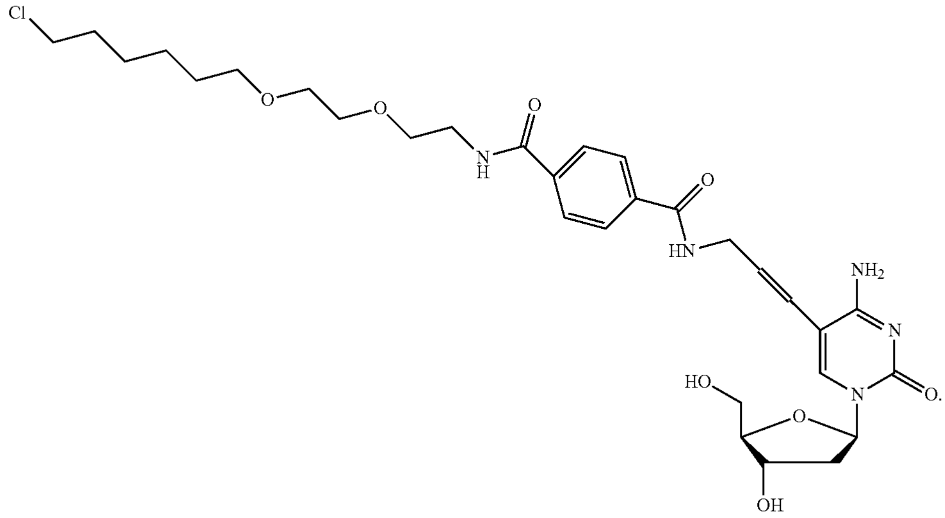
.

In some embodiments, provided herein are compounds of formula (IV):

(IV)

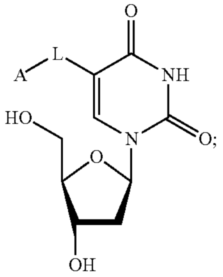

or a salt thereof, wherein: L is a linker; and A is a haloalkyl group. In some embodiments, L comprises one or more groups independently selected from alkylene, alkenylene, alkynylene, arylene, —O—, —NH—, and —C(O)—. In some embodiments, L comprises one or more groups selected from $—CH_2—$, —C≡C—, —C(O)NH—, —OC(O)NH—, $—CH_2CH_2O—$, and phenylene. In some embodiments, L is selected from:

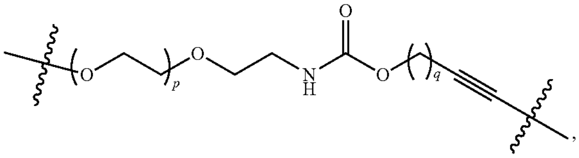

,

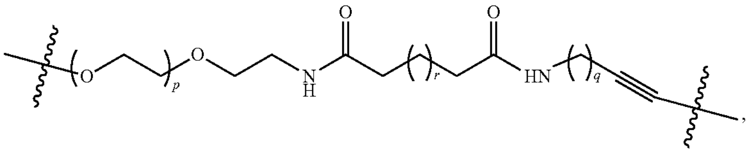

,

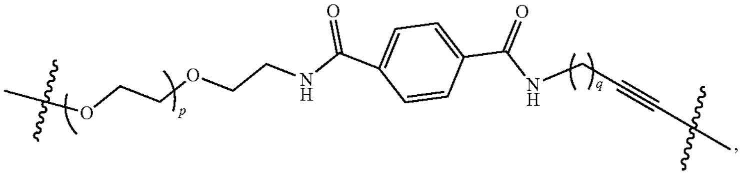

,

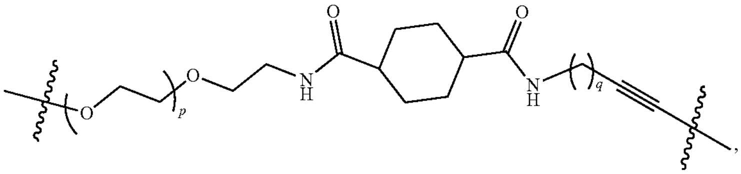

,

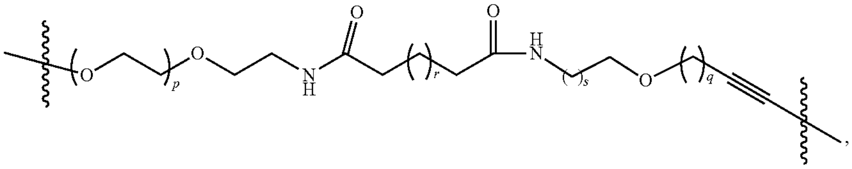

,

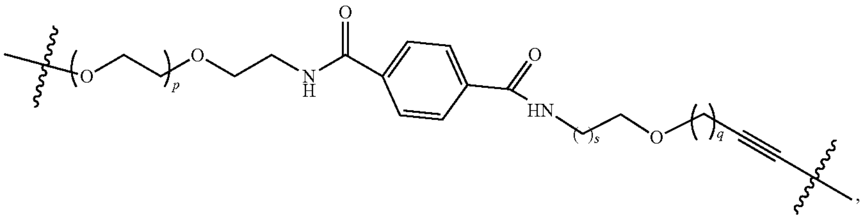

,

-continued
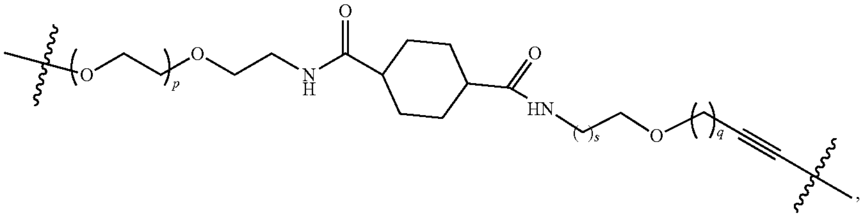,
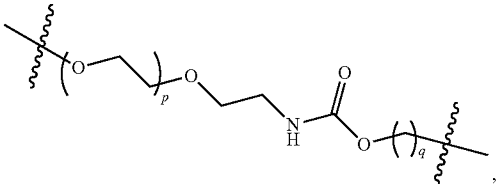, 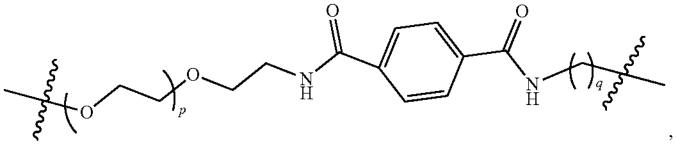,
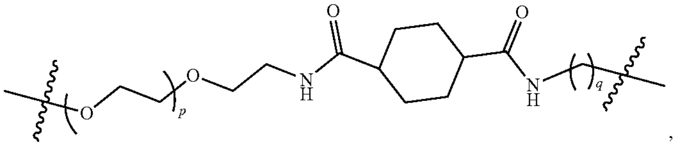, 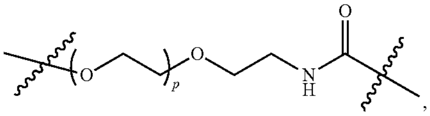,
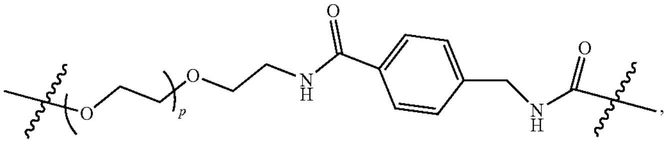,
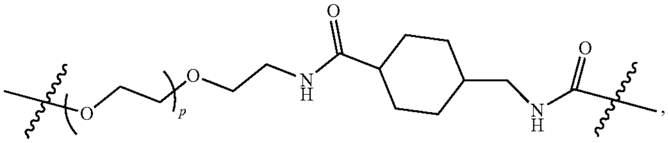,
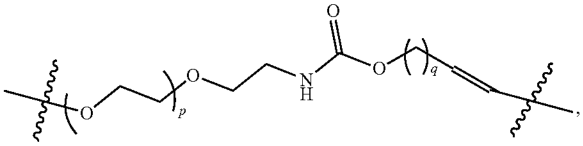,
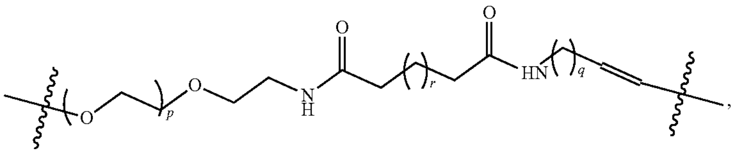,
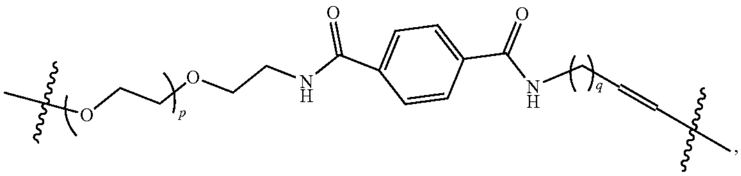, and
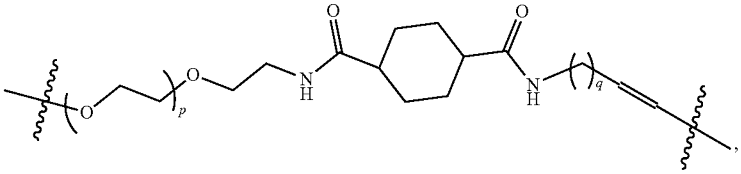, wherein p, q, r, and s are each independently 1-6. In some embodiments, L is selected from:

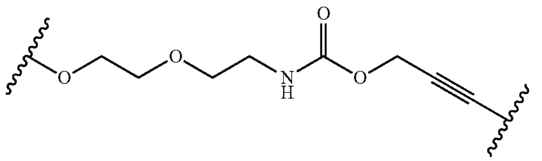

and

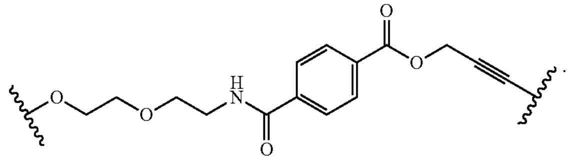

In some embodiments, A is a $C_2$-$C_{12}$ haloalkyl group. In some embodiments, L is C≡C-L', wherein L' is selected from alkyl, cyclic alkyl, alkylene, alkenylene, alkynylene, arylene, —O—, —NH—, —C(O)—, —$(CH_2)_m$—, —CH═CH—, —C≡C—, —C(O)NH—, —OC(O)NH—, —$CH_2CH_2O$—, and —$CH_2O$—, wherein m is 1-6. In some embodiments, A has formula:

—$(CH_2)_n$-X; wherein n is 4, 5, 6, 7, or 8, and X is halo. In some embodiments, n is 6, and X is chloro. In some embodiments, the compound is selected from:

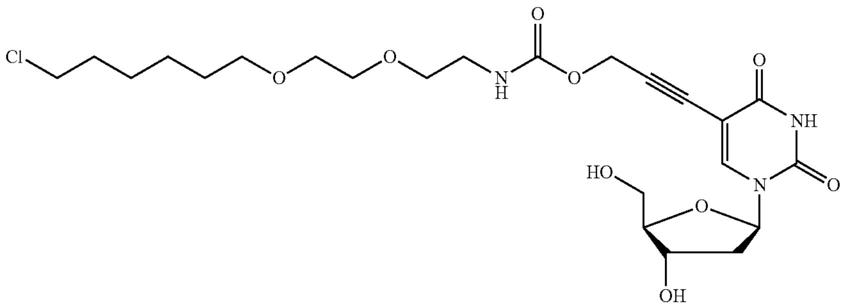

and

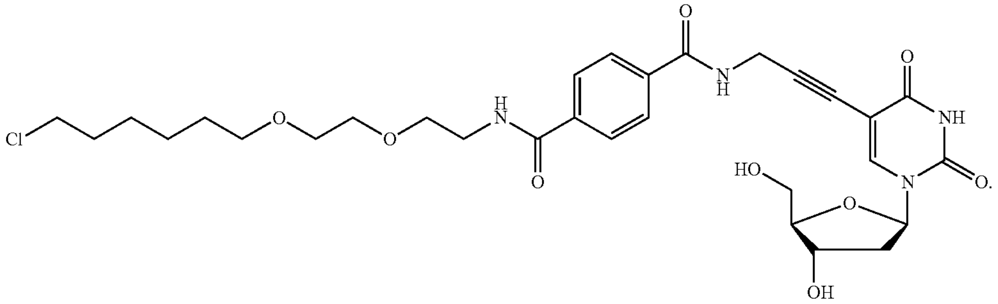

In some embodiments, the compound is selected from:

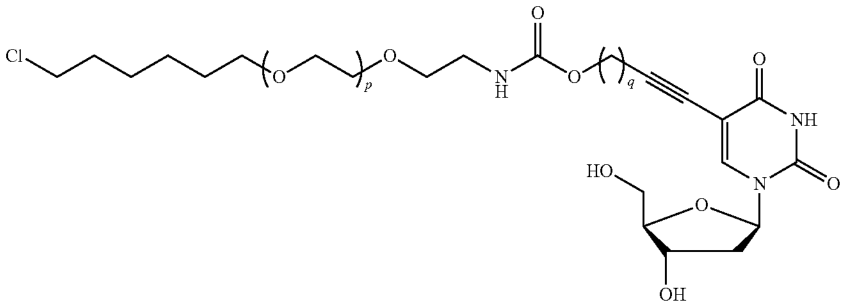

-continued
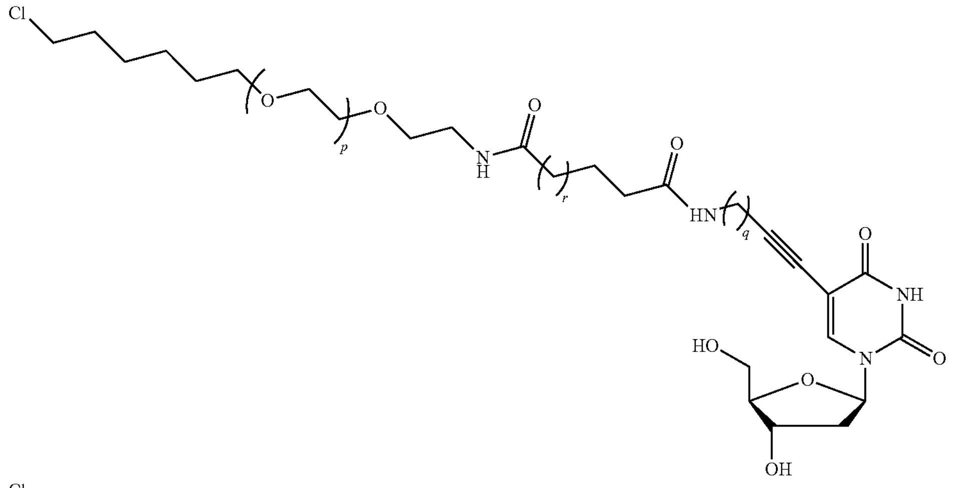
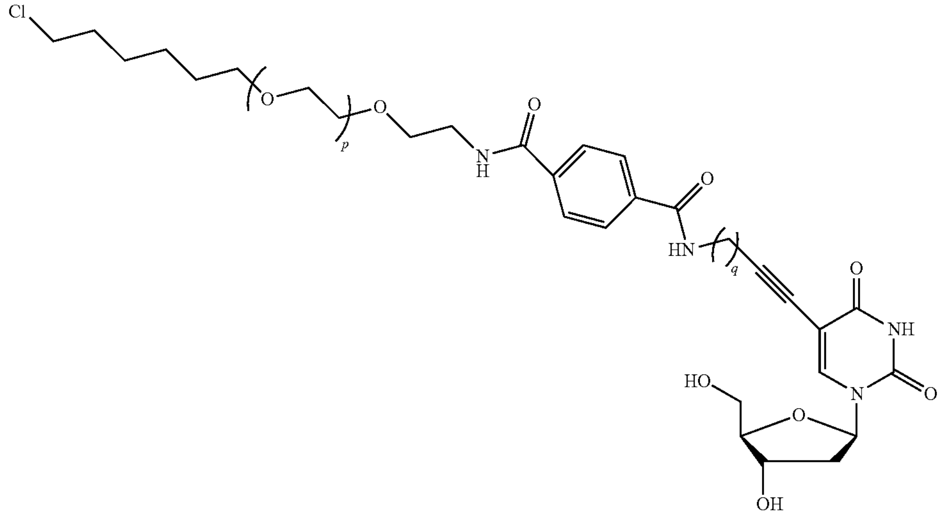
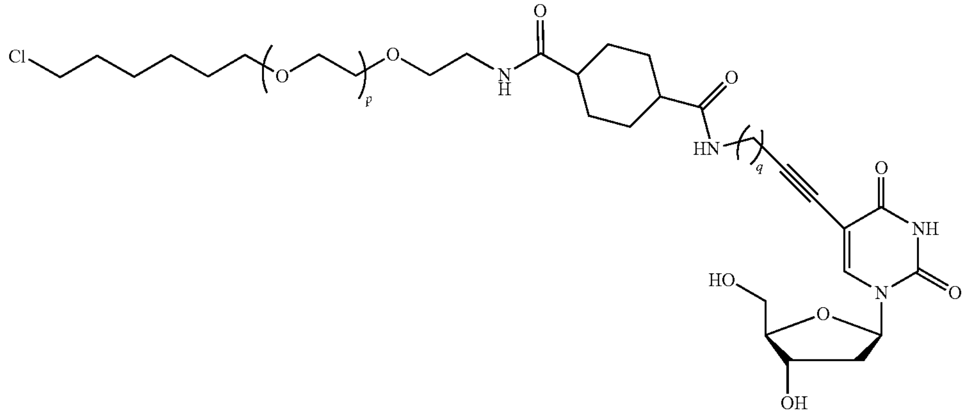
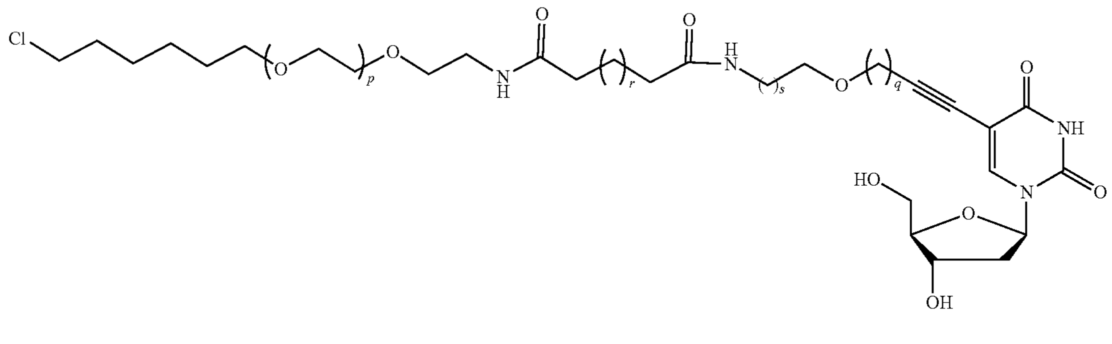

-continued
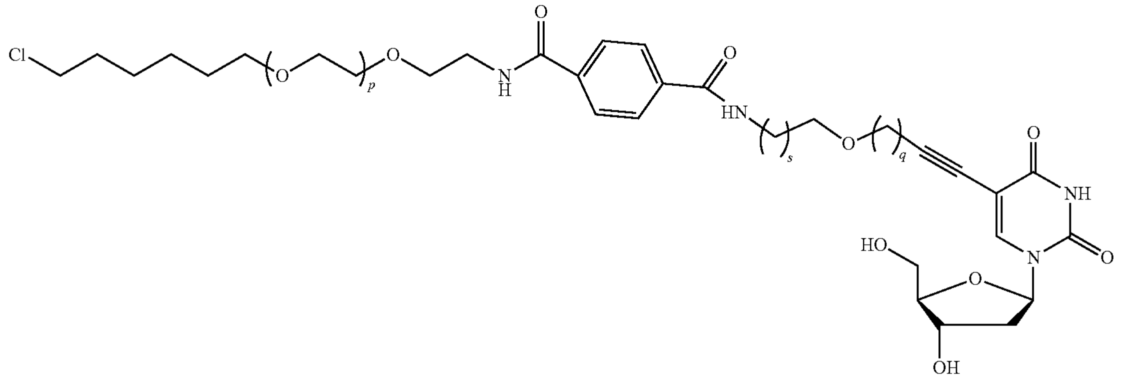
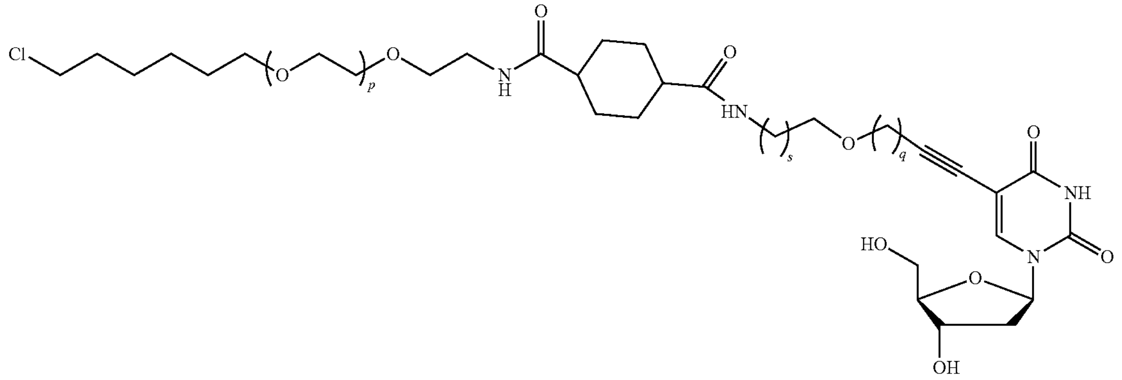
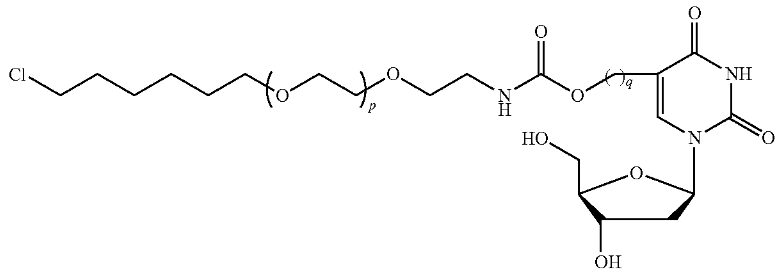
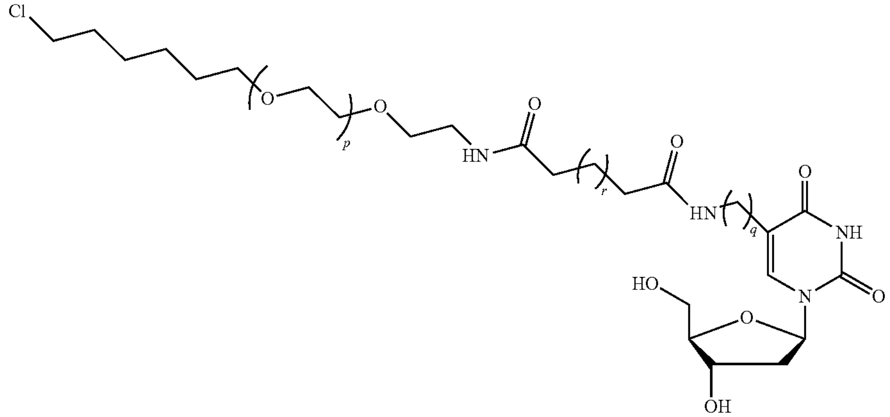

-continued
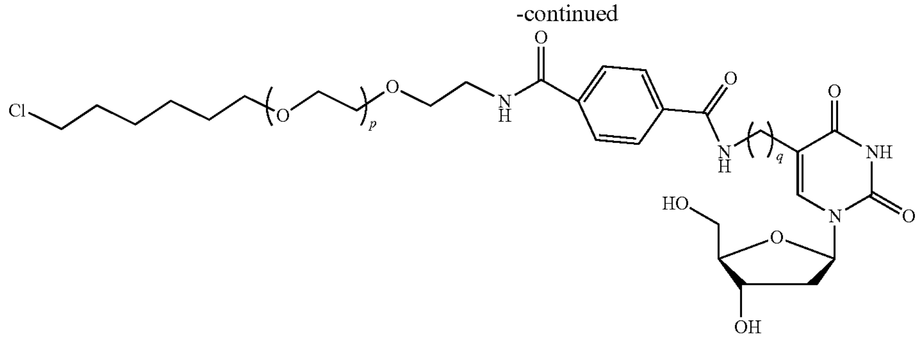
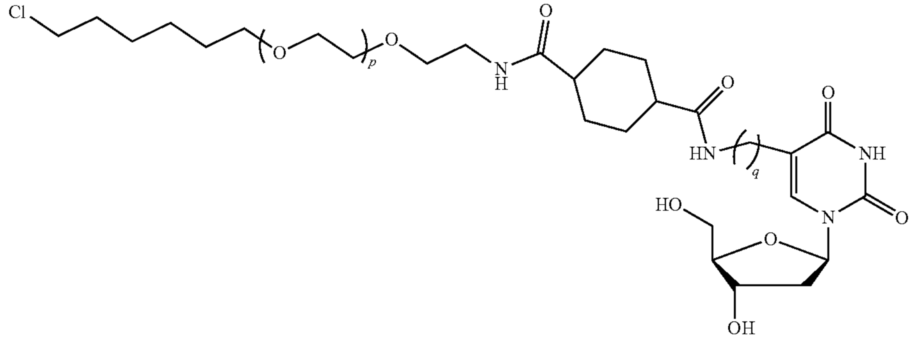
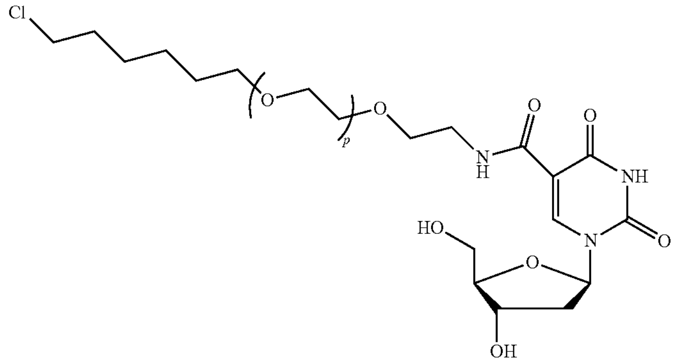
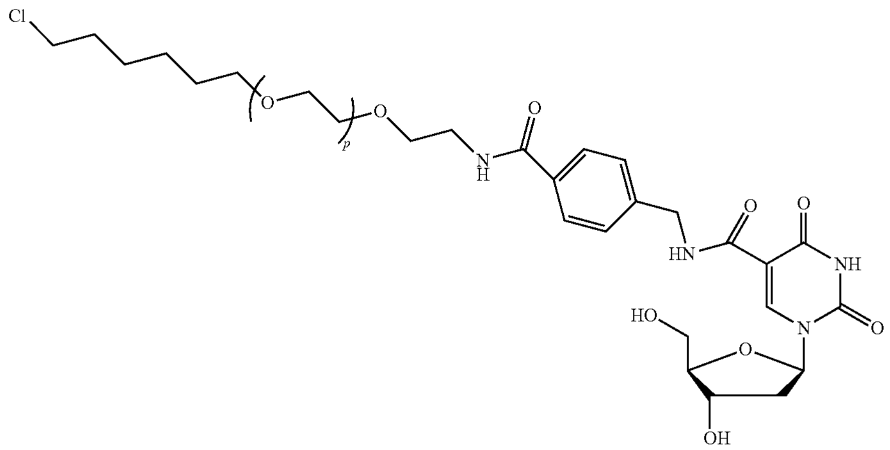

-continued
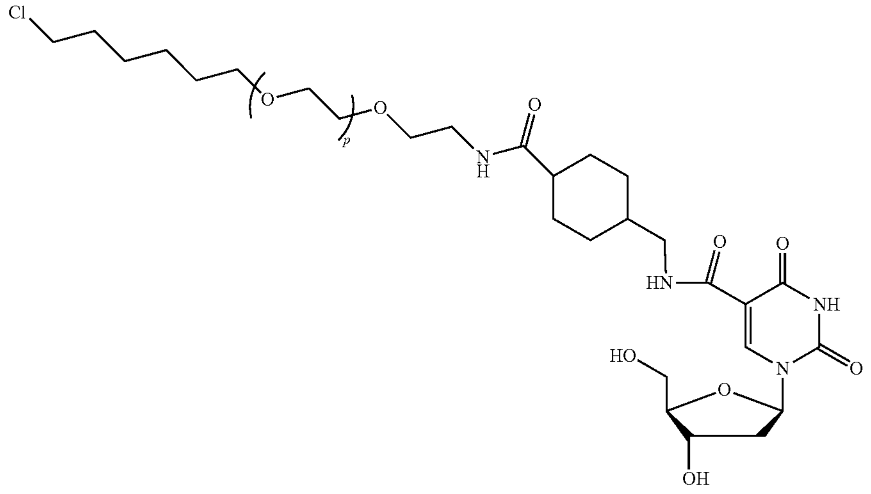
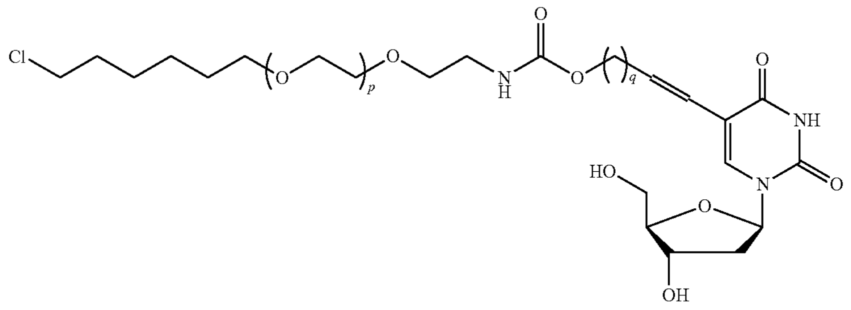
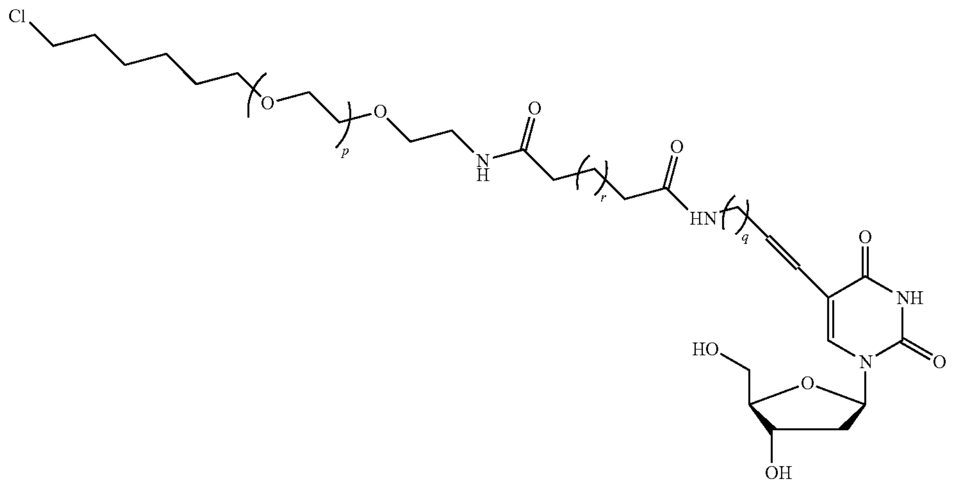

-continued

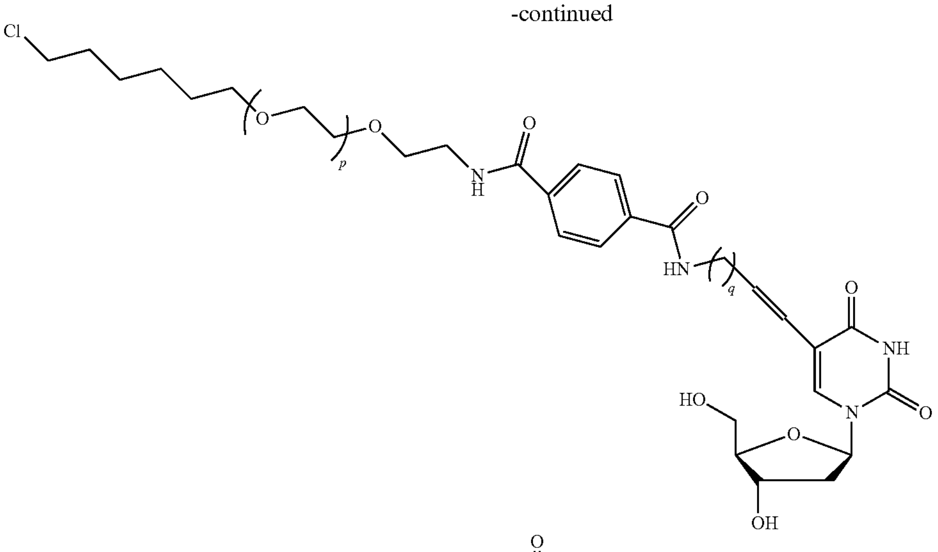

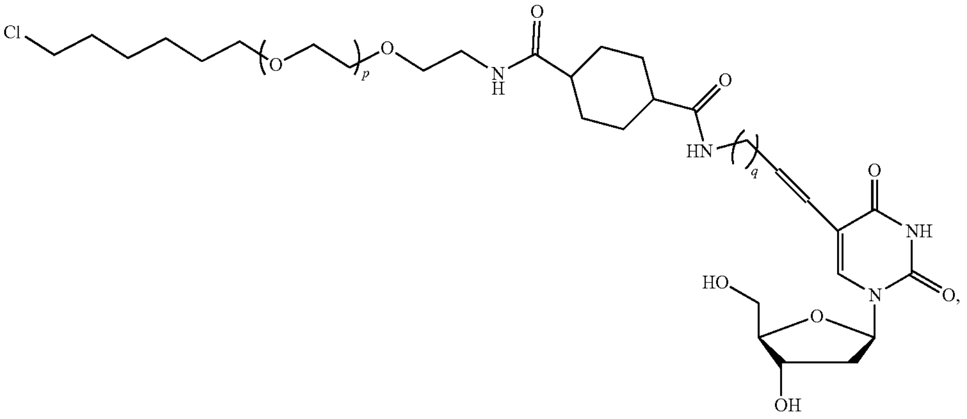

wherein p, q, r, and s are independently 1-6.

In some embodiments, provided herein are polynucleotide chains comprising deoxyadenosine, deoxythymidine, deoxycytidine, deoxyguanosine, and a haloalkyl-modified deoxyuridine described herein. In other embodiments, polynucleotides are provided comprising deoxyadenosine, deoxythymidine, deoxycytidine, deoxyguanosine, and one or more of haloalkyl-modified deoxyuridine, haloalkyl-modified deoxyadenosine, haloalkyl-modified deoxycytidine, and haloalkyl-modified deoxyguanosine.

In some embodiments, provided herein are methods of labeling a nucleic acid comprising including haloalkyl-modified deoxynucleotides described herein with other deoxynucleotides, a template DNA, and DNA polymerase and allowing the DNA polymerase to incorporate the haloalkyl-modified deoxynucleotides described herein and other deoxynucleotides into a newly synthesized labelled nucleic acid.

In some embodiments, provided herein are methods of labeling identifying a nucleic acid within a cell with a haloalkyl group, the method comprising contacting the cell with a haloalkyl-modified deoxynucleoside described herein, and allowing the haloalkyl-modified deoxynucleoside to enter then cell. The cellular machinery then converts the haloalkyl-modified deoxynucleoside into a haloalkyl-modified deoxynucleotide triphosphate, and the haloalkyl-modified deoxynucleotide triphosphate is incorporated into the nucleic acid of the cell during DNA synthesis in place of a portion of the corresponding unmodified nucleotides. In some embodiments, the cell is cultured in media that contains the haloalkyl-modified deoxynucleosides. Embodiments utilizing haloalkyl-modified deoxyuridine are exemplified herein and demonstrate the broader utility of haloalkyl-modified deoxynucleosides in general.

In some embodiments, provided herein are nucleic acids produced by the methods herein (e.g., nucleic acids containing one or more haloalkyl-modified deoxynucleotides). In some embodiments, provided herein are cells comprising a nucleic acid produced by the methods herein.

In some embodiments, provided herein are methods (of detecting a nucleic acid within a cell, monitoring DNA synthesis, monitoring cell proliferation, etc.) comprising: (a) identifying the nucleic acid with a haloalkyl group by the methods herein; (b) lysing the cell to produce a cell lysate comprising the haloalkyl-labelled nucleic acid; (c) contacting the cell lysate with: (i) a first fusion of (A) a first modified dehalogenase enzyme capable of covalently binding the haloalkyl group and (B) a peptide component of a luminescent complex; (ii) a second fusion of (A) a second modified dehalogenase enzyme capable of covalently binding the haloalkyl group and (B) a polypeptide component of the luminescent complex; and (iii) a substrate for the luminescent complex; and (d) detecting luminescence from the luminescent complex, wherein luminescence indicates sufficient density of haloalkyl incorporation of the nucleic acid to allow binding of the first fusion and the second fusion at locations along the nucleic that facilitate formation of the luminescent complex. In some embodiments, the first modified dehalogenase enzyme and the second modified dehalogenase enzyme have at least 70% (e.g., 70%, 75%, 80%, 85%, 90%, 95%, 100%, or ranges therebetween) sequence identity with SEQ ID NO: 16. In some embodiments, the peptide component of the luminescent complex comprises at last 70% (e.g., 70%, 75%, 80%, 85%, 90%, 95%, 100%, or ranges therebetween) sequence identity with SEQ ID NO: 10. In some embodiments, the polypeptide component of the luminescent complex comprises at last 70% (e.g., 70%, 75%, 80%, 85%, 90%, 95%, 100%, or ranges therebetween) sequence identity with SEQ ID NO: 9. In some embodiments, the peptide component of the luminescent complex comprises at last 70% (e.g., 70%, 75%, 80%, 85%, 90%, 95%, 100%, or ranges therebetween) sequence identity with SEQ ID NO: 14. In some embodiments, the polypeptide component of the luminescent complex comprises at last 70% (e.g., 70%, 75%, 80%, 85%, 90%, 95%, 100%, or ranges therebetween) sequence identity with SEQ ID NO: 12. In some embodiments, the substrate for the luminescent complex comprises coelenterazine, furimazine, or a coelenterazine analog or derivative.

In some embodiments, provided herein are methods (of detecting a nucleic acid within a cell, monitoring DNA synthesis, monitoring cell proliferation, etc.) comprising: (a) labeling the nucleic acid with a haloalkyl group by the method herein; (b) expressing within the cell: (i) a first fusion of (e.g., inducing the expression of) (A) a first modified dehalogenase enzyme capable of covalently binding the haloalkyl group and (B) a peptide component of a luminescent complex; (ii) a second fusion of (A) a second modified dehalogenase enzyme capable of covalently binding the haloalkyl group and (B) a polypeptide component of the luminescent complex; (c) contacting the cell with a substrate for the luminescent complex; and (d) detecting luminescence from the luminescent complex, wherein luminescence indicates sufficient density of haloalkyl labeling of the nucleic acid to allow binding of the first fusion and the second fusion at locations along the nucleic that facilitate formation of the luminescent complex. In some embodiments, the first modified dehalogenase enzyme and the second modified dehalogenase enzyme have at least 70% (e.g., 70%, 75%, 80%, 85%, 90%, 95%, 100%, or ranges therebetween) sequence identity with SEQ ID NO: 16. In some embodiments, the peptide component of the luminescent complex comprises at last 70% (e.g., 70%, 75%, 80%, 85%, 90%, 95%, 100%, or ranges therebetween) sequence identity with SEQ ID NO: 10. In some embodiments, the polypeptide component of the luminescent complex comprises at last 70% (e.g., 70%, 75%, 80%, 85%, 90%, 95%, 100%, or ranges therebetween) sequence identity with SEQ ID NO: 9. In some embodiments, the peptide component of the luminescent complex comprises at last 70% (e.g., 70%, 75%, 80%, 85%, 90%, 95%, 100%, or ranges therebetween) sequence identity with SEQ ID NO: 14. In some embodiments, the polypeptide component of the luminescent complex comprises at last 70% (e.g., 70%, 75%, 80%, 85%, 90%, 95%, 100%, or ranges therebetween) sequence identity with SEQ ID NO: 12. In some embodiments, the substrate for the luminescent complex comprises coelenterazine, furimazine, or a coelenterazine analog or derivative.

In some embodiments, provided herein are methods (of detecting a nucleic acid within a cell, monitoring DNA synthesis, monitoring cell proliferation, etc.) comprising: (a) modifying the nucleic acid with a haloalkyl group by the methods herein; (b) lysing the cell to produce a cell lysate comprising the haloalkyl-labelled nucleic acid; (c) contacting the cell lysate with: (i) a fusion of (A) a modified dehalogenase enzyme capable of covalently binding the haloalkyl group and (B) a luminescent protein; and (iii) a substrate for the luminescent complex; and (d) detecting luminescence from the luminescent protein, wherein the luminescence is proportional to the amount of haloalkyl-labeled nucleic acid. In some embodiments, the polypeptide component of the luminescent protein comprises at last 70% (e.g., 70%, 75%, 80%, 85%, 90%, 95%, 100%, or ranges therebetween) sequence identity with SEQ ID NO: 5. In some embodiments, the substrate for the luminescent protein comprises coelenterazine, furimazine, or a coelenterazine analog or derivative. In some embodiments, the first modified dehalogenase enzyme and the second modified dehalogenase enzyme have at least 70% (e.g., 70%, 75%, 80%, 85%, 90%, 95%, 100%, or ranges therebetween) sequence identity with SEQ ID NO: 16.

In some embodiments, provided herein are methods of detecting a nucleic acid within a cell comprising: (a) modifying the nucleic acid with a haloalkyl group by the methods herein; (b) lysing the cell to produce a cell lysate comprising the haloalkyl-labelled nucleic acid; (c) contacting the cell lysate with: (i) a first fusion of (A) a first modified dehalogenase enzyme capable of covalently binding the haloalkyl group and (B) a first peptide component of a luminescent complex; (ii) a second fusion of (A) a second modified dehalogenase enzyme capable of covalently binding the haloalkyl group and (B) a second peptide component of the luminescent complex; (iii) a polypeptide component of the luminescent complex; and (iv) a substrate for the luminescent complex; and (d) detecting luminescence from the luminescent complex, wherein luminescence indicates sufficient density of haloalkyl labeling of the nucleic acid to allow binding of the first fusion and the second fusion at locations along the nucleic that facilitate formation of the luminescent complex. In some embodiments, the first modified dehalogenase enzyme and the second modified dehalogenase enzyme have at least 70% sequence identity with SEQ ID NO: 16. In some embodiments, the first peptide component of the luminescent complex comprises at last 70% (e.g., 70%, 75%, 80%, 85%, 90%, 95%, 100%, or ranges therebetween) sequence identity with SEQ ID NO: 13. In some embodiments, the second peptide component of the luminescent complex comprises at last 70% (e.g., 70%, 75%, 80%, 85%, 90%, 95%, 100%, or ranges therebetween) sequence identity with SEQ ID NO: 15. In some embodiments, the polypeptide component of the luminescent complex comprises at last 70% (e.g., 70%, 75%, 80%, 85%, 90%, 95%, 100%, or ranges therebetween) sequence identity with SEQ ID NO: 12. In some embodiments, the substrate for the luminescent complex comprises coelenterazine or furimazine.

In some embodiments, provided herein are methods of detecting haloalkyl-labelled nucleic acid within a cell comprising: (a) lysing the cell to produce a cell lysate comprising the haloalkyl-labelled nucleic acid; (b) contacting the cell lysate with (i) a modified dehalogenase capable of covalently binding the haloalkyl group and (ii) a reporter capable of producing a detectable signal; (c) allowing the modified dehalogenase to bind to the haloalkyl groups on the nucleic acid; and (d) detecting the detectable signal from the reporter. In some embodiments, the reporter is a luciferase (e.g., NANOLUC, Firefly luciferase, Renilla luciferase, etc.), fluorophore (e.g., TAMRA, BODIPY, FAM, etc.), fluorescent protein (e.g., GFP, CFP, YFP, variants thereof, etc.), or a detectable enzyme (e.g., horseradish peroxidase, alkaline phosphatase, beta-galactosidase, acetylcholinesterase, etc.). In some embodiments, methods further comprise a step between steps (c) and (d) of washing away reporter tethered to modified dehalogenase that is not bound to the haloalkyl-labelled nucleic acid.

In some embodiments, provided herein are methods of detecting haloalkyl-labelled nucleic acid within a cell comprising: (a) lysing the cell to produce a cell lysate comprising the haloalkyl-labelled nucleic acid; (b) contacting the cell lysate with (i) a first fusion of (A) a modified dehalogenase capable of covalently binding the haloalkyl group and (B) a first component of a reporter complex, and (ii) a second fusion of (A) a modified dehalogenase capable of covalently binding the haloalkyl group and (B) a second component of a reporter complex, wherein the detectable complex is capable of producing a detectable signal upon the first component being brought in contact or physical proximity with the second component; (c) allowing the modified dehalogenase to bind to the haloalkyl groups on the nucleic acid; and (d) detecting the detectable signal from the reporter complex. In some embodiments, the reporter complex is a split luciferase (e.g., NANOBIT), a split fluorescent protein (e.g., split GFP), or a split detectable enzyme. In some embodiments, "split" refers to a reporter that is present as two or more complementary fragments; when the components of the complex are brought together, a greater detectable signal is produced than that of the individual components.

In some embodiments, provided herein are methods of detecting haloalkyl-labelled nucleic acid within a cell by BRET, comprising: (a) lysing the cell to produce a cell lysate comprising the haloalkyl-labelled nucleic acid; (b) contacting the cell lysate with (i) (A) a modified dehalogenase capable of covalently binding the haloalkyl group tethered to (B) a reporter capable of emitting light at a first wavelength, and (ii) (A) a modified dehalogenase capable of covalently binding the haloalkyl group and (B) fluorophore with an excitation spectrum that overlaps the first wavelength and an emission spectrum; (c) allowing the modified dehalogenase to bind to the haloalkyl groups on the nucleic acid; and (d) detecting a wavelength within the emission spectrum of the fluorophore. In some embodiments, the reporter is a luciferase and emits light at the first wavelength upon contacting a substrate. In some embodiments, methods further comprise contacting the cell lysate with the substrate for the luciferase. In some embodiments, the reporter is a fluorescent protein and emits light at the first wavelength upon exposure of the fluorescent protein to a wavelength within the excitation spectrum of the fluorescent protein. In some embodiments, methods further comprise exposing the cell lysate to a wavelength within the excitation spectrum of the fluorescent protein. In some embodiments, the amount of luminescence (or other reporter signal) detected in the methods herein is proportional to the amount of haloalkyl nucleotides incorporated into a newly synthesized nucleic acid. In some embodiments, the amount of haloalkyl nucleotides incorporated is proportional to the rate of DNA synthesis within the cell. In some embodiments, the rate of DNA synthesis within the cell is proportional to the rate of cellular replication. In some embodiments, detecting comprises monitoring the luminescence (or other reporter signal) over time. In some embodiments, methods further comprise exposing the cell to a stimulus and monitoring the effect of the stimulus on luminescence (or other reporter signal). In some embodiments, the stimulus results in modification (e.g., increase or decrease) in the rate of cell death, cellular replication, and/or DNA synthesis.

DEFINITIONS

Figure 1:
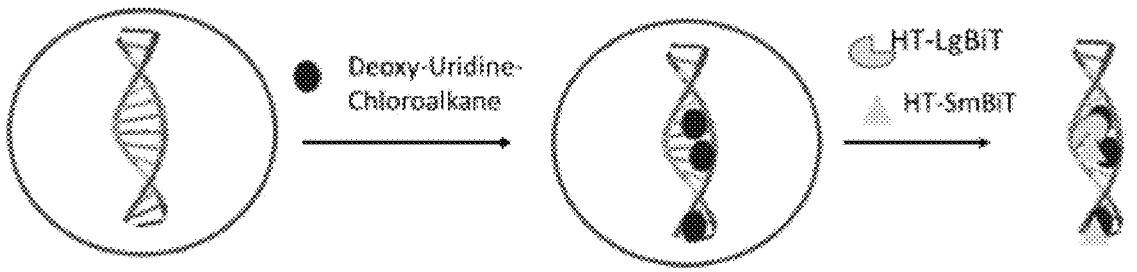
FIG. 1. Schematic depicting the steps of an exemplary method described herein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)", "include(s)", "having", "has", "can", "contain(s)" and variants thereof, as used herein, are intended to be open-ended transitional phrases, terms, or words that do not preclude the possibility of additional acts or structures. The singular forms "a", "and" and "the" include plural references unless the context clearly dictates otherwise. Many embodiments herein are described using open "comprising" language. Such embodiments encompass multiple closed "consisting of" and/or "consisting essentially of" embodiments, which may alternatively be claimed or described using such language. The present disclosure also contemplates other embodiments "comprising," "consisting of" and "consisting essentially of," the embodiments or elements presented herein, whether explicitly set forth or not.

For the recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "alkyl" means a straight or branched saturated hydrocarbon chain containing from 1 to 16 carbon atoms ($C_1$-$C_{16}$ alkyl), for example 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term “alkylene” refers to a divalent group derived from a straight or branched chain hydrocarbon of 1 to 16 carbon atoms ($C_1$-$C_{16}$ alkylene), for example, 1 to 10 carbon atoms ($C_1$-$C_{10}$ alkylene), or 1 to 6 carbon atoms ($C_1$-$C_6$ alkylene). Representative examples of alkylene include, but are not limited to, $-CH_2-$, $-CH_2CH_2-$, $-CH(CH_3)-$, $-CH_2CH_2CH_2-$, $-CH_2CH(CH_3)-$, $-CH_2CH_2CH_2CH_2-$, $-CH_2CH(CH_3)CH_2-$, $-CH_2CH_2CH(CH_3)-$, $-CH_2CH_2CH_2CH_2CH_2-$, $-CH_2CH(CH_3)CH_2CH_2-$, $-CH(CH_3)CH_2CH_2CH_2-$, $-CH_2CH_2CH_2CH_2CH_2CH_2-$, $-CH_2CH_2CH(CH_3)CH_2CH_2-$, $-CH_2CH(CH_3)CH_2CH_2CH_2-$, and $-CH(CH_3)CH_2CH_2CH_2CH_2-$.

As used herein, the term “alkenyl” refers to a straight or branched hydrocarbon chain containing from 2 to 16 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term “alkenylene” refers to a divalent group derived from a straight or branched chain hydrocarbon of 2 to 16 carbon atoms and containing at least one carbon-carbon double bond. Representative examples of alkenylene include, but are not limited to, $-CH{=}CH-$, $-CH{=}CHCH_2-$, and $-CH_2CH{=}CHCH_2-$.

As used herein, the term “alkynyl” refers to a straight or branched hydrocarbon chain containing from 2 to 16 carbon atoms and containing at least one carbon-carbon triple bond. Representative examples of alkynyl include, but are not limited to, ethynyl, propynyl, and butynyl.

As used herein, the term “alkynylene” refers to a divalent group derived from a straight or branched chain hydrocarbon of 2 to 16 carbon atoms and containing at least one carbon-carbon double bond. Representative examples of alkynylene include, but are not limited to, $-C{\equiv}C-$, $-C{\equiv}CCH_2-$, and $-CH_2C{\equiv}CCH_2-$.

As used herein, the term “aryl” refers to a phenyl group or a bicyclic or tricyclic aromatic fused ring system. Bicyclic-fused ring systems are exemplified by a phenyl group appended to the parent molecular moiety and fused to a phenyl group. Tricyclic-fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl and phenanthrenyl.

As used herein, the term “arylene” refers to a divalent aryl group, e.g., a phenylene group (e.g., 1,2-phenylene, 1,3-phenylene, and 1,4-phenylene).

As used herein, the terms “halogen” and “halo” mean F, Cl, Br, or I.

As used herein, the term “haloalkyl” means an alkyl group, as defined herein, in which one or more hydrogen atoms are replaced by a halogen. For example, one, two, three, four, five, six, seven, or eight hydrogen atoms can be replaced by a halogen, or all hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, 2,2,2-trifluoroethyl, perfluoroethyl, 2-fluoro-2-methylpropyl, 3,3,3-trifluoropropyl, 4-chlorobutyl, 5-chloropentyl, 6-chlorohexyl, 7-chloroheptyl, and 8-chlorooctyl.

Where substituent groups are specified by their conventional chemical formulae, written from left to right, they are intended encompass substituents resulting from writing the structure from right to left, e.g., $-CH_2CH_2O-$ also recites $-OCH_2CH_2-$, $-C(O)NH-$ also recites $-NHC(O)-$, and $-OC(O)NH-$ also recites $-NHC(O)O-$.

As used herein, in chemical structures the indication:

represents a point of attachment of one moiety to another moiety (e.g., a substituent group to the core compound).

“Bioluminescence” refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into an unstable form by the bioluminescent entity; the substrate subsequently emits light.

“Complementary” refers to the characteristic of two or more structural elements (e.g., peptide, polypeptide, nucleic acid, small molecule, etc.) of being able to hybridize, dimerize, or otherwise form a complex with each other. For example, a “complementary peptide and polypeptide” are capable of coming together to form a complex. Complementary elements may require assistance to form a complex (e.g., from interaction elements), for example, to place the elements in the proper conformation for complementarity, to co-localize complementary elements, to lower interaction energy for complementation, etc.

“Complex” refers to an assemblage or aggregate of molecules (e.g., peptides, polypeptides, etc.) in direct and/or indirect contact with one another. In one aspect, “contact,” or more particularly, “direct contact” means two or more molecules are close enough so that attractive noncovalent interactions such as Van der Waal forces, hydrogen bonding, ionic, and hydrophobic interactions, and the like dominate the interaction of the molecules. In such an aspect, a complex of molecules (e.g., a peptide and polypeptide) is formed under assay conditions such that the complex is thermodynamically favored (e.g., compared to a non-aggregated, or non-complexed, state of its component molecules). As used herein, the term “complex”, unless described as otherwise, refers to the assemblage of two or more molecules (e.g., peptides, polypeptides, or a combination thereof).

“Fragment” refers to a peptide or polypeptide that results from dissection or “fragmentation” of a larger whole entity (e.g., protein, polypeptide, enzyme, etc.), or a peptide or polypeptide prepared to have the same sequence as such. Therefore, a fragment is a subsequence of the whole entity (e.g., protein, polypeptide, enzyme, etc.) from which it is made and/or designed. A peptide or polypeptide that is not a subsequence of a preexisting whole protein is not a fragment (e.g., not a fragment of a preexisting protein). A peptide or polypeptide that is “not a fragment of a preexisting bioluminescent protein" is an amino acid chain that is not a subsequence of a protein (e.g., natural or synthetic) that: (1) was in physical existence prior to design and/or synthesis of the peptide or polypeptide, and (2) exhibits substantial bioluminescent activity.

"Cell impermeable" as used herein refers to a compound or moiety that is not capable of passing through a cell membrane to the extent that an effective amount of the compound or moiety is intracellularly delivered.

"Cell permeable" as used herein refers to a compound or moiety that is capable of passing through a cell membrane to the extent that an effective amount of the compound is intracellularly delivered.

"Coelenterazine" as used herein refers to naturally-occurring ("native") coelenterazine. As used herein, the term "coelenterazine analog" or "coelenterazine derivative" refers to synthetic (e.g., derivative or variant) and natural analogs thereof, including furimazine, coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl coelenterazine, in addition to those disclosed in WO 2003/040100; U.S. application Ser. No. 12/056,073 (paragraph [0086]); U.S. Pat. No. 8,669,103; WO 2012/061529, U.S. Pat. Pub. 2017/0233789 and U.S. Pat. Pub. 2018/0030059; the disclosures of which are incorporated by reference herein in their entireties. In some embodiments, coelenterazine analogs include pro-substrates such as, for example, those described in U.S. application Ser. No. 12/056,073; U.S. Pub. No. 2012/0707849; U.S. Pub. No. 2014/0099654; herein incorporated by reference in their entireties.

"Peptide" and "polypeptide" as used herein, and unless otherwise specified, refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

"Sample", "test sample", "specimen", "sample from a subject", and "patient sample" as used herein may be used interchangeable and may be a sample of blood, such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Subsequence" refers to peptide or polypeptide that has 100% sequence identify with another, larger peptide or polypeptide. The subsequence is a perfect sequence match for a portion of the larger amino acid chain.

"Substantially" as used herein means that the recited characteristic, parameter, and/or value need not be achieved exactly, but that deviations or variations, including for example, tolerances, measurement error, measurement accuracy limitations and other factors known to skill in the art, may occur in amounts that do not preclude the effect the characteristic was intended to provide. A characteristic or feature that is substantially absent (e.g., substantially non-luminescent) may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic (e.g., luminescent intensity of a bioluminescent protein or bioluminescent complex).

DETAILED DESCRIPTION

Provided herein are reagents and methods for incorporating modified nucleosides into DNA and detecting DNA synthesis. In particular haloalkyl-modified nucleotides are provided for incorporation into nucleic acids for detection by bioluminescent binding agents.

In some embodiments, provided herein is the use of haloalkyl-modified nucleoside reagents (e.g., haloalkyl-modified deoxyuridne, haloalkyl-modified deoxy cytidine, etc.) in conjunction with reporter agents (e.g., comprising a modified dehalogenase that binds haloalkyl groups (e.g., HALOTAG) and a detectable reporter element (e.g., NANOLUC, NANOBIT, and/or NANOTRIP technology) to detect DNA synthesis. In some embodiments, haloalkyl-modified nucleosides present in growth media are capable of entering cells. Within the cells, the cellular machinery converts the haloalkyl-modified deoxynucleosides into haloalkyl-modified deoxynucleotide triphosphates. The haloalkyl-modified deoxynucleotide triphosphates are then incorporated into newly synthesized DNA in the dividing (proliferating) cells. When cells are cultured in medium that contains a haloalkyl-modified nucleosides (e.g., deoxyuridine-chloroalkane, deoxyguanosine bromoalkene, etc.), the nucleotide analog enters the cells, is converted into nucleotide triphosphate analogs, and is incorporated in newly synthesized DNA at significant frequency. For example, haloalkyl-modified deoxyuridine (as described herein) present in growth media, is capable of entering cells. The cells convert the haloalkyl-modified deoxyuridine into haloalkyl-modified uridine-5'-triphosphate. In the case of uridine, the haloalkyl-modified uridine-5'-triphosphateis incorporated into the newly synthesized DNA of proliferating cells in place of a portion of deoxythymidine triphosphate. After removing the haloalkyl-modified nucleoside-containing medium (e.g., deoxyuridine-chloroalkane containing medium), cells are lysed, and the incorporation of the modified nucleosides (e.g., deoxy-uridine-chloroalkane) is detected using fusions of a modified dehalogenase that covalently binds to haloalkyl substrates (e.g., chloroalkane (e.g., HALOTAG)) and a detectable reporter (e.g., fluorophore, luciferase (e.g., NANOLUC) or components of a luminescent complex (e.g., NANOBIT or NANOTRIP components). In some embodiments, purified HALOTAG-LgBiT (HT-LgBiT) and HALOTAG-SmBiT (HT-SmBiT) are used as reagents for the detection of incorporation of the haloalkyl-modified nucleotides into the newly synthesized DNA. In some embodiments, the binding of a reporter fusion (e.g., HT-NANOLUC) to a modified nucleotide in the nucleic acid allows for detection of the synthesized nucleic acid (and therefore detection of DNA synthesis and/or cellular proliferation). In some embodiments, the amount of reporter fusion (e.g., HT-NANOLUC) bound to modified nucleotides in the synthesized nucleic acid allows for quantification of the nucleic acid (and therefore quantification of the amount of DNA synthesis and/or cellular proliferation). In embodiments in which two or more different reporter fusions, each comprising a haloalkyl-binding moiety (e.g., HALOTAG) and a component of a bioluminescent complex (e.g., NANOBIT or NANOTRIP components), are used, detection is based on the assumption that upon significant incorporation of the haloalkyl-modified nucleotides into DNA, two haloalkyl-modified nucleotides will reside in close enough proximity at a frequency sufficient to observe facilitated complementation of the components of a bioluminescent complex. For example, binding of HT-SmBiT and HT-LgBiT to adjacent or nearby nucleotides brings the two BiTs together to produce an active luciferase complex, the activity of which can then be detected. Whereas non-complementary, close proximity binding of two HT-SmBiT or two HT-LgBiT entities will occur, the frequency of complementary binding is sufficient to enable detection. In the presence of a luciferase substrate, luminescence is produced in direct proportion to the quantity of haloalkyl-modified nucleotides incorporated into cells, which is a direct indication of cell proliferation.

In some embodiments, provided herein are haloalkyl-modified nucleosides (e.g., haloalkyl-modified deoxyuridines, haloalkyl-modified deoxyadenosine, haloalkyl-modified deoxycytidine; haloalkyl-modified deoxyguanosine, etc.) that, for example, find use in the DNA synthesis monitoring methods described herein.

In some embodiments, disclosed herein is a compound of formula (I):

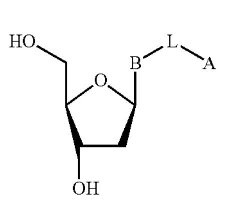

(I)

or a salt thereof, wherein: B is nucleobase or modified nucleobase, including but not limited to modified adenine, guanine, uracil, or cytosine; L is a linker; and A is a haloalkyl group. In some embodiments, B is selected from:

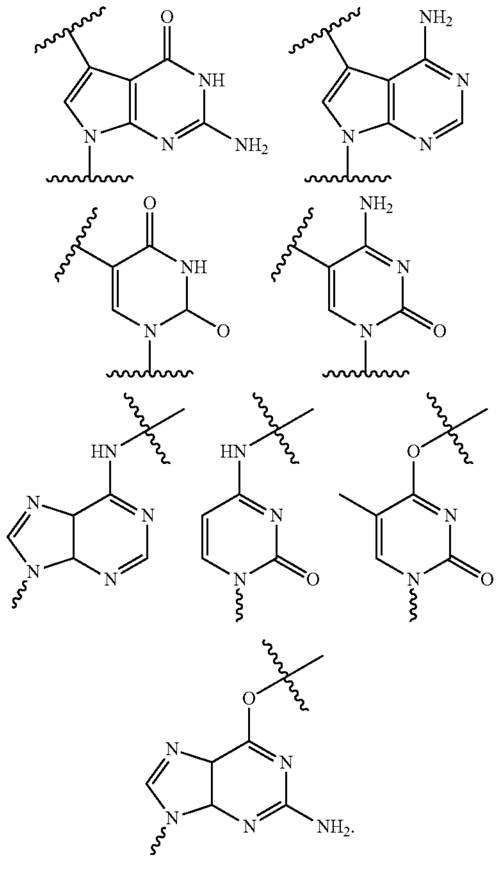

For example, when B is uracil, certain embodiments herein provide a haloalkyl-modified nucleoside of formula (IV):

(IV)

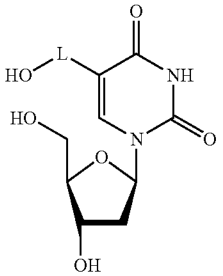

or a salt thereof, wherein L is a linker, and A is a haloalkyl group. Experiments herein demonstrate the incorporation of a haloalkyl-modified deoxyuridine nucleoside in DNA synthesis within a cell and detection/quantification of nucleic acid produced therefrom. Such experiments demonstrate the use of haloalkyl-modified nucleosides in the assays and systems herein. Embodiments herein are not limited to the use of haloalkyl-modified deoxyuridine nucleosides. In some embodiments, B is guanine, adenine, and/or cytosine, and a haloalkyl-modified nucleoside is provided of one or more of formulas (II), (III), and/or (V):

(ii)

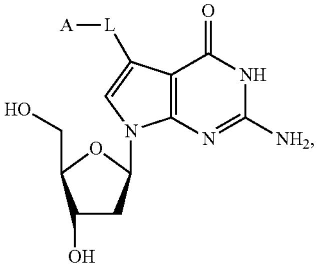

(III)

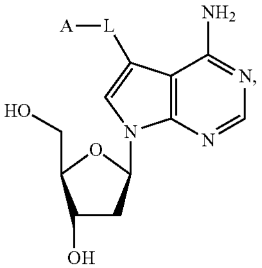

and/or (V)

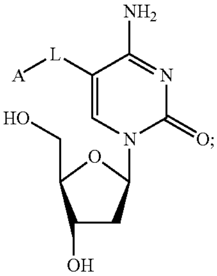

or a salt thereof, wherein L is a linker, and A is a haloalkyl group.

The group L is a linker. A wide variety of linkers can be used in compounds of formulas (I), (II), (III), (IV), and/or (V). In some embodiments, the linker comprises one or more groups independently selected from alkylene, alkenylene, alkynylene, arylene, —O—, —NH—, and —C(O)—. For example, the linker may include various combinations of such groups to provide linkers having amide (—C(O)NH—), carbamate (—NHC(O)O—), ester (—C(O)O—), urea (—NHC(O)NH—), and/or oligo- and poly-ethylene glycol (—$(CH_2CH_2O)_x$—) linkages, and the like. For example, in some embodiments, L comprises one or more groups selected from —$CH_2$—, —C≡C—, —C(O)NH—, —OC(O)NH—, —$CH_2CH_2O$—, and phenylene. In some embodiments, any of the aforementioned functional groups can be combined in any suitable linker for use in compounds and methods herein. Examples of such linkers and compound incorporating such linkers are provided herein. However, embodiments within the scope herein are not limited to the specific example provided herein. In some embodiments, the linker may include 2 or more atoms (e.g., 2-200 atoms, such as 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, or 200 atoms, or any range therebetween (e.g., 2-20, 5-10, 15-35, 25-100, etc.)).

In some embodiments, the linker L has a formula selected from:

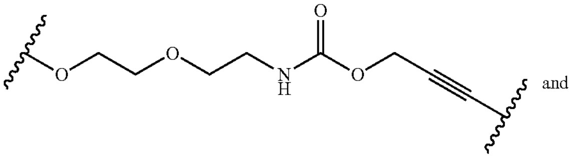

and

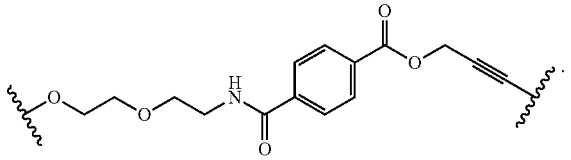

In some embodiments, L is C≡C-L', wherein L' is selected from alkyl, cyclic alkyl, alkylene, alkenylene, alkynylene, arylene, —O—, —NH—, —C(O)—, —$(CH_2)_m$—, 13 CH═CH—, —C≡C—, —C(O)NH—, —OC(O)NH—, —$CH_2CH_2O$—, and —$CH_2O$—, wherein m is 1-6.

In some embodiments, A is a haloalkyl group. In some embodiments, A comprises a terminal halogen selected from Cl, Br, F, and I. In some embodiments, the terminal halogen is Cl. In some embodiments, the terminal halogen is Br. In some embodiments, A comprises a suitable alkyl chain, such as (CH2)n wherein n is 2, 3, 4, 5, 6, 7, 8, 9, 10, 11, 12, or more. In some embodiments, A is a $C_2$-$C_{12}$ haloalkyl group. In some embodiments, A is —$(CH_2)_n$-X, wherein n is 4, 5, 6, 7, or 8, and X is halo. In some embodiments, X is Cl or Br. In some embodiments, n is 6. In some embodiments, X is Cl.

In some embodiments, a compound of formula (Ia) is provided:

(Ia)

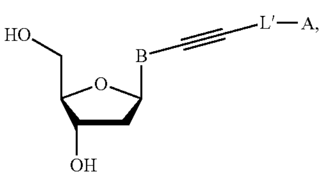

wherein L' is a linker. The linker L' can be any of the groups described herein for the linker L (e.g., can include one or more groups independently selected from alkylene, alkenylene, alkynylene, arylene, —O—, —NH—, —C(O)—, amide (—C(O)NH—), carbamate (—NHC(O)O—), ester (—C(O)O—), urea (—NHC(O)NH—), oligo- and polyethylene glycol (—$(CH_2CH_2O)_x$—) linkages, —$CH_2$—, —C≡C—, —C(O)NH—, —OC(O)NH—, —$CH_2CH_2O$—, phenylene, etc.). For example, L' can have a formula selected from:

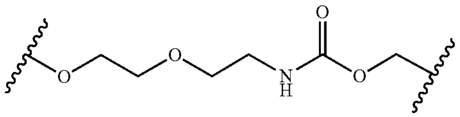

and

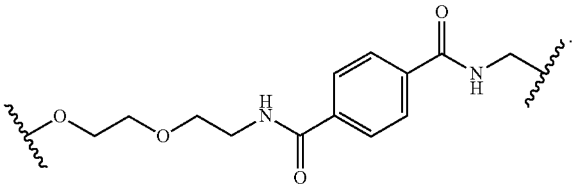

In some embodiments, C≡C-L' is selected from:

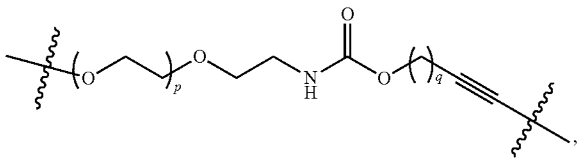

,

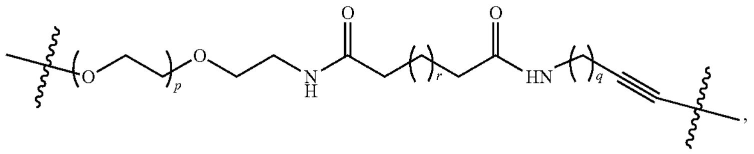

,

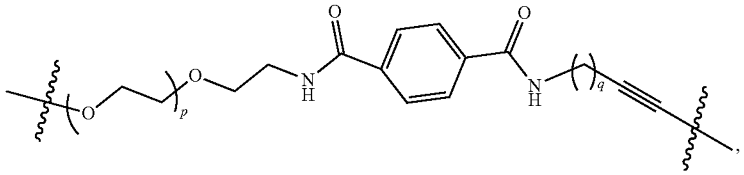

,

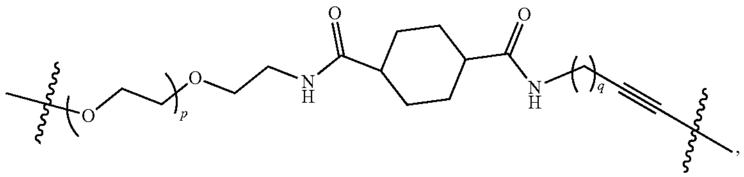

,

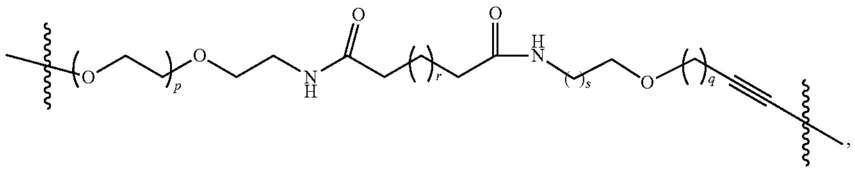

,

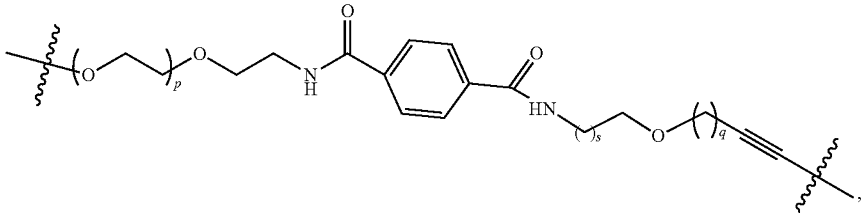

,

-continued

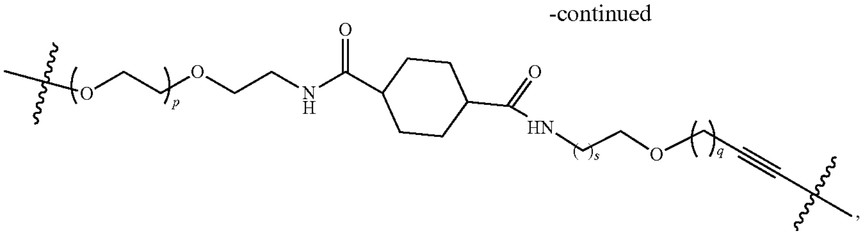
,

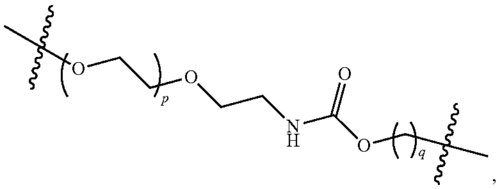
,
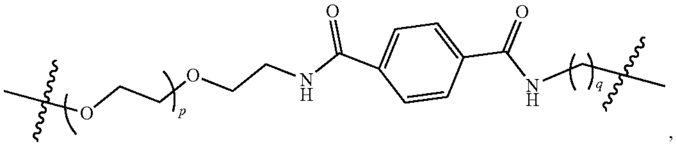
,

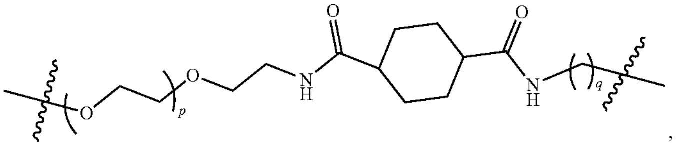
,
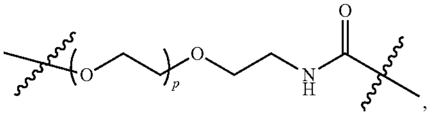
,

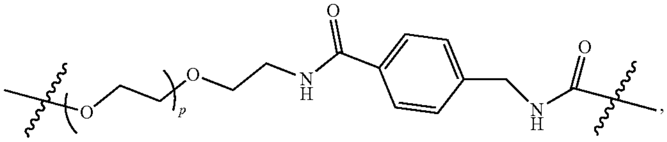
,

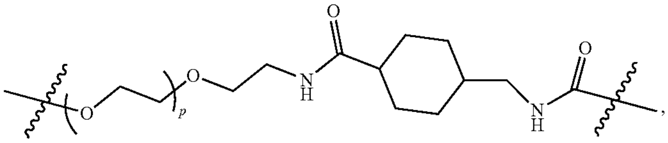
,

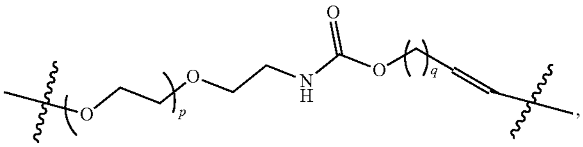
,

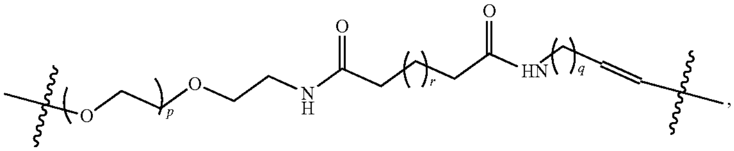
,

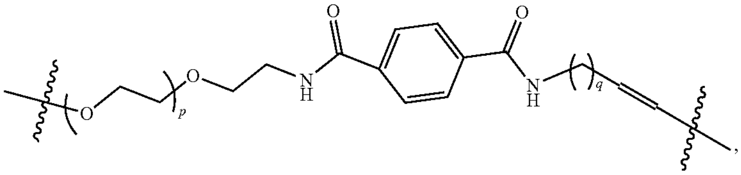
, and

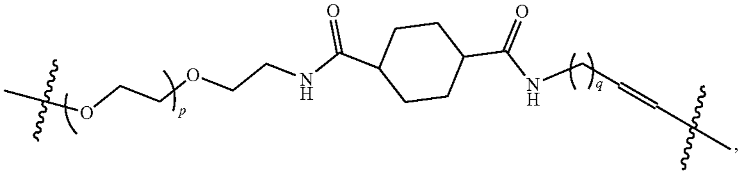
, wherein p, q, r, and s are each independently 1-6. In some embodiments, A is a haloalkyl group as described herein. The group A is a haloalkyl group. For example, in some embodiments, A is a $C_2$-$C_{12}$ haloalkyl group, e.g., a $C_2$-$C_{10}$ haloalkyl group or a $C_2$-$C_8$ haloalkyl group. In some embodiments, A has the formula $-(CH_2)_n$-X, wherein n is 4, 5, 6, 7, or 8, and X is a halogen (i.e., F, Cl, Br, or I). In some embodiments, X is Cl. In some embodiments, n is 6 and X is Cl such that A has formula $-(CH_2)_6-Cl$. In some embodiments, the haloalkyl group may be further substituted with substituents that do not interfere with interaction with the mutant dehalogenase.

In such embodiments, A is a substrate for a dehalogenase, e.g., a haloalkane dehalogenase. Systems comprising mutant hydrolases (e.g., mutant dehalogenases) that covalently bind their substrates (e.g., haloalkyl substrates) are described, for example, in U.S. Pat. Nos. 7,238,842; 7,425,436; 7,429,472; 7,867,726; each of which is herein incorporated by reference in its entirety. HALOTAG is a commercially-available modified dehalogenase enzyme that forms a stable (e.g., covalent) bond (e.g., ester bond) with its haloalkyl substrate, which finds use in embodiments herein.

In some embodiments, provided herein is a compound of formula (IIa), (IIIa), (IVa), or Va):

(II)

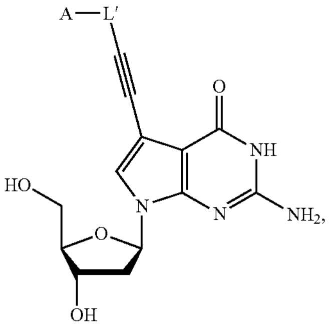

(III)

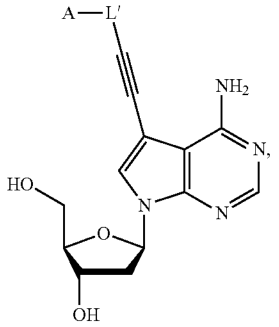

(IVa)

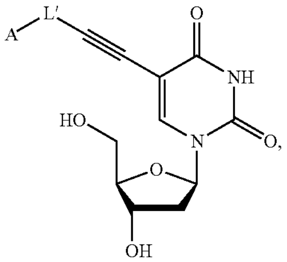

-continued and (V)

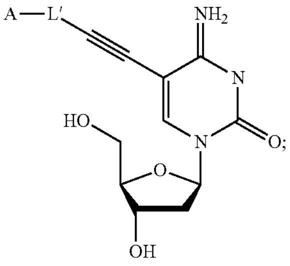

wherein A is a haloalkyl group as defined herein, and L' is a linker comprising any of the groups described herein for the linker L (e.g., can include one or more groups independently selected from alkylene, alkenylene, alkynylene, arylene, —O—, —NH—, —C(O)—, amide (—C(O)NH—), carbamate (—NHC(O)O—), ester (—C(O)O—), urea (—NHC(O)NH—), oligo- and poly-ethylene glycol (—$(CH_2CH_2O)_x$—) linkages, —$CH_2$—, —C≡C—, —C(O)NH—, —OC(O)NH—, —$CH_2CH_2O$—, phenylene, etc.). For example, L' can have a formula selected from:

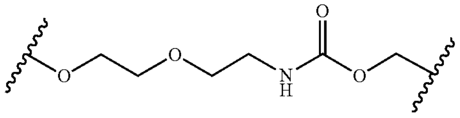

and

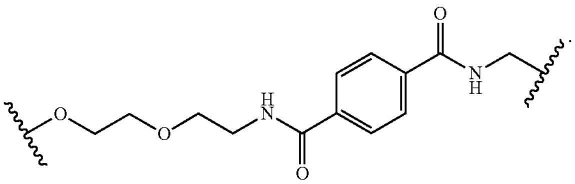

In some embodiments, —C≡C-L' is selected from:

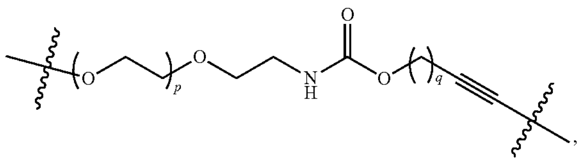

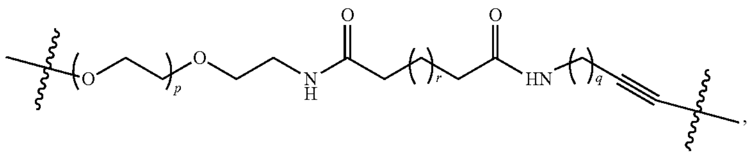

-continued
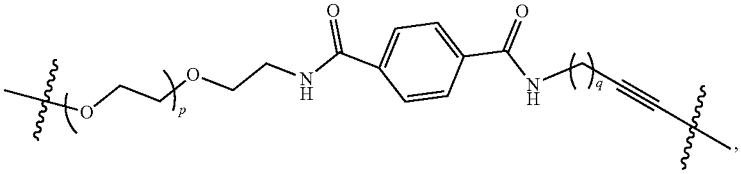
,
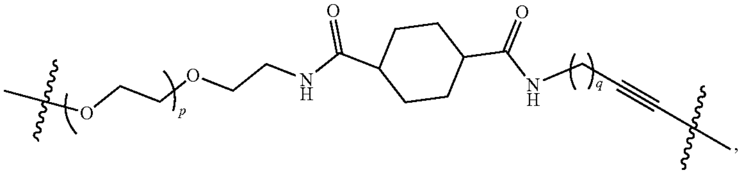
,
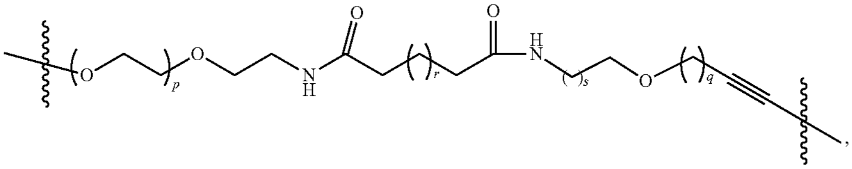
,
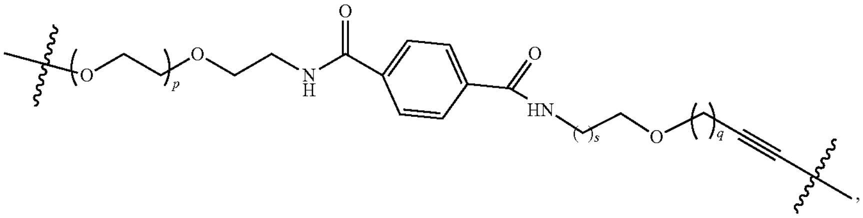
,
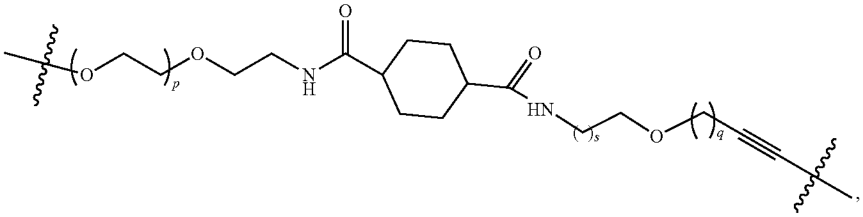
,
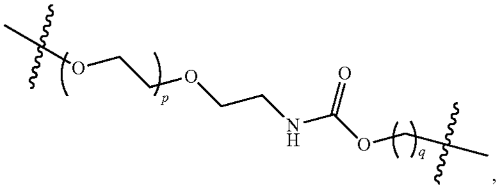
,
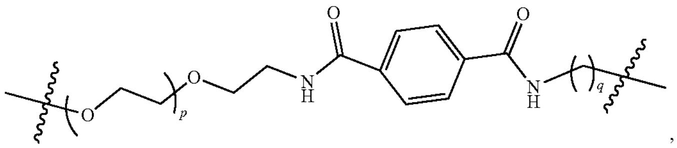
,
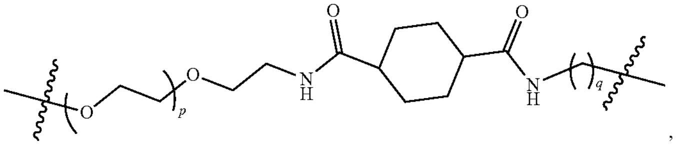
,
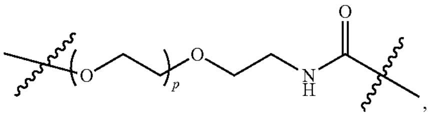
,
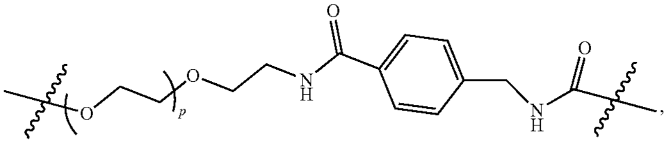
,
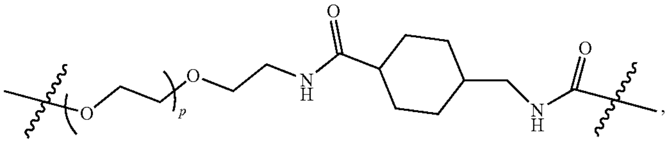
,
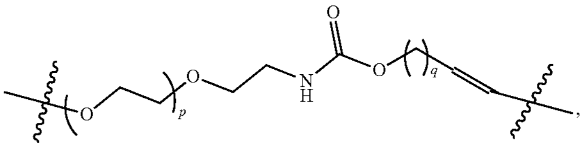
, -continued
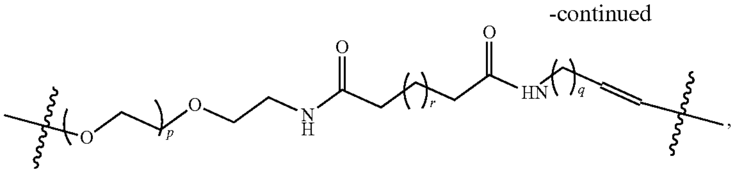
,
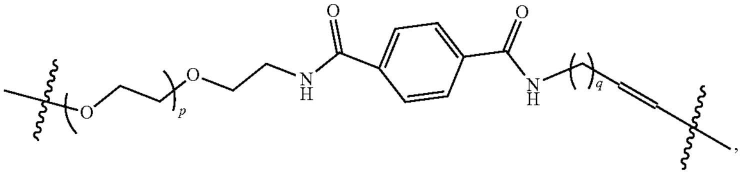
, and
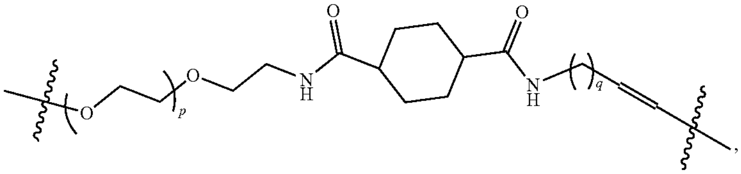
,
wherein p, q, r, and s are each independently 1-6.
In some embodiments, haloalkyl-modified nucleosides are provided herein, for example, as described above. In other embodiments, haloalkyl-modified nucleobases are provided:
(IIb)
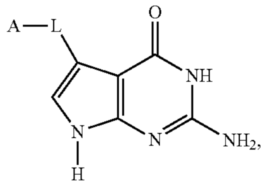
(IIIb)
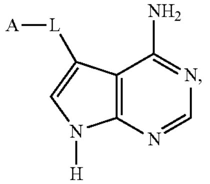
(IVb)
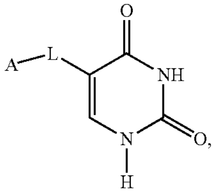
and
(Vb)
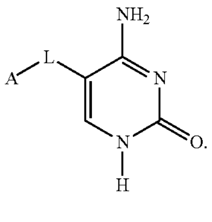
In certain embodiments, haloalkyl-modified nucleotide-monophosphates 10 are provided, such as:
(Ic)
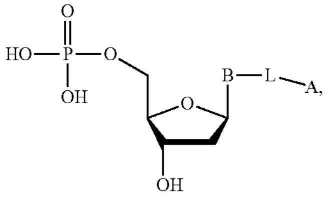
(IIc)
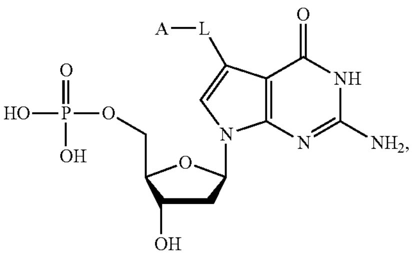
(IIIc)
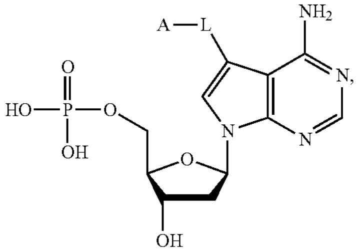
(IVc)
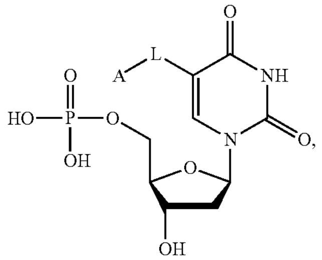
and -continued (Vc)

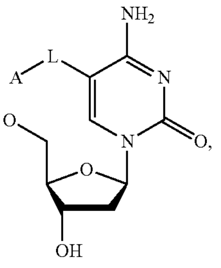

In some embodiments, haloalkyl-modified nucleotide-triphosphates are provided:

(Id)

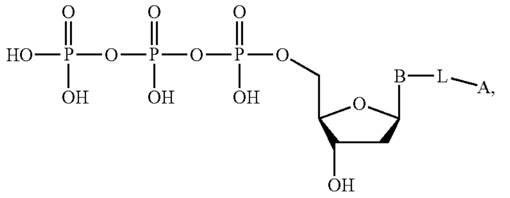

(IId)

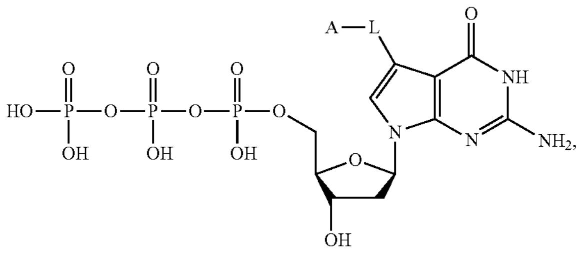

(IIId)

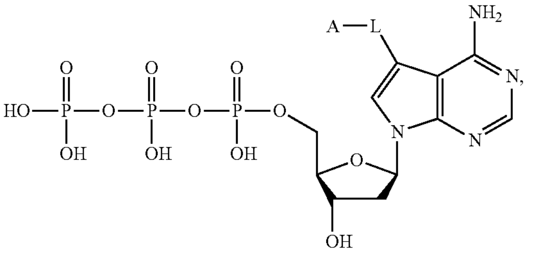

(IVd)

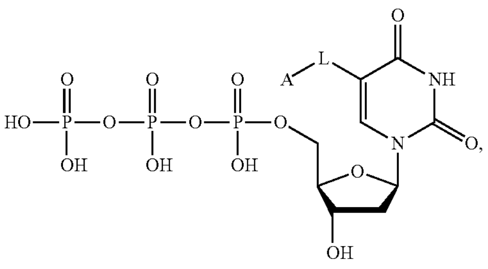

and

-continued (Vd)

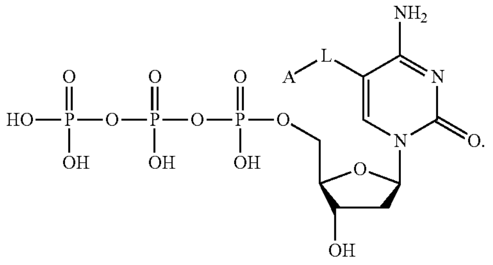

For haloalkyl-modified nucleobases, haloalkyl-modified nucleotide-monophosphates, and haloalkyl-modified nucleotide-triphosphates, B (when present) is selected from:

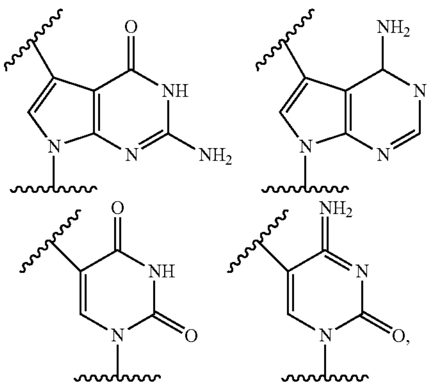

and A and L are selected from any of the A and L groups described herein for haloalkyl-modified nucleosides.

In particular embodiments, a compound of formula (IV) is provided. Such embodiments are well exemplified herein and provide a demonstration of the use of haloalkyl-modified deoxynucleosides in the compositions and methods herein.

Compounds of formulas (I), (Ia), (Ib), (Ic), (Id), (II), (IIa), (IIb), (IIc), (IId), (III), (IIIa), (IIIb), (IIIc), (IIId), (IV), (IVa), (IVb), (IVc), (IVd), (V), (Va), (Vb), (Vc), and (Vd), can be in the form of a salt. Acid salts may be prepared during the final isolation and purification of the compounds or separately by reacting a suitable group of the compound such as an amino group with a suitable acid. For example, a compound may be dissolved in a suitable solvent, such as but not limited to methanol and water, and treated with at least one equivalent of an acid such hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides, and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Compounds herein may be synthesized by a variety of methods, including those illustrated in Scheme 1 and Scheme 2.

Scheme 1.

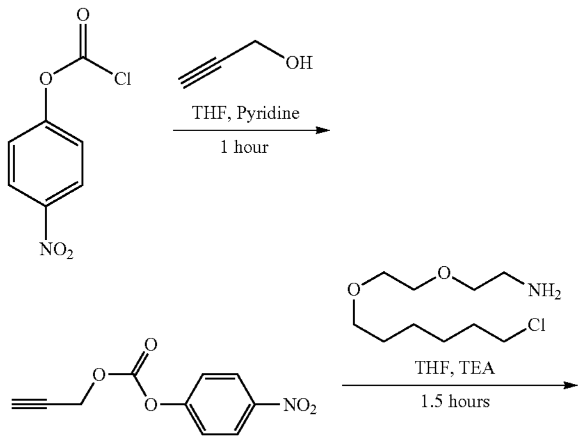

-continued

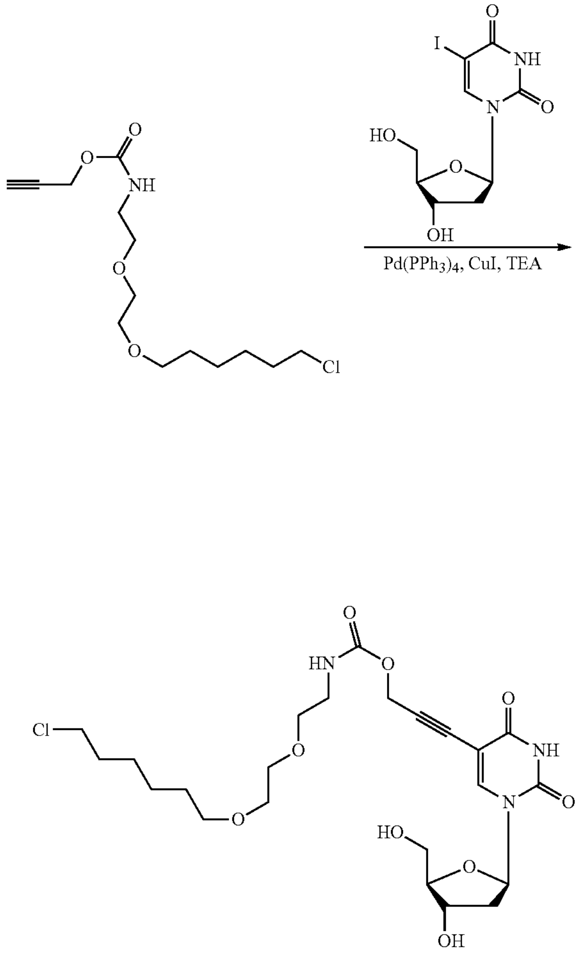

PBI 7931

Scheme 2.

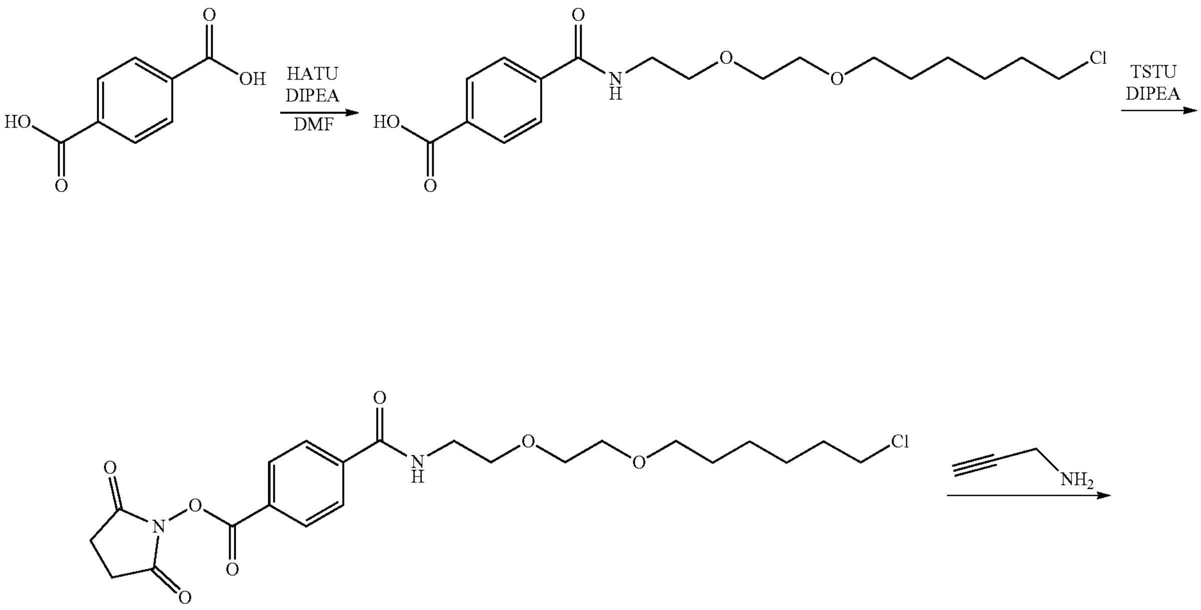

-continued

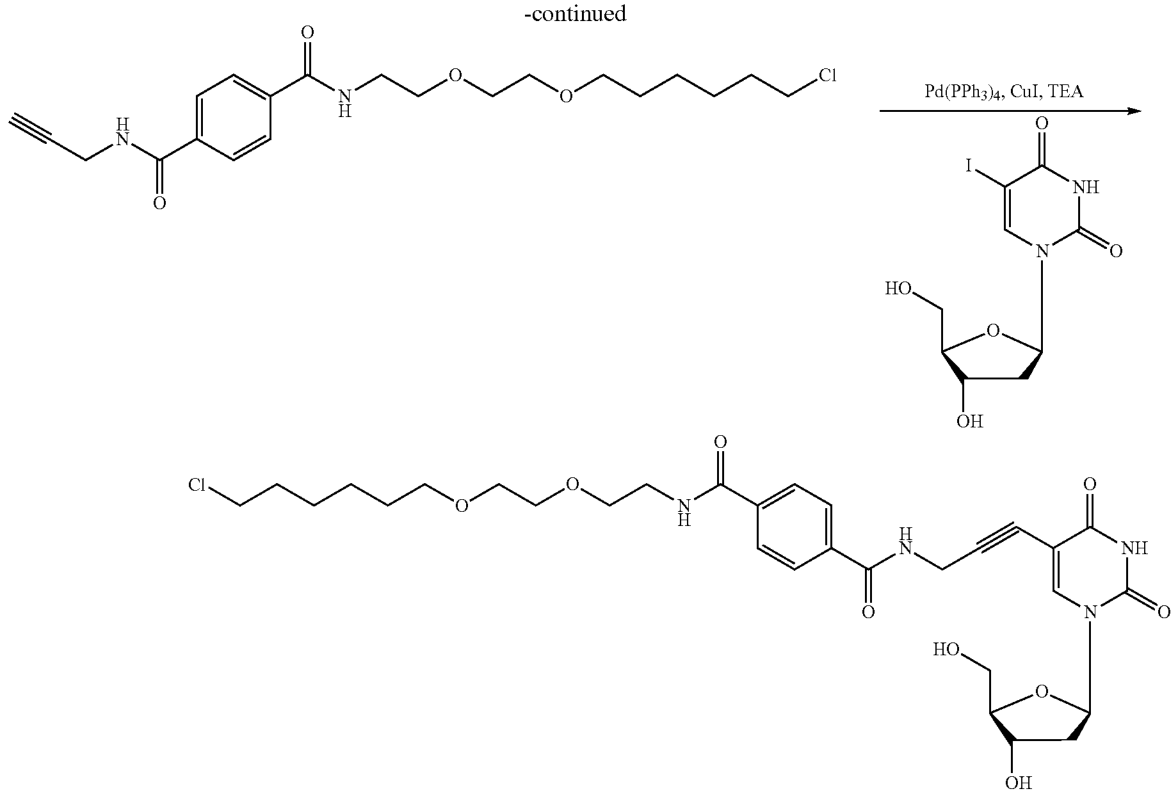

PBI 7960

As described in Scheme 1, propagyl alcohol was activated with p-nitrophenyl chloroformate, and then reacted with chlorohexyl-PEG2-amine to yield propagyl hexyl-chloro-PEG2-carbamate. Propagyl hexyl-chloro-PEG2-carbamate was coupled to 5-iodo-dU catalyzed by palladium tetrakis and CuI to generate compound PBI 7931.

PBI 7960 was obtained by employing the method as described in Scheme 2. Terephthalic acid was coupled to hexyl chloro-PEG2-amine under standard HATU coupling condition to yield 4-((2-(2-((6-chlorohexyl)oxy)ethoxy)ethyl)carbamoyl)benzoic acid. 4-((2-(2-((6-Chlorohexyl)oxy)ethoxy)ethyl)carbamoyl)benzoic acid was activated by TSTU and then reacted with propagyl amine to generate N1-(2-(2-((6-chlorohexyl)oxy)ethoxy)ethyl)-N4-(prop-2-yn-1-yl)terephthalamide. N1-(2-(2-((6-Chlorohexyl)oxy)ethoxy)ethyl)-N4-(prop-2-yn-1-yl)terephthalamide was coupled to 5-iodo-dU catalyzed by palladium tetrakis and CuI to generate compound PBI 7960.

Compounds (e.g., or formulas (I), (Ia), (Ib), (Ic), (Id), (II), (IIa), (IIb), (IIc), (IId), (III), (IIIa), (IIIb), (IIIc), (IIId), (IV), (IVa), (IVb), (IVc), (IVd), (V), (Va), (Vb), (Vc), and/or (Vd)), and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the disclosure can be accomplished by methods analogous to those described in the synthetic schemes described herein and in specific examples.

Some of the compounds of the present disclosure have at least one asymmetric center. Additional asymmetric centers may be present depending upon the nature of the various substituent groups. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this disclosure.

The independent syntheses of enantiomerically or diastereomerically enriched compounds, or their chromatographic separations, may be achieved as known in the art by appropriate modification of the methodology disclosed herein. The absolute stereochemistry of a compound may be determined by using X-ray crystallography to determine the crystal structure of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

The present disclosure also includes isotopically-labeled compounds (e.g., an isotopically-labeled compound of formulas (I), (Ia), (Ib), (Ic), (Id), (II), (IIa), (IIb), (IIc), (IId), (III), (IIIa), (IIIb), (IIIc), (IIId), (IV), (IVa), (IVb), (IVc), (IVd), (V), (Va), (Vb), (Vc), (Vd), etc.), which are identical to those recited in formulas (I), (Ia), (Ib), (Ic), (Id), (II), (IIa), (IIb), (IIc), (IId), (III), (IIIa), (IIIb), (IIIc), (IIId), (IV), (IVa), (IVb), (IVc), (IVd), (V), (Va), (Vb), (Vc), and (Vd), etc., but for the fact that one or more atoms are replaced by an atom having an atomic mass or mass number different from the atomic mass or mass number usually found in nature. Examples of isotopes suitable for inclusion in the compounds of the disclosure are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{31}P$, $^{35}S$, $^{18}F$, and $^{36}Cl$, respectively. Isotopically-labeled compounds of formulas (I), (Ia), (Ib), (Ic), (Id), (II), (IIa), (IIb), (IIc), (IId), (III), (IIIa), (IIIb), (IIIc), (IIId), (IV), (IVa), (IVb), (IVc), (IVd), (V), (Va), (Vb), (Vc), (Vd), etc., can generally be prepared by conventional techniques known to those skilled in the art or by processes analogous to those described herein using an appropriate isotopically-labeled reagent in place of a non-isotopically-labeled reagent.

The present disclosure provides assays, systems, and methods for detecting and/or measuring DNA synthesis by monitoring the incorporation of haloalkyl-modified nucleosides into newly synthesized DNA. In accordance with these embodiments, the present disclosure provides materials and methods for the detection and/or quantification of DNA incorporated with haloalkyl-modified nucleosides. In some embodiments, the bioluminescent/fluorescent polypeptides and/or bioluminescent/fluorescent complexes are linked to a haloalkyl labels on DNA using a protein agent (e.g., modified halo-alkane dehydrogenase protein (e.g., HALOTAG), etc.) that covalently binds a haloalkane on the DNA.

In some embodiments, provided herein are materials and methods related to bioassays for the detection of haloalkyl-containing DNA with cells or a cell lysate. In some embodiments, provided herein are bioassays that incorporate haloalkyl-labeled DNA (e.g., containing haloalkyl-modified nucleosides) and bioluminescent polypeptides and/or bioluminescent complexes (of peptide(s) and/or polypeptide components that exhibit enhanced luminescence upon complex formation) that are based on (e.g., structurally, functionally, etc.) the luciferase of *Oplophorus gracilirostris*, the NANOLUC luciferase (Promega Corporation; U.S. Pat. Nos. 8,557,970; 8,669,103; herein incorporated by reference in their entireties), the NANOBiT (U.S. Pat. No. 9,797,889; herein incorporated by reference in its entirety), NanoTrip (U.S. Pat. Pub. No. 2020/0270586; herein incorporated by reference in its entirety), and/or other multipartite bioluminescent technologies (Intl. App. No. PCT/US19/36844; Intl. App. No. PCT/US20/62499; and U.S. application Ser. No. 17/105,925; herein incorporated by reference in its entirety). As described herein, bioassays can incorporate commercially available NANOLUC-based technologies (e.g., NANOLUC luciferase, NanoBRET, NANOBiT, NanoTrip, NANOGLO, etc.), but in other embodiments, various combinations, variations, or derivations from the commercially available NANOLUC-based technologies are employed.

PCT Appln. No. PCT/US2010/033449, U.S. Pat. No. 8,557,970, PCT Appln. No. PCT/2011/059018, and U.S. Pat. No. 8,669,103 (each of which is herein incorporated by reference in their entirety and for all purposes) describe compositions and methods comprising bioluminescent polypeptides. Such polypeptides find use in embodiments herein and can be used in conjunction with the compositions, assays, and methods described herein. In some embodiments, compositions, assays, and methods provided herein comprise a bioluminescent polypeptide of SEQ ID NO: 5 or having at least 60% (e.g., 60%, 65%, 70%, 75%, 80%, 85%, 90%, 95%, 96%, 97%, 98%, 99%, 100%, or ranges therebetween) sequence identity with SEQ ID NO: 5. In some embodiments, any of the aforementioned bioluminescent polypeptides are linked (e.g., fused, chemically linked, etc.) to a modified dehalogenase (e.g., HALOTAG) or utilize another system comprised of complementary binding partners The native *Oplophorus gracilirostris* luciferase (OgLuc) and commercially-available NANOLUC luciferase (Promega Corporation) each comprise polypeptides of 10 β (beta) strands (β1, β2, β3, β4, β5, β6, β7, β8, β9, β10). U.S. Pat. No. 9,797,889 (herein incorporated by reference in its entirety) describes development and use of a complementation system comprising a β1-9-like polypeptide and a β10-like peptide (the actual polypeptide and peptide sequences in U.S. Pat. No. 9,797,889 differ from the corresponding sequences in NANOLUC and wild-type native OgLuc).

Multipartite complementation systems (e.g., bipartite, tripartite, etc.) have been developed by combining peptides and polypeptides that collectively correspond to the full set of 10 β (beta) strands of these luciferases. Upon combination of the set of complementary peptides and polypeptides, under appropriate conditions (e.g., facilitated by the binding of capture reagents fused to the complementation components to capture elements), a bioluminescent complex is formed. In some embodiments, peptide and polypeptide components of the bioluminescent complexes find use as detection reagents (e.g., fused to capture agents) for the detection of protein labeled by the compositions and methods herein (and thereby cell death is detected). These multipartite complementation systems are described in, for example, PCT Appln. No. PCT/US14/26354; U.S. Pat. No. 9,797,889; U.S. Pat. Pub. No. 2020/0270586; Intl. App. No. PCT/US19/36844; Intl. App. No. PCT/US20/62499; and U.S. application Ser. No. 17/105,925 (herein incorporated by reference in their entireties and for all purposes); and examples of these technologies are described below.

PCT Appln. No. PCT/US14/26354 and U.S. Pat. No. 9,797,889 (each of which is herein incorporated by reference in their entirety and for all purposes) describe compositions and methods for the assembly of bioluminescent complexes; such complexes, and the peptide and polypeptide components thereof, find use in embodiments herein and can be used in conjunction with the compositions, assays, and methods described herein. In some embodiments, NANOBiT and other related technologies utilize a peptide component and a polypeptide component that, upon assembly into a complex, exhibit significantly-enhanced (e.g., 2-fold, 5-fold, 10-fold, $10^2$-fold, $10^3$-fold, $10^4$-fold, or more) luminescence in the presence of an appropriate substrate (e.g., coelenterazine or a coelenterazine analog) when compared to the peptide component and polypeptide component alone.

In some embodiments, provided herein are polypeptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 9. In some embodiments, polypeptides have less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, and/or SEQ ID NO: 6. In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 10. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8. In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 11. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8. In some embodiments, any of the aforementioned peptide or polypeptide components of a bioluminescent complex are linked (e.g., fused, chemically linked, etc.) to a modified dehalogenase (e.g., HALOTAG), or utilize another system comprised of complementary binding partners. In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 10. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8. In some embodiments, any of the aforementioned peptide or polypeptide components of a bioluminescent complex are linked (e.g., fused, chemically linked, etc.) to a modified dehalogenase (e.g., HALOTAG), or utilize another system comprised of complementary binding partners.

U.S. Pat. Pub. No. 2020/0270586; Intl. App. No. PCT/US20/62499; and U.S. application Ser. No. 17/105,925 (herein incorporated by reference in their entireties and for all purposes) describe compositions, systems, and methods for the assembly of bioluminescent complexes from three or more peptide and polypeptide components. Such complexes, and the peptides and polypeptide components thereof, can be used in conjunction with the compositions, assays, and methods described herein.

In some embodiments, provided herein are polypeptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 12 or 19. In some embodiments, polypeptides have less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, SEQ ID NO: 6, and/or SEQ ID NO: 9.

In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 11. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8.

In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 13. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 5, and/or SEQ ID NO: 7.

In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 14. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 4, SEQ ID NO: 5, SEQ ID NO: 7, and/or SEQ ID NO: 8. In some embodiments, any of the aforementioned peptide and/or polypeptide components are linked (e.g., fused, chemically linked, etc.) to a modified dehalogenase (e.g., HALOTAG), or utilize another system comprised of complementary binding partners. PCT Appln. No. PCT/US13/74765; U.S. patent application Ser. No. 15/263,416 (herein incorporated by reference in their entireties and for all purposes) and other patents and applications describes bioluminescence resonance energy transfer (BRET) compositions, assays, and methods (e.g., incorporating NanoLuc®-based technologies); such compositions, assays and methods, and the bioluminescent polypeptide and fluorophore-conjugated components thereof, can be used in conjunction with the compositions, assays, and methods described herein. In some embodiments, any of the NANOLUC-based, NANOBiT-based, and/or multipartite NANOLUC-based or related peptides, polypeptides, complexes, fusions, and conjugates may find use in BRET-based applications with the compositions, assays, and methods described herein. For example, a first detection agent that comprises a haloalkyl binding moiety (e.g., HALOTAG) and reporter (e.g., luciferase, fluorescent protein, etc.) that emits a signal at a first emission wavelength and a second detection agent that comprises a haloalkyl binding moiety (e.g., HALOTAG) and a fluorescent reporter (e.g., fluorescent protein, fluorophore, etc.) with an excitation spectrum that overlaps the first emission wavelength and emits signal at a second emission wavelength are used to detect haloalkyl incorporation into nucleic acid via BRET. Other combinations of luminescent and fluorescent moieties (e.g., fused to HALOTAG) find use in BRET-mediated detection/quantification of haloalkyl-modified nucleic acids using the systems and methods herein.

As used herein, the term "energy acceptor" refers to any small molecule (e.g., chromophore), macromolecule (e.g., autofluorescent proteins, phycobiliproteins, nanoparticles, surfaces, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog) such as those described in U.S. patent application Ser. No. 13/682,589, herein incorporated by reference in its entirety. In some embodiments, a fluorophore is an acceptor in a BRET application of the technology herein.

The assays and methods of the present disclosure include the use of a luminogenic substrate. Bioluminescence, as described herein, generally refers to production and emission of light by a chemical reaction catalyzed by, or enabled by, an enzyme, protein, protein complex, or other biomolecule (e.g., bioluminescent complex). In typical embodiments, a luminogenic substrate for a bioluminescent entity (e.g., bioluminescent protein or bioluminescent complex) is converted into an unstable form by the bioluminescent entity; the substrate subsequently emits light. In the presence of detection reagents (e.g., polypeptide component(s) of a bioluminescent complex) and substrate (e.g., coelenterazine or coelenterazine analog), a bioluminescent signal is produced. Provided herein are compositions that include a luminogenic substrate such as coelenterazine or an analog or derivative thereof. Exemplary coelenterazine analogs include coelenterazine-h, coelenterazine-h-h, and furimazine.

In some embodiments, the substrate is coelenterazine, which has the following structure:

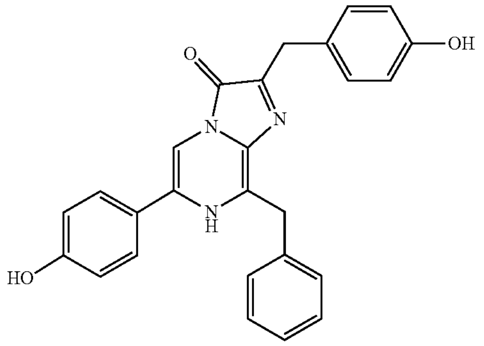

coelenterazine

In some embodiments, the substrate is a coelenterazine analog or derivative. Exemplary coelenterazine analogs include coelenterazine-h (2-deoxycoelenterazine or 2,8-dibenzyl-6-(4-hydroxyphenyl)imidazo[1,2-a]pyrazin-3(7H)-one), coelenterazine-h-h (dideoxycoelenterazine or 2,8-dibenzyl-6-phenylimidazo[1,2-a]pyrazin-3(7H)-one), and furimazine (8-benzyl-2-(furan-2-ylmethyl)-6-phenylimidazo[1,2-a]pyrazin-3(7H)-one), which have the following structures:

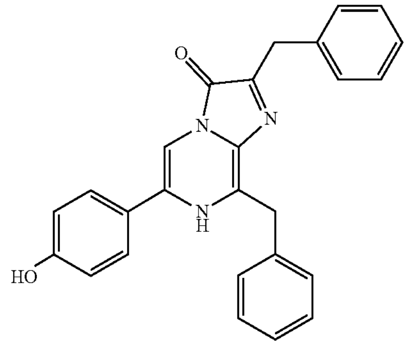

coelenterazine-h

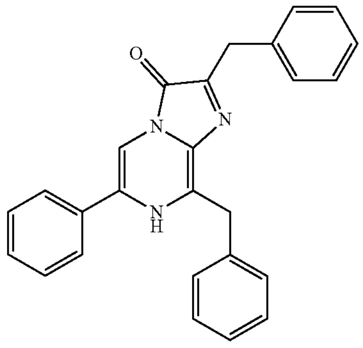

coelenterazine-hh

-continued

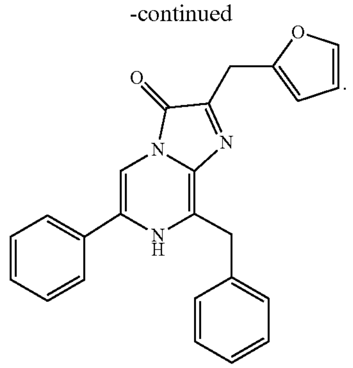

furimazine

Additional exemplary coelenterazine analogs include coelenterazine-n, coelenterazine-f, coelenterazine-hcp, coelenterazine-cp, coelenterazine-c, coelenterazine-e, coelenterazine-fcp, coelenterazine-i, coelenterazine-icp, coelenterazine-v, 2-methyl coelenterazine, and the like. In some embodiments, the compound may be a coelenterazine analog described in WO 2003/040100; U.S. application Ser. No. 12/056,073 (paragraph [0086]); U.S. Pat. No. 8,669,103; WO 2012/061529, U.S. Pat. Pub. 2017/0233789, and U.S. Pat. Pub. 2018/0030059; the disclosures of which are incorporated by reference herein in their entireties. In some embodiments, coelenterazine analogs or derivatives include pro-substrates such as, for example, those described in U.S. application Ser. No. 12/056,073; U.S. Pub. No. 2012/0707849; U.S. Pub. No. 2014/0099654; herein incorporated by reference in their entireties. In some embodiments, the compound is furimazine.

Coelenterazine and analogs and derivatives thereof may suffer from challenges associated with their reconstitution into buffer systems used in many assays such as the bioluminogenic methods described herein. For example, coelenterazines, or analogs or derivatives thereof, such as furimazine, may dissolve slowly and/or inconsistently in buffer solutions (e.g., due to the heterogeneous microcrystalline nature of the solid material). While dissolution in organic solvent prior to dilution with buffer may provide faster and more consistent results, coelenterazine compounds may suffer from instability in organic solutions on storage, including both thermal instability and photo-instability. In some embodiments, the composition further comprises a polymer. As further described herein, the presence of the polymer may stabilize the compound against decomposition, and the presence of the polymer may improve the solubility of the compound in water or in aqueous solutions.

The polymer may be a naturally-occurring biopolymer or a synthetic polymer. In some embodiments, the polymer is a naturally-occurring biopolymer. Suitable naturally-occurring biopolymers are carbohydrates, including disaccharides (e.g., trehalose and maltose), and polysaccharides (e.g., pullulan, dextran, and cellulose). Mixtures of naturally-occurring biopolymers may also be used. In some embodiments, the polymer is pullulan, which is a polysaccharide that includes maltotriose repeating units. Maltotriose is a trisaccharide that includes three glucose units that are linked via α-1,4 glycosidic bonds. The maltotriose units within the pullulan polymer are linked to each other via α-1,6 glycosidic bonds.

In some embodiments, the polymer is a synthetic polymer. A synthetic polymer may be a homopolymer, copolymer, or block copolymer (e.g., diblock copolymer, triblock copolymer, etc.). Non-limiting examples of suitable polymers include, but are not limited to polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes (e.g., polyethylene and polypropylene), polyalkylene glycols (e.g., poly(ethylene glycol) (PEG)), polyalkylene terephthalates (e.g., poly(ethylene terephthalate), etc.), polyvinyl alcohols (PVA), polyvinyl ethers, polyvinyl esters (e.g., poly(vinyl acetate), etc.), polyvinyl halides (e.g., poly(vinyl chloride) (PVC), etc.), polyvinylpyrrolidone, polysiloxanes, polystyrene (PS), polyurethanes, derivatized celluloses (e.g., alkyl celluloses, hydroxyalkyl celluloses, cellulose ethers, cellulose esters, nitro celluloses, hydroxypropylcellulose, carboxymethylcellulose, etc.), polymers of acrylic acids ("polyacrylic acids") (e.g., poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate), polydioxanone and its copolymers (e.g., polyhydroxyalkanoates, polypropylene fumarate), polyoxymethylene, poloxamers, poly(ortho)esters, poly(butyric acid), poly(valeric acid), poly(lactide-co-caprolactone), trimethylene carbonate, and mixtures and copolymers thereof.

In addition to the compound and the polymer, the composition may include additional components such as buffers, surfactants, salts, proteins, or any combination thereof. For example, the composition may include a buffer such as a phosphate buffer, a borate buffer, an acetate buffer, or a citrate buffer, or other common buffers such as bicine, tricine, tris(hydroxymethyl)aminomethane (tris), N-[tris(hydroxymethyl)methyl]-3-aminopropanesulfonic acid (TAPS), 3-[N-tris(hydroxymethyl)methylamino]-2-hydroxypropanesulfonic acid (TAPSO), 2-[4-(2-hydroxyethyl) piperazin-1-yl]ethanesulfonic acid (HEPES), N-[tris(hydroxymethyl)methyl]-2-aminoethanesulfonic acid (TES), piperazine-N,N'-bis(2-ethanesulfonic acid) (PIPES), 2-(N-morpholino)ethanesulfonic acid (MES), or the like.

In some embodiments, the composition may include a surfactant. Exemplary surfactants include non-ionic surfactants, anionic surfactants, cationic surfactants, and zwitterionic surfactants. For example, the surfactant may be a non-ionic surfactant such as sorbitan 20. In some embodiments, the composition may include a salt, such as sodium chloride, potassium chloride, magnesium chloride, or the like. In some embodiments, the composition may include a protein. For example, the composition can include a carrier protein to prevent surface adsorption of luminogenic enzymes that may be added in downstream assays. In some embodiments, the protein may be bovine serum albumin (BSA).

Embodiments herein comprise incorporation of haloalkyl-modified nucleosides into DNA (and/or DNA displaying haloalkyl groups). In some embodiments herein, haloalkyl group on DNA are utilized as substrates for a dehalogenase, e.g., a haloalkane dehalogenase. Systems comprising mutant hydrolases (e.g., mutant dehalogenases) that covalently bind their substrates (e.g., haloalkyl substrates) are described, for example, in U.S. Pat. Nos. 7,238,842; 7,425,436; 7,429,472; 7,867,726; each of which is herein incorporated by reference in its entirety. HALOTAG is a commercially-available modified dehalogenase enzyme that forms a stable (e.g., covalent) bond (e.g., ester bond) with its haloalkyl substrate, which finds use in embodiments herein. In some embodiments, a modified dehalogenase (e.g., HALOTAG) binds (covalently) to haloalkyl groups incorporated into DNA during DNA synthesis.

It has been demonstrated that a modified dehalogenases that form covalent bonds with their haloalkyl substrates (e.g., HALOTAG) can be incorporated into fusions with other proteins (e.g., reporter proteins (e.g., luciferases) while retaining their capacity to covalently bind their substrate. In some embodiments, provided herein are fusions of modified dehalogenases (e.g., HALOTAG) with a detectable reporter (e.g., bioluminescent protein, component of a bioluminescent complex, etc.). In some embodiments, upon binding of the modified dehalogenase (e.g., HALOTAG) to haloalkyl groups on haloalkyl-modified DNA, the DNA is quantified and/or synthesis on the DNA is monitored/quantified.

Systems and methods are provided herein for the modification of DNA with halkoalkyl groups during synthesis of the DNA. In some embodiments, haloalkyl-modified deoxynucleosides (e.g., deoxyuridines) are provided with the other typical components of DNA replication (e.g., DNA template, DNA polymerase, unlabeled deoxynucleosides (dA, dT, dC, dG), etc.). In some embodiments, the haloalkyl-modified deoxynucleosides are incorporated into the newly-synthesized DNA in place of a portion of the doxythymidines (e.g., at a constant or relatively constant rate (e.g., proportional to the ratio of haloalkyl-modified deoxyuridines to deoxythymidines present). The newly synthesized DNA is subsequently detected by exposing the DNA to a binding/detection agent that (i) is capable of binding to the haloalkyl groups and (ii) exhibits a detectable characteristic.

In some embodiments, the binding/detection agent comprises a haloalkyl-binding moiety and a detectable moiety. In some embodiments, the haloalkyl-binding moiety is a modified dehalogenase that binds covalently to its haloalkyl substrate (e.g., HALOTAG). In some embodiments, the detectable moiety is a luminescent polypeptide, a luciferase enzyme, and/or a component of a luminescent complex. If the detectable moiety is a luminescent polypeptide or a luciferase enzyme, then the amount of luminescence detected in the presence of the newly synthesized DNA (after washing away excess free binding/detection agent) is proportional to the amount of newly synthesized DNA (and to the rate of deoxyuridine incorporation into the DNA). If the detectable moiety is a component of a luminescent complex, then luminescence is detectable if the haloalkyl-modified deoxyuridines are incorporated into the newly synthesized DNA at a density sufficient to result in complementary components of the luminescent complex being bound in close proximity on the newly synthesized DNA.

In some embodiments, provided herein are methods of modifying a nucleic acid comprising including haloalkyl-modified deoxyuridine described herein with other deoxynucleotides, a template DNA, and DNA polymerase and allowing the DNA polymerase to incorporate the haloalkyl-modified deoxyuridine described herein and other deoxynucleotides into a newly synthesized labelled nucleic acid. In some embodiments, the DNA synthesis takes place within a cell. In other embodiments, the DNA synthesis takes place within a cell lysate or in vitro system (e.g., haloalkyl-modified deoxyuridine is included in an in vitro DNA synthesis system with the other known components necessary for DNA synthesis).

In some embodiments, because the haloalkyl-modified deoxyuridine is cell permeable, inclusion of the haloalkyl-modified deoxyuridine in growth media will result in haloalkyl-modified deoxyuridine uptake into cells. In such embodiments, cells grown in/on growth media containing haloalkyl-modified deoxyuridine will incorporate haloalkyl-modified deoxyuridine into newly synthesized DNA. In some embodiments, provided herein are methods of modifying a nucleic acid within a cell with a haloalkyl group, the method comprising contacting the cell with a haloalkyl-modified deoxyuridine described herein and allowing the haloalkyl-modified deoxyuridine to enter then cell and be incorporated into the nucleic acid of the cell during DNA synthesis in place of a portion of deoxythmidine nucleotides. In some embodiments, the cell is cultured in media that contains the haloalkyl-modified deoxyuridines.

In some embodiments, provided herein are methods of detecting a nucleic acid within a cell. The cell is contacted by haloalkyl-modified deoxyuridine at a sufficient concentration to allow the haloalkyl-modified deoxyuridines to enter the cell and be incorporated into DNA synthesis in place of a portion of deoxythymidines. In some embodiments, haloalkyl-modified deoxyuridine is included with the cell growth media. The cells are then lysed to produce a cell lysate at a selected point in time. If the haloalkyl-modified deoxyuridine has been incorporated by DNA synthesis into the nucleic acid of the cell, the cell lysate will comprise the haloalkyl-labelled nucleic acid. The cell lysate is then contacted with a binding/detection agent. The binding/detection agent comprises a haloalkyl-binding moiety (e.g., HALOTAG) and a detectable moiety. As described herein, a variety of different detectable moieties find use within embodiments herein. Suitable detectable moieties include fluorophores, fluorescent proteins, luciferases, and components of luminescent complexes. In preferred embodiments, the detectable moiety is a component of a bioluminescent complex. Luminescence is produced in the presence of a substrate for the luminescent complex when binding/detection agents containing the complementary components of the bioluminescent complex bind to the haloalkyl-labeled DNA at nearby locations, thus allowing complementation and formation of the luminescent complex. In some embodiments, components of a bioluminescent complex are selected that do not form a complex in the absence of facilitation by binding partners. In some embodiments, the use of components of a bioluminescent complex as the detectable moieties facilitates detection without a wash step (the unbound binding/detection agents do not produce significant luminescence because they do not form the complex in the absence of facilitation).

In certain embodiments, contacting the cell lysate with a binding/detection agent comprises contacting the cell lysate with: (i) a first fusion of (A) a first modified dehalogenase enzyme capable of covalently binding the haloalkyl group and (B) a peptide component of a luminescent complex; (ii) a second fusion of (A) a second modified dehalogenase enzyme capable of covalently binding the haloalkyl group and (B) a polypeptide component of the luminescent complex; and (iii) a substrate for the luminescent complex. Detection of luminescence indicates binding of the first modified dehalogenase enzyme to haloalkyl groups on the DNA at sufficient enough density to allow formation of the bioluminescent complex. The amount of luminescence is thus proportional to the amount of DNA synthesized in the present of the haloalkyl-modified deoxynucleosides.

In some embodiments, the amount of DNA synthesized is a readout for the amount of cell proliferation. Therefore, in some embodiments, methods are provided for detecting/monitoring the amount of cell proliferation using the systems and methods herein.

In some embodiments, provided herein are methods of detecting a nucleic acid within a cell comprising: (a) expressing within the cell: (i) a first fusion of (A) a first modified dehalogenase enzyme capable of covalently binding the haloalkyl group and (B) a peptide component of a luminescent complex; (ii) a second fusion of (A) a second modified dehalogenase enzyme capable of covalently binding the haloalkyl group and (B) a polypeptide component of the luminescent complex; (b) modifying the nucleic acid with a haloalkyl group by the method herein; (c) contacting the cell with a substrate for the luminescent complex; and (d) detecting luminescence from the luminescent complex, wherein luminescence indicates sufficient density of haloalkyl labeling of the nucleic acid to allow binding of the first fusion and the second fusion at locations along the nucleic that facilitate formation of the luminescent complex.

In some embodiments, provided herein are methods of detecting a nucleic acid within a cell comprising: (a) modifying the nucleic acid with a haloalkyl group by the methods herein; (b) lysing the cell to produce a cell lysate comprising the haloalkyl-modified nucleic acid; (c) contacting the cell lysate with: (i) a fusion of (A) a modified dehalogenase enzyme capable of covalently binding the haloalkyl group and (B) a luminescent protein; and (iii) a substrate for the luminescent complex; and (d) detecting luminescence from the luminescent protein, wherein the luminescence is proportional to the amount of haloalkyl-modified nucleic acid. In some embodiments, when a luminescent protein (e.g., luciferase (e.g., NANOLUC)) is used as the detectable moiety of the fusion, a wash step is required prior to detecting luminescence to ensure that the detected luminescence is that of the DNA-bound luminescent protein. Suitable methods for washing free reagent from DNA are understood in the field.

In some embodiments, provided herein are methods using a tripartite complementation system for detecting a nucleic acid within a cell comprising: (a) modifying the nucleic acid with a haloalkyl group by the methods herein; (b) lysing the cell to produce a cell lysate comprising the haloalkyl-modified nucleic acid; (c) contacting the cell lysate with: (i) a first fusion of (A) a first modified dehalogenase enzyme capable of covalently binding the haloalkyl group and (B) a first peptide component of a luminescent complex; (ii) a second fusion of (A) a second modified dehalogenase enzyme capable of covalently binding the haloalkyl group and (B) a second peptide component of the luminescent complex; (iii) a polypeptide component of the luminescent complex; and (iv) a substrate for the luminescent complex; and (d) detecting luminescence from the luminescent complex, wherein luminescence indicates sufficient density of haloalkyl incorporation into the nucleic acid to allow binding of the first fusion and the second fusion at locations along the nucleic that facilitate formation of the luminescent complex.

In some embodiments, assays are performed to monitor cell proliferation and/or the rate of DNA synthesis in a cell or cells in response to selected environmental conditions or stimuli. For example, the systems and methods herein are used to monitor the rate of DNA synthesis and/or cell proliferation in response to drugs, compounds, external stimuli, etc. In some embodiments, methods herein comprise exposing a cell to a stimulus or condition. In some embodiments, the stimulus or condition is applied before, after, or concurrently with the addition of haloalkyl-modified deoxynucleoside to the cell (or cell media). In some embodiments, a panel of cells are exposed to the stimuli for varying amounts of time before cell lysis, thereby allowing the effect of the stimuli to be observed over time. In some embodiments, the stimuli or condition can be applied to the cells at any step in the methods described herein, for example, prior to addition of haloalkyl-modified deoxynucleoside; after addition of haloalkyl-modified deoxynucleoside, but prior to lysing the cell, etc. In some embodiments, the stimulus results in changes to the rate of cell proliferation/DNA synthesis. In some embodiments, the stimulus results in cell death. In some embodiments, the stimulus results in enhanced cell proliferation.

This invention couples incorporation of novel modified nucleosides with bioluminescence detection. Therefore, it takes advantage of the sensitivity offered by bioluminescent-based detection in a plate-based assay and allows a more user-friendly assay by minimizing sample preparation steps using a NANOBiT "no wash" detection approach.

Without limitation, target cells, the replication and/or DNA synthesis of which is measurable by embodiments herein, can include any cell from any source that is capable of being labeled using the materials and methods provided herein. In some embodiments, a target cell is derived from a patient. In some embodiments, a target cell is of a cell type that is commonly used in cell culture experiments and/or in a clinical setting. In some embodiments, a target cell is derived from a carcinoma, a sarcoma, a leukemia, a lymphoma, a multiple myeloma, a melanoma, a brain or spinal cord tumor, a germ cell tumor, a neuroendocrine tumor, or a carcinoid tumor. In some embodiments, a target cell is any cancerous or non-cancerous primary cell. In some embodiments, a target cell is a stem cell, or a cell derived from a stem cell, from a variety of difference sources, including, but not limited to, bone marrow, embryonic blastocysts or yolk sac, spleen, blood, including peripheral blood and umbilical cord blood, adipose tissue, and other tissues and organs. In some embodiments, a target cell is a hematopoietic stem cell, an endothelial progenitor cell, an embryonic stem cell, or a mesenchymal stem cell.

The cell-permeable haloalkyl-modified nucleosides herein (e.g., haloalkyl-modified deoxyuridine) provide the ability to modify the newly synthesized DNA of a certain cell type of interest, including, but not limited to, primary cells or cells isolated from patient samples without having to genetically engineering the cells. This type of DNA modification allows one to follow the rate of DNA synthesis of the cell population using a sensitive and quantitative bioluminescence approach. The changes can be measured as an end point or in real time using a convenient "add and read" format that is high-throughput and amenable to many different assay platforms.

Embodiments herein are not limited to the HALOTAG, NANOLUC, NANOBiT, NanoTriP, etc., components described herein. Rather, other modified dehalogenases (See, e.g., U.S. Pat. Nos. 7,238,842; 7,425,436; 7,429,472; 7,867,726; each of which is herein incorporated by reference in its entirety)) and complementary detection systems (e.g., other bipartite, tripartite, and multipartite bioluminescent complex systems (See, e.g., U.S. Prov. Appln. Ser. No. 62/684,014; Intl. App. No. PCT/US19/36844; PCT Appln. No. PCT/US14/26354; and/or U.S. Pat. No. 9,797,889; herein incorporated by reference in their entireties) also find use in embodiments herein. Reagents may also include fluorescent proteins or fragments or non-fluorescent subunits of fluorescent proteins that form a fluorescent moiety upon complementation. For example, fluorescent proteins or fragments or non-fluorescent subunits of fluorescent proteins can include those disclosed in Feng et al., (Nature Communications, vol. 8, "Improved split fluorescent proteins for endogenous protein labeling" (2017)), Foglieni et al., (Scientific Reports, vol. 7, "Split GFP technologies to structurally characterize and quantify functional biomolecular interactions of FTD-related proteins" (2017)), and Koraichi et a., (Journal of Cell Science, vol. 131, "High-content tripartite split-GFP cell-based assays to screen for modulators of small GTPase activation" (2018)). For example, in some embodiments, detection agents comprise HALOTAG-fused components of a split fluorescent protein, which is assembled and detected upon binding of the HALOTAG moieties to haloalkyl modified nucleic acid, according to the methods described herein.

As would be recognized by one of ordinary skill in the art based on the present disclosure, the methods and assays herein are capable of detecting any cellular response that leads, either directly or indirectly, to a change in the rate of cellular DNA synthesis. In some embodiments, the cellular response occurs as a result of the cell itself responding to a physiological stimulus. In other embodiments, the cellular response occurs as a result of experimental manipulation (e.g., exposure of the cell to a drug or toxin).

In some embodiments, the methods, assays, materials, and reagents herein find use in assays to determine the effectiveness of a particular treatment or therapy to kill disease cells (e.g., cancer cells, tumor cells, etc.). For example, methods are provided herein for assaying the sensitivity of biopsied tumor cells to chemotherapeutic by monitoring the rate of DNA synthesis of the cells following treatment. Methods are also provided for determining in vitro drug-sensitivity and/or chemosensitivity of a target cell type. In some embodiments, the methods, assays, materials, and reagents herein find use in assays to determine the effect of a particular agent or condition on the rate of DNA synthesis within a cell population.

In some embodiments, the target cells may be of any suitable type that a researcher, clinician, or other user wishes to monitor the death of Cells may be solid tumor cells (e.g., from cell culture, biopsied from a subject, etc.), non-solid cancer cells, non-cancer cells, healthy human cells, cells from a model animal, a cell line, etc.

Embodiments of the present disclosure also include kits comprising the various components described herein. Embodiments of the present disclosure can include a kit comprising a haloalkyl-modified nucleoside (e.g., deoxyuridine) and one or more components of a bioluminescent complex (e.g., each component fused or linked to a modified dehalogenase (e.g., HALOTAG)). In some embodiments, the kit may also include a luminogenic substrate. A kit can include a container and/or instructions. In some embodiments, the kit includes a donor DNA template comprising a sequence encoding a peptide or polypeptide (e.g., HiBiT, LgBiT) or a modified dehalogenase protein (e.g., HALOTAG).

In some embodiments, the kit may include various detection reagents, including, but not limited to, a container comprising a haloalkyl-modified nucleoside (e.g., deoxyuridine), a container comprising a first component of a bioluminescent complex (e.g., fused to HALOTAG), a container comprising a second component of a bioluminescent complex (e.g., fused to HALOTAG), and, in some cases, a container comprising a third component of a bioluminescent complex. In some embodiments, the components of the bioluminescent complex are provided to a single container or separate containers. The kit may also comprise a luminogenic substrate (e.g., NANO-GLO Luciferase Assay Substrate). The kit may also include various buffers and other reagents required to perform a bioluminescence bioassay.

Experiments conducted during development of embodiments herein, as well as previous research on several of the components of the assays, kits, etc. herein demonstrate that the modularity of the various components. For example, the nucleoside (e.g., deoxyuridine) may be attached directly or by a variety of different linkers to various a haloalkyl group that is a suitable substrate for the modified dehalogenase. Similarly, the modified dehalogenase (e.g., HALOTAG or a structurally- or functionally-related dehalogenase) may be fused or tethered any suitable detection reagent (e.g., a bioluminescent polypeptide, a peptide or polypeptide components of a multipartite complementation systems (e.g., bipartite (e.g., NANOBiT), tripartite (e.g., NanoTrip), etc.), a fluorophore, etc.) without altering the function of the modified dehalogenase. The peptide or polypeptide components of a multipartite complementation systems (e.g., bipartite (e.g., NANOBiT), tripartite (e.g., NanoTrip), etc.) can be fused or tethered to various other components, such as a fluorophore, modified dehalogenase (e.g., HALOTAG or a structurally- or functionally-related dehalogenase), etc., while retaining the capacity to form an active bioluminescent complex. In light of the modularity of the components described herein, any combinations of such components (e.g., as fusions, as tethered pairs, in a kit or assay together, etc.) in contemplated and within the scope herein.

In some embodiments, a kit comprises a haloalkyl-modified nucleoside (e.g., deoxyuridine); a modified dehalogenase capable of forming a covalent bond with its substrate (e.g., HALOTAG or a structurally- or functionally-related dehalogenase) fused to a polypeptide component of a bioluminescent complex; and a modified dehalogenase capable of forming a covalent bond with its substrate (e.g., HALOTAG or a structurally- or functionally-related dehalogenase) fused to a peptide component of a bioluminescent complex (e.g., a peptide that exhibits lower affinity for the polypeptide component (e.g., requires facilitation for complex formation); wherein the peptide and polypeptide components form the bioluminescent complex when brought into proper proximity/orientation with one another. In some embodiments, a kit further comprises a substrate for the bioluminescent complex. In some embodiments, an assay is provided that utilizes the aforementioned components.

In some embodiments, a kit comprises a haloalkyl-modified nucleoside (e.g., deoxyuridine); a modified dehalogenase capable of forming a covalent bond with its substrate (e.g., HALOTAG or a structurally- or functionally-related dehalogenase) fused to a polypeptide component of a bioluminescent complex; and fluorophore tethered to a peptide component of a bioluminescent complex (e.g., a peptide that exhibits high affinity for the polypeptide component);

wherein the peptide and polypeptide components form the bioluminescent complex upon co-localization. In some embodiments, a kit further comprises a substrate for the bioluminescent complex. In some embodiments, an assay is provided that utilizes the aforementioned components.

In some embodiments, a kit comprises a haloalkyl-modified nucleoside (e.g., deoxyuridine); a modified dehalogenase capable of forming a covalent bond with its substrate (e.g., HALOTAG or a structurally- or functionally-related dehalogenase) fused to a first peptide component of a bioluminescent complex; a modified dehalogenase capable of forming a covalent bond with its substrate (e.g., HALOTAG or a structurally- or functionally-related dehalogenase) fused to a second peptide component of a bioluminescent complex; and a polypeptide component of the bioluminescent complex; wherein the first peptide, second peptide, and the polypeptide components form the bioluminescent complex when the capture agents bind to capture elements resulting in the peptide components being brought into proper proximity/orientation with one another. In some embodiments, a kit further comprises a substrate for the bioluminescent complex. In some embodiments, an assay is provided that utilizes the aforementioned components.

Other suitable combinations of assay/kit components will be understood by those in the field based upon the disclosure herein.

EXPERIMENTAL

Example 1

Figure 2A:
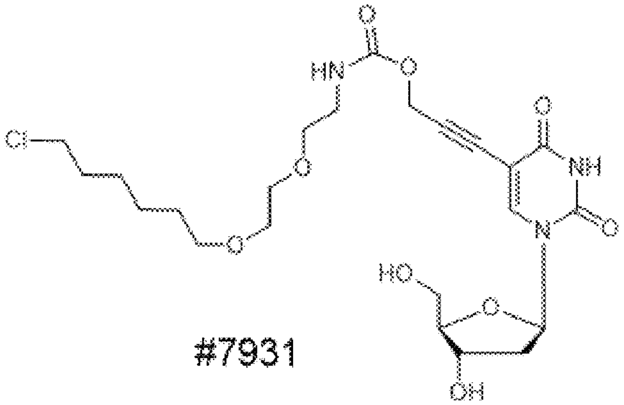
FIG. 2A-B. (A) Molecular structures of PBI-7931 (top) and PBI-7960 (bottom). Luminescence detected following incorporation of haloalkyl-modified nucleosides into newly-synthesized DNA and detection using HALOTAG-NANOBIT fusions.
Figure 2A:
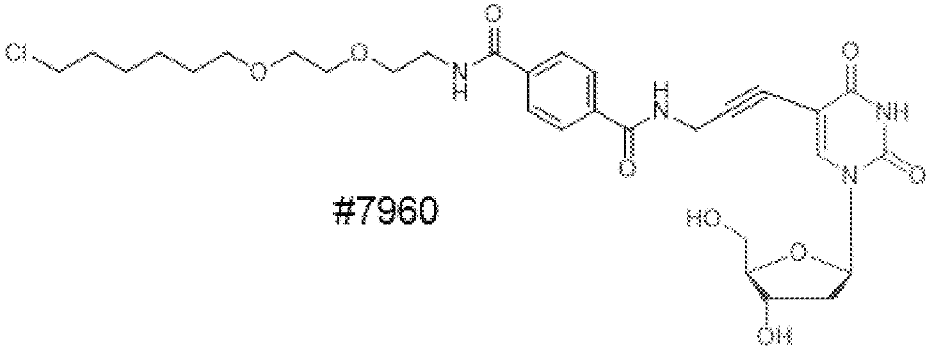
Figure 2B:
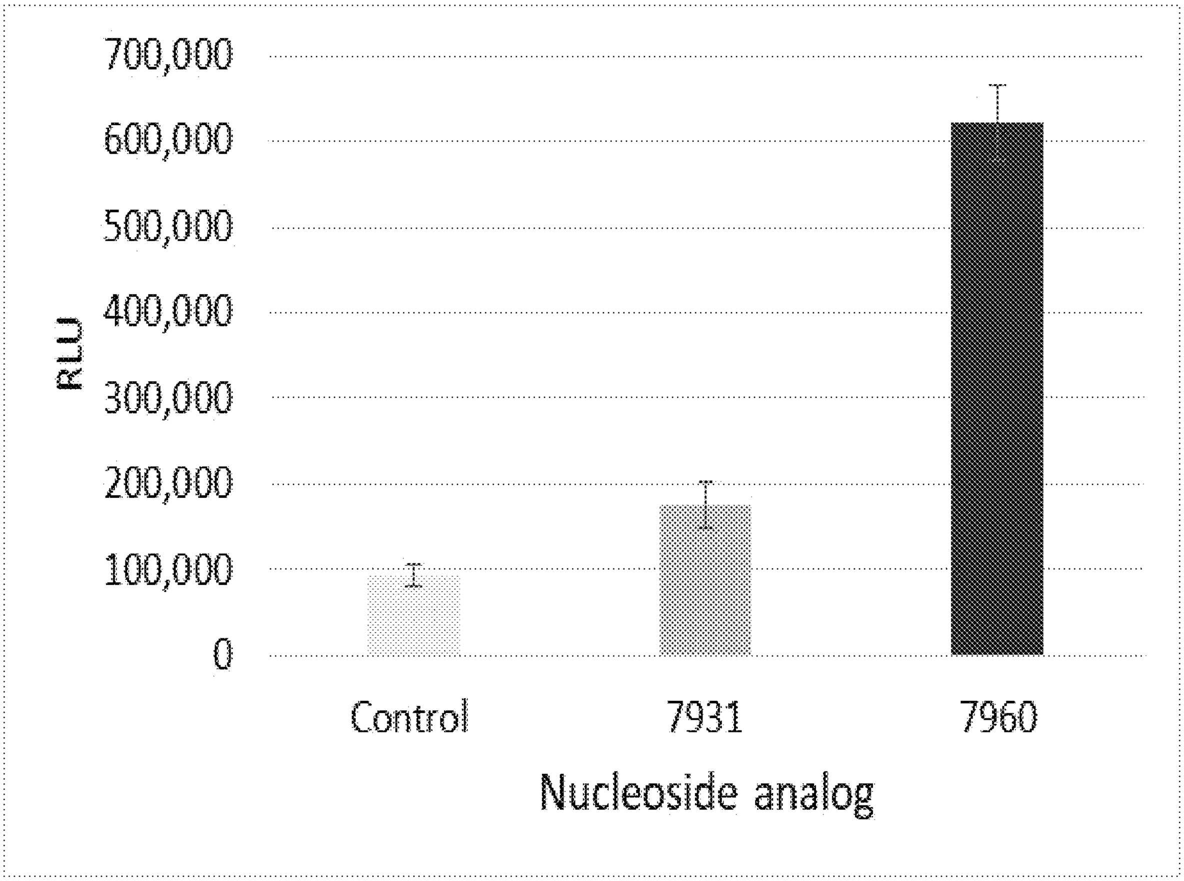

Experiments were conducted during development of embodiments herein to demonstrate the incorporation of modified nucleosides (PBI-7931 and PBI-7960) into newly synthesized DNA and detection using NANOBiT technology. A549 cells plated at 500 cells/well were cultured in medium containing PBI-7931 (FIG. 2A, top) or PBI-7960 (FIG. 2A, bottom) at 10 uM final concentration for 4 hours. Cells without modified nucleosides were used as control. After culturing, the media was removed, cells fixed, permeabilized, and DNA denatured using acid treatment. To measure the number of modified nucleosides incorporated into newly synthesized DNA, HT-LgBiT and HT-SmBiT were added to the cells at 50 nM final concentration. Following a one-hour incubation, NANOLUC substrate was added, and luminescence was measured (FIG. 2B).

Example 2

Figure 3:
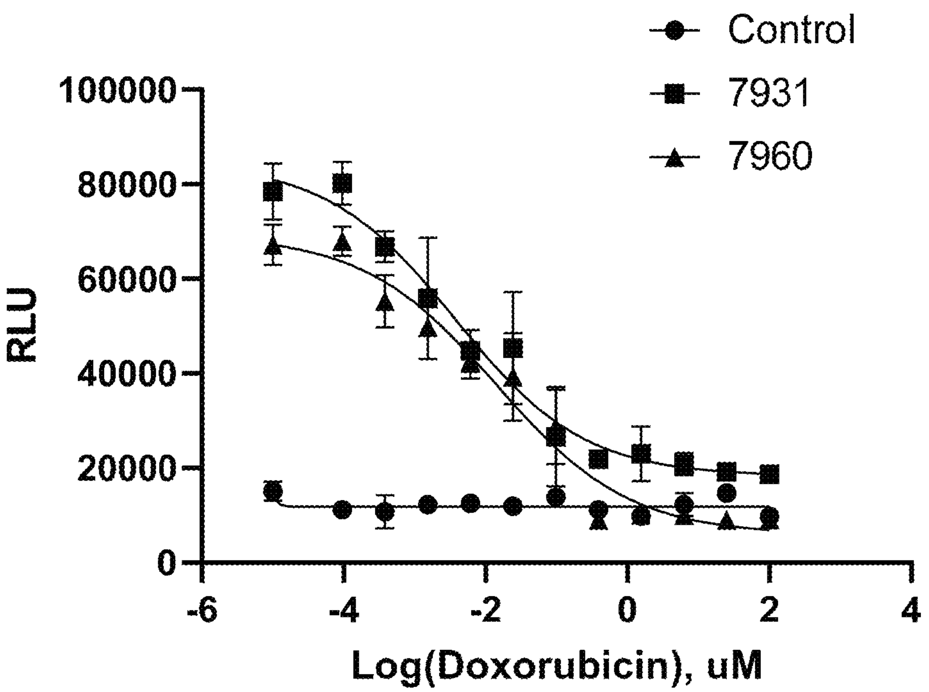
FIG. 3. Inhibition of DNA synthesis by doxorubicin, detected by the reduction in luminescence at increased doxorubicin, following incorporation of haloalkyl-modified nucleosides into newly-synthesized DNA and detection using HALOTAG-NANOBiT fusions.

Experiments were conducted during development of embodiments herein to demonstrate that inhibition of DNA replication can be measured using method described herein. A549 cells plated at 2,000 cells/well were treated with increasing concentrations of the DNA replication inhibitor doxorubicin for 2 hours in a tissue culture incubator. After 2 hours of treatment, compounds PBI-7931 or -7960 were added to the medium at 10 uM final concertation, and the cells placed back into a tissue culture incubator for an additional 4 hours. No compound was added to control cells. To measure the amount of newly synthesized DNA, HT-LgBiT and HT-SmBiT were added to the cells at 50 nM final concentration. Following a one-hour incubation, NANOLUC substrate was added, and luminescence was measured (FIG. 3).

Example 3

Synthesis of compound PBI 7931

Synthesis of Propagyl p-Nitrophenyl Carbonate (mz-1073)

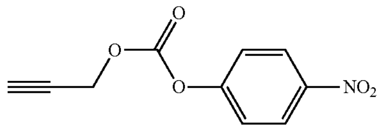 [SMILES: C#CCOC(=O)Oc1ccc([N+](=O)[O-])cc1]

Propagyl alcohol (1 g, 17.8 mmoles) and p-nitrophenyl chloromata (5.39 g, 26.7 mmoles) were mixed in 20 mL of dry THF. The mixture was stirred in an ice-water bath, and Pyridine (4.3 mL, 53.5 mmoles) were added slowly into the reaction mixture. White precipitate formed immediately. After addition, the reaction mixture was kept stirring in the ice-water bath for another 1 hour. The precipitate was removed by centrifuge. The solid was rinsed with 20 mL of acetonitrile and centrifuged again. The liquid portions were combined, concentrated, and purified with flash chromotography (Heptane-Ethyl acetate, 10-50%). About 1.39 g of while solid was obtained (yield 35%).

Synthesis of Propagyl Chloro-PEG2 Carbamate (mz-1074)

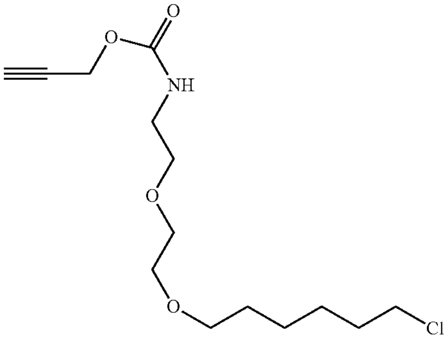 [SMILES: C#CCOC(=O)NCCOCCOCCCCCCCl]

Propagyl p-Nitrophenyl carbonate (111 mg, 0.50 mmoles) and chlorohexyl-PEG2-amine (102 mg, 0.46 mmoles) were mixed in 2 mL of THF, followed with triethylamine (125 µL, 0.91 mmoles). The mixture was stirred at room temperature. After 30 minutes, LC-MS showed product peak with $MS^+$ 306 and 308 (chloro-isotope) (no LC peak). Also, unreacted carbonate was detected. Additional 100 mg of chlorohexyl-PEG2-amine was added. After another 1 hour, no starting material (carbonate) was detected by LC-MS. The mixture was purified with flash chromotography (EtOAc-Heptane, 0-20% in 15 minutes, 20-50% in 1 minute, and product was eluted out at 50% EtOAc. (There is no chromophore in target molecule, so the eluted fractions were detected by UV-Vis for by-product, and light-scattering detector for target molecule). About 110 mg of target molecule (colorless oil, 79% yield) was obtained.

Synthesis of PBI 7931 (mz-1075)

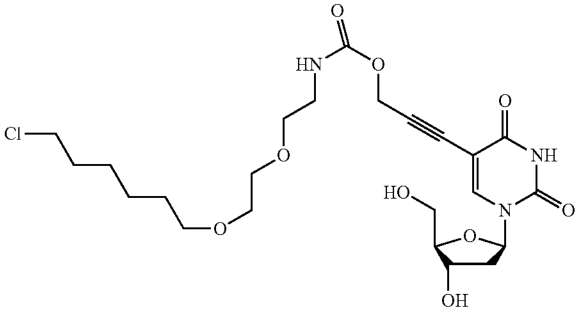

5-Iodo-dU (85 mg, 0.24 mmoles, Chem-impex), Tetrakis (24 mg, 0.024 mmoles) and copper(I) iodide (9.14 mg, 0.048 mmoles) were mixed together in 2.5 mL of DMF in a 100 mL round-bottom flask. The system was vacuumed and refilled with nitrogen twice. A solution of Propagyl Chlorohexyl-PEG2 carbamate (110 mg, 0.36 mmoles) in 2.5 mL of DMF was mixed with 65.6 μL of triethylamine (0.48 mmoles), and the mixture was injected into the reaction flask. The whole clear solution was stirred at 25° C. overnight.

LC-MS showed major peak with $MS^+$ 532, 534 (chloro isotope) at 290 nm. The mixture was purified with prep-HPLC, and about 30 mg of white solid was obtained (yield 23%).

Example 4

Synthesis of compound PBI 7960

4-((2-(2-((6-chlorohexyl)oxy)ethoxy)ethyl)carbamoyl)benzoic acid

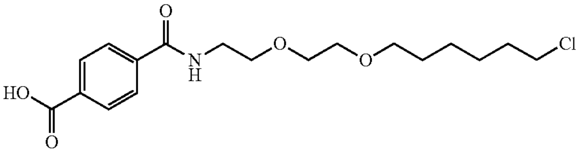 [SMILES: O=C(O)c1ccc(C(=O)NCCOCCOCCCCCCCl)cc1]

To a solution of Terephthalic acid (2.97 g, 17.9 mmol) in anhydrous DMF (40 ml) was added diisopropyl ethylamine (12.5 ml, 71.5 mmol) followed by HATU (Hexafluorophosphate Azabenzotriazole Tetramethyl Uronium, 3.40 g, 8.94 mmol). The solution was stirred for 10 min and 2-(2-((6-chlorohexyl)oxy)ethoxy)ethan-1-amine (2.0 g, 8.94 mmol) was added slowly. The resulting reaction mixture was then stirred overnight. The solution was extracted with ethyl acetate and acetic acid solution (2M) and washed with brine. After dried over sodium sulfate, the organic solvent was evaporated, and the residue was purified by flash chromatography. $^1H$ NMR (400 MHz, $CDCl_3$) δ 8.11 (m, 2H), 7.85 (m, 2H), 6.83 (s, 1H), 3.70-3.59 (m, 8H), 3.52-3.45 (m, 4H), 1.75-1.69 (m, 2H), 1.58-1.54 (m, 2H), 1.43-1.33 (m, 4H); MS m/z 371 [M+H].

2,5-dioxopyrrolidin-1-yl 4-((2-(2-((6-chlorohexyl)oxy)ethoxy)ethyl)carbamoyl)benzoate

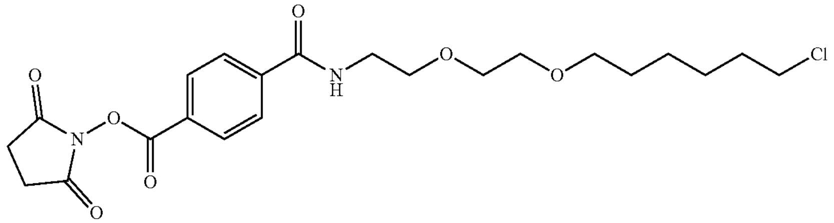 [SMILES: O=C(NCCOCCOCCCCCCCl)c1ccc(C(=O)ON2C(=O)CCC2=O)cc1]

To a solution of 4-((2-(2-((6-chlorohexyl)oxy)ethoxy)ethyl)carbamoyl)benzoic acid (1.02 g, 2.76 mmol) in dichloromethane was added Diisopropyl ethylamine (0.96 ml, 5.51 mmol). TSTU (N,N,N',N'-Tetramethyl-O-(N-succinimidyl)uronium tetrafluoroborate, 0.91 g, 3.03 mmol) was subsequently added and the reaction mixture was stirred for 20 min. The solvent was evaporated, and the residue was purified by flash chromatography. $^1H$ NMR (400 MHz, DMSO) δ 8.84 (t, J=8.0 Hz, 1H), 8.20 (m, 2H), 8.08 (m, 2H), 3.62-3.54 (m, 6H), 3.50-3.43 (m, 4H), 3.38-3.30 (m, 2H), 2.91 (s, 4H), 1.71-1.64 (m, 2H), 1.49-1.42 (m, 2H), 1.39-1.22 (m, 4H); MS m/z 468 [M+H].

N1-(2-(2-((6-chlorohexyl)oxy)ethoxy)ethyl)-N4-(prop-2-yn-1-yl)terephthalamide (HW-0820)

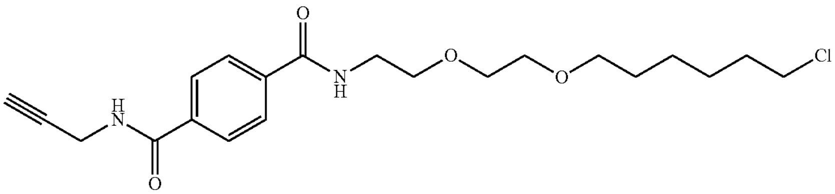 [SMILES: C#CCNC(=O)c1ccc(C(=O)NCCOCCOCCCCCCCl)cc1]

To a solution of 2,5-dioxopyrrolidin-1-yl 4-((2-(2-((6-chlorohexyl)oxy)ethoxy)ethyl)carbamoyl)benzoate (34 mg, 0.073 mmol) in DMF was added propargyl amine (12 mg, 0.22 mmol). The reaction was stirred for two hours, and the solvent was evaporated to dryness. The residue was purified by flash chromatography. MS m/z 409 [M+H].

N1-(2-(2-((6-chlorohexyl)oxy)ethoxy)ethyl)-N4-(3-(1-((2R,4S,5R)-4-hydroxy-5-(hydroxymethyl)tetrahydrofuran-2-yl)-2,4-dioxo-1,2,3,4-tetrahydropyrimidin-5-yl)prop-2-yn-1-yl)terephthalamide (PBI 7960)

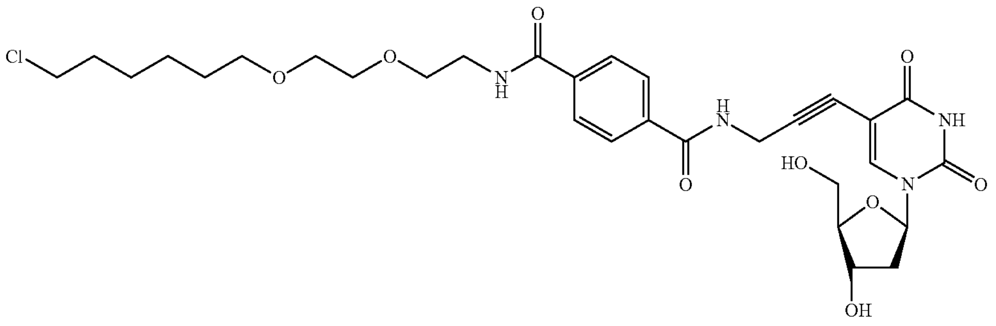

Tetrakis(triphenylphosphine)palladium(0) (6.78 mg, 0.006 mmol), copper(I) iodide (2.24 mg, 0.012 mmol), triethylamine (12 mg, 0.117 mmol), and N1-(2-(2-((6-chlorohexyl)oxy)ethoxy)ethyl)-N4-(prop-2-yn-1-yl)terephthalamide (24 mg, 0.059 mmol) were added to a solution of 5-iodo-2'-deoxycytidine (21 mg, 0.059 mmol) in anhydrous dimethylformamide (5 mL). The orange reaction mixture was stirred at room temperature for 4 h in a nitrogen atmosphere. After that, several drops of 5% of disodium salt of EDTA/H2O were added to the reaction mixture and the contents were concentrated in vacuo. The resulting residue was purified on silica gel column. MS m/z 635 [M+H].

Example 5

Benzamide Linker Synthesis

Compound 1

4-((2-(2-((6-chlorohexyl)oxy)ethoxy)ethyl)carbamoyl)benzoic acid

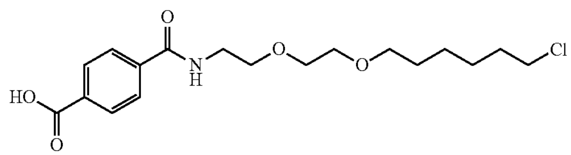 [SMILES: O=C(O)c1ccc(C(=O)NCCOCCOCCCCCCCl)cc1]

Terephthalic acid (3.00 g, 18.06 mmol) and 20 ml of anhydrous DMF were added to a 250 ml round-bottom flask followed by addition of diisopropyl ethylamine (12.58 ml, 72.23 mmol) and HATU (Hexafluorophosphate Azabenzotriazole Tetramethyl Uronium, 3.43 g, 9.03 mmol). The solution was stirred for 10 min before 2-(2-((6-chlorohexyl)oxy)ethoxy)ethan-1-amine (2.02 g, 9.03 mmol) was slowly added. The resulting reaction mixture was sealed with a nitrogen balloon and stirred overnight at room temperature. The solution was extracted with ethyl acetate and acetic acid solution (2M) and washed with brine. After drying over sodium sulfate, the organic solvent was concentrated, and the residue was purified by flash chromatography (10% grade Methanol:DCM). $^1$H NMR (400 MHz, Chloroform-d) δ 8.14-8.03 (m, 2H), 7.88-7.82 (m, 2H), 6.94 (t, J=4.8 Hz, 1H), 3.76-3.68 (m, 5H), 3.62 (dd, J=5.8, 3.0 Hz, 2H), 3.48 (dt, J=13.1, 6.7 Hz, 4H), 2.97 (s, 1H), 2.90 (s, 1H), 1.80-1.67 (m, 2H), 1.57 (p, J=6.9 Hz, 2H), 1.49-1.26 (m, 4H); MS$^+$ 372, 374

Compound 2

2,5-dioxopyrrolidin-1-yl 4-((2-(2-((6-chlorohexyl)oxy)ethoxy)ethyl)carbamoyl)benzoate

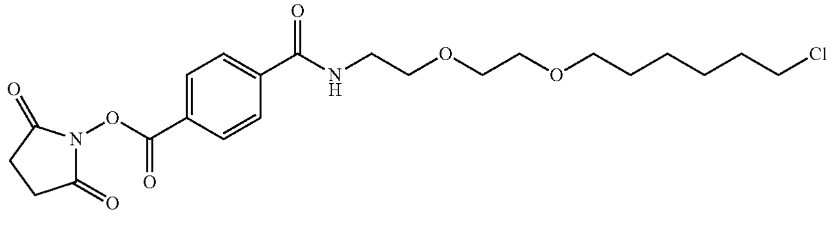 [SMILES: O=C(NCCOCCOCCCCCCCl)c1ccc(C(=O)ON2C(=O)CCC2=O)cc1]

Compound 1 (410 mg, 1.10 mmol) and 5 ml dichloromethane were added to a 250 ml round-bottom followed by addition of diisopropyl ethylamine (0.384 mL, 2.21 mmol) and TSTU (N,N,N',N'-Tetramethyl-O-(N-succinimidyl)uronium tetrafluoroborate, 0.365 g, 1.21 mmol). The reaction mixture was sealed with a nitrogen balloon and stirred for 20 minutes at room temperature. The solvent was concentrated, and the residue was purified by flash chromatography (20% grade Acetone:DCM). $^{1}$H NMR (400 MHz, Chloroform-d) δ 8.20 (d, J=8.2 Hz, 2H), 7.92 (d, J=8.2 Hz, 2H), 6.86 (d, J=5.6 Hz, 1H), 3.72-3.63 (m, 6H), 3.60 (dd, J=5.9, 3.1 Hz, 2H), 3.49 (dt, J=22.1, 6.7 Hz, 4H), 2.92 (s, 3H), 2.17 (s, 1H), 1.74 (p, J=6.8 Hz, 2H), 1.61-1.53 (m, 2H), 1.48-1.27 (m, 4H). MS$^{+}$ 469, 471.

Compound 3

N1-(2-(2-((6-chlorohexyl)oxy)ethoxy)ethyl)-N4-(prop-2-yn-1-yl)terephthalamide

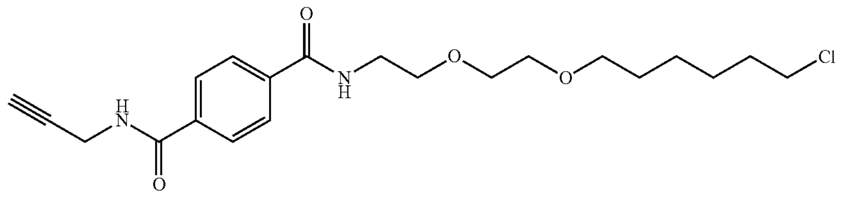 [SMILES: C#CCNC(=O)c1ccc(C(=O)NCCOCCOCCCCCCCl)cc1]

Compound 2 (110 mg, 0.235 mmol) and 4 ml DMF were added to a 250 ml round-bottom flask followed by addition of propargyl amine (38.76 mg, 0.704 mmol). The reaction was sealed with a nitrogen balloon and stirred for 20 minutes at room temperature. The solution was concentrated and purified by flash chromatography (10% grade Methanol: DCM). $^{1}$H NMR (400 MHz, Chloroform-d) δ 7.90-7.80 (m, 4H), 6.87 (d, J=5.7 Hz, 1H), 6.36 (d, J=5.4 Hz, 1H), 4.27 (dd, J=5.2, 2.6 Hz, 2H), 3.73-3.64 (m, 6H), 3.60 (dd, J=5.7, 3.0 Hz, 2H), 3.51 (t, J=6.7 Hz, 2H), 3.46 (t, J=6.7 Hz, 2H), 2.73 (s, 3H), 2.31 (t, J=2.6 Hz, 1H), 1.73 (p, J=6.8 Hz, 4H), 1.56 (p, J=6.9 Hz, 4H), 1.47-1.39 (m, 3H), 1.39-1.35 (m, 2H), 1.35-1.28 (m, 4H), 1.25 (s, 3H), 0.92-0.84 (m, 4H), 0.83 (s, 1H). MS$^{+}$ 409, 411

Compound 4a (PBI-9425)

N1-(3-(4-amino-1-((2R,4S,5R)-4-hydroxy-5-(hydroxymethyl)tetrahydrofuran-2-yl)-2-oxo-1,2,5,6-tetrahydropyrimidin-5-yl)prop-2-yn-1-yl)-N4-(2-(2-((6-chlorohexyl)oxy)ethoxy)ethyl)terephthalamide

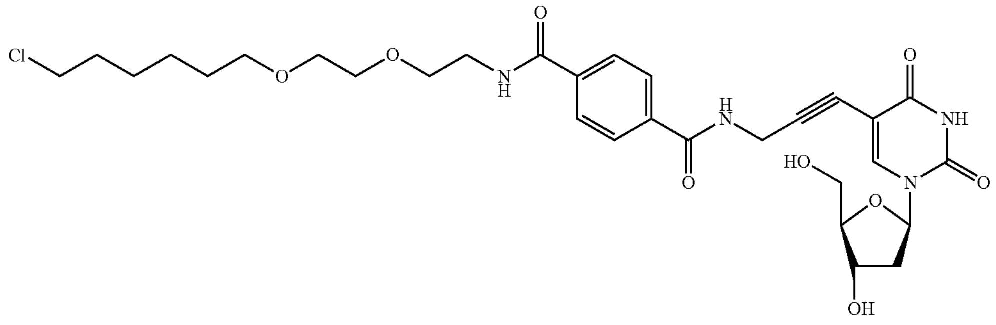

5-Iodo-dC (43.77 mg, 0.123 mmol, Chem-impex), Tetrakis (7.63 mg, 0.007 mmol), and copper(I) iodide (3.37 mg, 0.02 mmol) were mixed in 2.5 mL of DMF in a 100 mL round-bottom flask. The system was vacuumed and refilled with nitrogen twice. In a separate 20 ml vial, Compound 3 (45 mg, 0.11 mmol) in 1.5 mL of DMF were mixed with 244 μL of triethylamine (0.173 mmol), and the mixture was injected into the reaction flask. The clear solution was stirred at room temperature for 2 hours. The mixture was purified with prep-HPLC and concentrated, resulting in about 15 mg of white solid (yield 21.43%, 93.33% purity). $^1$H NMR (400 MHz, Methylene Chloride-$d_2$ & 3 drops of $CD_3OD$) δ 8.47 (s, 1H), 7.89 (d, J=8.0 Hz, 2H), 7.82 (d, J=7.9 Hz, 2H), 6.07 (d, J=6.1 Hz, 1H), 5.32 (s, 9H), 4.41 (d, J=5.4 Hz, 1H), 4.27 (s, 2H), 3.97 (s, 1H), 3.86 (d, J=12.2 Hz, 1H), 3.76 (d, J=12.2 Hz, 1H), 3.68-3.58 (m, 7H), 3.58-3.54 (m, 3H), 3.47 (dtd, J=28.9, 6.7, 2.2 Hz, 5H), 3.35 (s, 1H), 2.45-2.37 (m, 1H), 2.19 (dt, J=13.4, 6.2 Hz, 1H), 1.88 (s, 7H), 1.72 (p, J=7.0 Hz, 3H), 1.52 (s, 2H), 1.34 (ddd, J=37.3, 18.2, 10.4 Hz, 5H); $MS^+$ 634, 636

Compound 4b (PBI-9429)

N1-(3-(2-amino-7-((2S,4R,5S)-4-hydroxy-5-(hydroxymethyl)tetrahydrofuran-2-yl)-4-oxo-4,7-dihydro-1H-pyrrolo[2,3-d]pyrimidin-5-yl)prop-2-yn-1-yl)-N4-(2-(2-((6-chlorohexyl)oxy)ethoxy)ethyl)terephthalamide

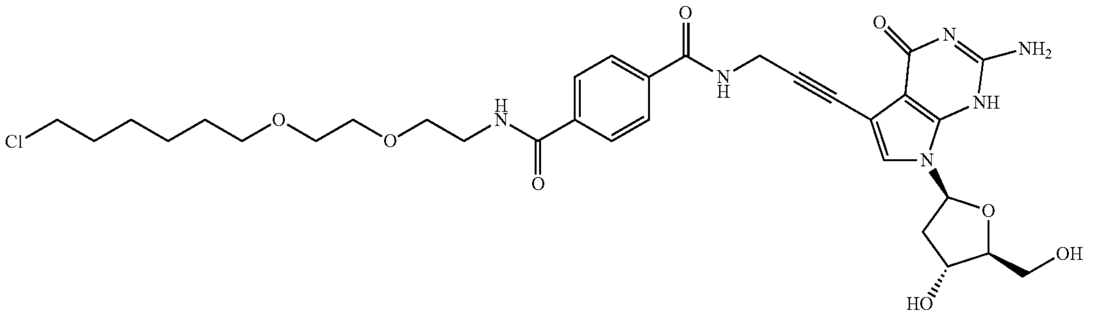 [SMILES: Nc1nc(=O)c2c(C#CCNC(=O)c3ccc(C(=O)NCCOCCOCCCCCCCl)cc3)cn([C@@H]3C[C@@H](O)[C@H](CO)O3)c2[nH]1]

5-Iodo-dG (42.96 mg, 0.110 mmol, Chem-impex), Tetrakis (6.78 mg, 0.006 mmol), and copper(I) iodide (3.35 mg, 0.018 mmol) were mixed in 2.5 mL of DMF in a 100 mL round-bottom flask. The system was vacuumed and refilled with nitrogen twice. In a separate 20 ml vial, Compound 3 (40 mg, 0.098 mmol) in 1.5 mL of DMF was mixed with 30 μL of triethylamine (0.215 mmol), and the mixture was injected into the reaction flask. The clear solution was stirred at room temperature overnight. The mixture was purified with prep-HPLC and concentrated, resulting in about 24 mg of white solid (yield 36.45%, 97.45% purity). $^1$H NMR (400 MHz, Methanol-$d_4$) δ 8.00-7.89 (m, 4H), 7.22 (s, 1H), 6.37 (t, J=7.2 Hz, 1H), 4.46 (dd, J=6.1, 3.1 Hz, 1H), 4.41 (s, 2H), 3.93 (t, J=3.5 Hz, 1H), 3.79-3.72 (m, 1H), 3.67 (td, J=10.5, 8.8, 4.8 Hz, 5H), 3.60 (d, J=5.5 Hz, 4H), 3.50 (dt, J=20.2, 6.9 Hz, 4H), 2.49 (dt, J=14.0, 7.0 Hz, 1H), 2.30-2.21 (m, 1H), 1.72 (p, J=7.0 Hz, 2H), 1.56 (p, J=7.1 Hz, 2H), 1.42 (t, J=7.8 Hz, 2H), 1.34 (dt, J=16.7, 8.8 Hz, 3H); $MS^+$ 634, 636

Compound 4c (PBI-9428)

N1-(3-(4-amino-7-((2S,4R,5S)-4-hydroxy-5-(hydroxymethyl)tetrahydrofuran-2-yl)-7H -pyrrolo[2,3-d]pyrimidin-5-yl)prop-2-yn-1-yl)-N4-(2-(2-((6-chlorohexyl)oxy)ethoxy)ethyl)terephthalamide

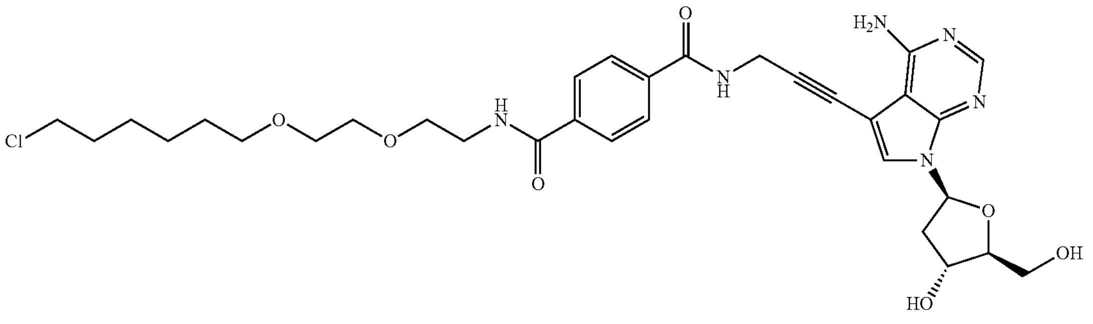 [SMILES: Nc1ncnc2c1c(C#CCNC(=O)c1ccc(C(=O)NCCOCCOCCCCCCCl)cc1)cn2[C@@H]1C[C@@H](O)[C@H](CO)O1]

5-Iodo-dA (41.21 mg, 0.110 mmol, Chem-impex), Tetrakis (6.78 mg, 0.006 mmol), and copper(I) iodide (3.35 mg, 0.018 mmol) were mixed in 2.5 mL of DMF in a 100 mL round-bottom flask. The system was vacuumed and refilled with nitrogen twice. In a separate 20 ml vial, Compound 3 (40 mg, 0.098 mmol) in 1.5 mL of DMF was mixed with 30 μL of triethylamine (0.215 mmol), and the mixture was injected into the reaction flask. The clear solution was stirred at room temperature overnight. The mixture was purified with prep-HPLC and concentrated, resulting in about 10 mg of white solid (yield 15.56%, 99.68% purity). $^1$H NMR (400 MHz, Methanol-$d_4$) δ 8.27 (s, 1H), 8.00-7.88 (m, 5H), 6.62 (t, J=6.5 Hz, 1H), 4.51 (h, J=2.9 Hz, 1H), 4.36 (d, J=2.4 Hz, 2H), 4.01 (p, J=3.3 Hz, 1H), 3.83-3.75 (m, 1H), 3.75-3.67 (m, 2H), 3.67-3.56 (m, 7H), 3.55-3.43 (m, 4H), 2.54 (dt, J=13.9, 6.7 Hz, 1H), 2.40 (ddt, J=13.3, 6.2, 2.8 Hz, 1H), 1.70 (p, J=6.4 Hz, 2H), 1.54 (p, J=6.6 Hz, 2H), 1.37 (dq, J=23.1, 7.5 Hz, 4H); $MS^+$ 657, 659

Example 6

Carbamate Linker Synthesis

Compound 1

4-nitrophenyl prop-2-yn-1-yl carbonate

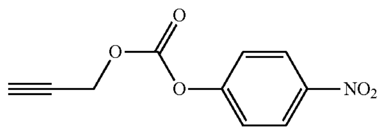 [SMILES: C#CCOC(=O)Oc1ccc([N+](=O)[O-])cc1]

Propargyl alcohol (1 g, 17.8 mmol), p-nitrophenyl chloroformate (5.39 g, 26.8 mmol), and 20 mL of dry THF were added to a 250 ml round-bottom flask and sealed with a nitrogen balloon. The mixture was stirred in an ice-water bath as Pyridine (4.3 mL, 53.5 mmol) was slowly injected into the flask. White precipitate formed immediately. After the Pyridine addition, the mixture was kept stirring in the ice-water bath for another 1 hour. The precipitate was removed by centrifugation, and the resulting solid was rinsed with 20 mL of THF and centrifuged again. The supernatant portions were combined, concentrated, and purified with flash chromatography (50% grade EtOAc:Heptane). $^1$H NMR (400 MHz, Chloroform-d) δ 8.39-8.32 (m, 2H), 8.32-8.25 (m, 10H), 7.54-7.46 (m, 2H), 7.45-7.37 (m, 10H), 4.88 (d, J=2.5 Hz, 10H), 2.62 (t, J=2.5 Hz, 5H), 1.32-1.22 (m, 1H). Not stable in acidic conditions of MS, so only saw $MS^+$ of 138 for phenoxide byproduct.

Compound 2 prop-2-yn-1-yl(2-(2-((6-chlorohexyl)oxy)ethoxy)ethyl)carbamate

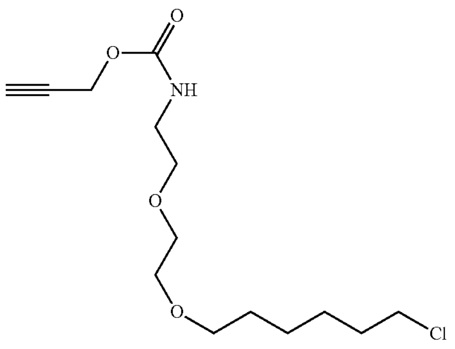 [SMILES: C#CCOC(=O)NCCOCCOCCCCCCCl]

Compound 1 (300 mg, 1.36 mmol), chlorohexyl-PEG2-amine (324.71 mg, 1.25 mmol), and 6 mL of THF were added to a 250 ml round-bottom flask followed by triethylamine (344.1 μL, 2.47 mmol). The mixture was stirred at room temperature for 30 minutes. LC-MS showed product peak with $MS^+$ 306 and 308 (no LC peak) and unreacted carbonate. Additional 300 mg of chlorohexyl-PEG2-amine was added and left stirring overnight. The resulting LCMS showed no starting material (carbonate). The mixture was purified with flash chromatography (40% grade EtOAc: Heptane). There is no chromophore in target molecule, so product was detected by UV-Vis and light-scattering detector. $^1$H NMR (400 MHz, Chloroform-d) δ 5.36 (s, 1H), 4.68 (d, J=2.4 Hz, 3H), 3.65-3.35 (m, 20H), 2.54-2.43 (m, 2H), 1.78 (p, J=6.9 Hz, 3H), 1.62 (d, J=7.2 Hz, 5H), 1.52-1.31 (m, 7H).

Compound 3a (PBI-9391)

3-(4-amino-1-((2R,4S,5R)-4-hydroxy-5-(hydroxymethyl)tetrahydrofuran-2-yl)-2-oxo-1,2-dihydropyrimidin-5-yl)prop-2-yn-1-yl (2-(2-((6-chlorohexyl)oxy)ethoxy)ethyl)carbamate

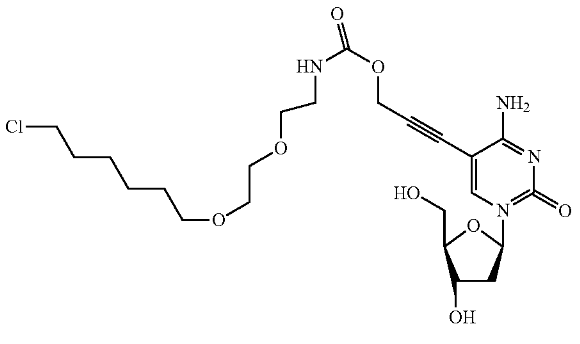

5-Iodo-dC (91.54 mg, 0.403 mmol, Chem-impex), Tetrakis (24.11 mg, 0.021 mmol), and copper(I) iodide (9.18 mg, 0.048 mmol) were mixed in 2.5 mL of DMF in a 100 mL round-bottom flask. The system was vacuumed and refilled with nitrogen twice. In a separate 20 ml vial, Compound 3 (110 mg, 0.36 mmol), 1.5 mL of DMF, and 24 μL of triethylamine (0.173 mmol) were mixed and injected into the reaction flask. The clear solution was stirred at room temperature overnight. The mixture was purified with prep-HPLC and concentrated, resulting in about 44 mg of white solid (yield 23.04%, 85.58% purity). $^1$H NMR (400 MHz, Chloroform-d) δ 8.56 (s, 1H), 6.07 (s, 1H), 6.02-5.97 (m, 1H), 4.81 (s, 2H), 4.49 (s, 1H), 4.00 (dd, J=15.4, 6.1 Hz, 3H), 3.88 (s, 2H), 3.70-3.58 (m, 10H), 3.57 (d, J=5.2 Hz, 10H), 3.49 (dt, J=27.9, 6.7 Hz, 22H), 3.40-3.31 (m, 8H), 3.22 (s, 2H), 3.06 (s, 1H), 2.49 (s, 1H), 2.27 (s, 1H), 1.76 (p, J=6.9 Hz, 8H), 1.59 (t, J=7.3 Hz, 7H), 1.39 (dp, J=28.7, 7.8 Hz, 16H). MS$^+$ 531, 533.

Compound 3b (PBI-9392)

3-(2-amino-7-((2R,4S,5R)-4-hydroxy-5-(hydroxymethyl) tetrahydrofuran-2-yl)-4-oxo-4,7-dihydro-1H-pyrrolo[2,3-d] pyrimidin-5-yl)prop-2-yn-1-yl(2-(2-((6-chlorohexyl)oxy) ethoxy)ethyl)carbamate

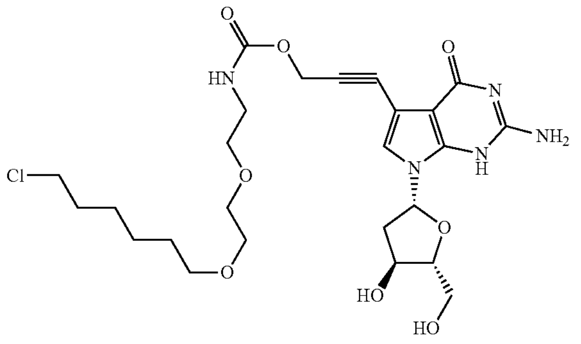 [SMILES: Nc1nc(=O)c2c(C#CCOC(=O)NCCOCCOCCCCCCCl)cn([C@H]3C[C@H](O)[C@@H](CO)O3)c2[nH]1]

5-Iodo-dA (94.04 mg, 0.240 mmol, Chem-impex), Tetrakis (27.71 mg, 0.024 mmol), and copper(I) iodide (9.13 mg, 0.048 mmol) were mixed in 2.5 mL of DMF in a 100 mL round-bottom flask. The system was vacuumed and refilled with nitrogen twice. In a separate 20 ml vial, Compound 3 (110 mg, 0.36 mmol), 1.5 mL of DMF, and 67 μL of triethylamine (0.48 mmol) were mixed and injected into the reaction flask. The clear solution was stirred at room temperature overnight. The mixture was purified with prep-HPLC and concentrated, resulting in about 39 mg of white solid (yield 28.53%, 91.73% purity).$^1$H NMR (400 MHz, Methylene Chloride-$d_2$) δ 10.90 (s, 2H), 7.57 (s, 1H), 6.94 (s, 2H), 5.98 (d, J=8.2 Hz, 2H), 5.32 (s, 16H), 5.03 (d, J=16.0 Hz, 2H), 4.90 (d, J=16.0 Hz, 2H), 4.77 (d, J=5.2 Hz, 2H), 4.10 (s, 2H), 3.91 (d, J=12.1 Hz, 2H), 3.81 (d, J=12.2 Hz, 2H), 3.54 (dq, J=15.6, 8.8, 6.3 Hz, 20H), 3.42 (t, J=6.9 Hz, 7H), 3.37 (s, 3H), 2.96 (s, 1H), 2.21 (d, J=11.1 Hz, 2H), 1.75 (p, J=6.9 Hz, 6H), 1.56 (s, 4H), 1.43 (p, J=7.4 Hz, 6H), 1.34 (q, J=7.8 Hz, 6H), 1.26 (s, 2H), 0.87 (d, J=11.1 Hz, 1H); MS$^+$ 570, 572.

Compound 3c (PBI-9393)

3-(4-amino-7-((2R,4S,5R)-4-hydroxy-5-(hydroxymethyl) tetrahydrofuran-2-yl)-7H-pyrrolo[2,3-d]pyrimidin-5-yl) prop-2-yn-1-yl(2-(2-((6-chlorohexyl)oxy)ethoxy)ethyl)carbamate

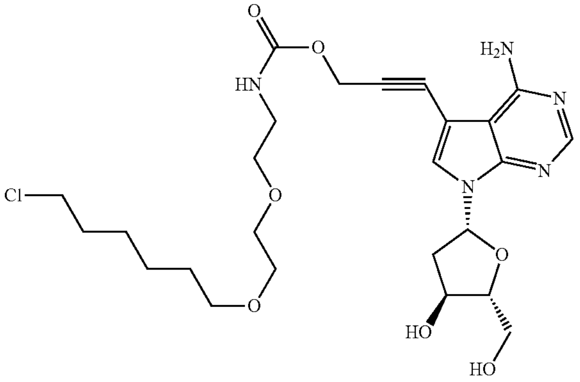 [SMILES: Nc1ncnc2c1c(C#CCOC(=O)NCCOCCOCCCCCCCl)cn2[C@H]1C[C@H](O)[C@@H](CO)O1]

5-Iodo-dG (94.31 mg, 0.240 mmol, Chem-impex), Tetrakis (28.97 mg, 0.025 mmol), and copper(I) iodide (9.55 mg, 0.05 mmol) were mixed in 2.5 mL of DMF in a 100 mL round-bottom flask. The system was vacuumed and refilled with nitrogen twice. In a separate 20 ml vial, Compound 3 (110 mg, 0.36 mmol), 1.5mL of DMF, and 70μL of triethylamine (0.5 mmol) were mixed and injected into the reaction flask. The clear solution was stirred at room temperature overnight. The mixture was purified with prep-HPLC and concentrated, resulting in about 113 mg of white solid (yield 81.35%, 98.23% purity). $^1$H NMR (400 MHz, Chloroform-d) δ 7.83 (s, 1H), 6.99 (s, 1H), 6.20 (t, J=6.9 Hz, 1H), 5.44 (t, J=5.7 Hz, 1H), 4.53 (d, J=2.2 Hz, 2H), 4.42 (dt, J=5.6, 2.7 Hz, 1H), 3.88 (d, J=3.0 Hz, 1H), 3.64 (s, 1H), 3.60-3.52 (m, 1H), 3.38-3.12 (m, 14H), 2.39 (td, J=12.0, 10.5, 5.2 Hz, 1H), 2.16 (ddd, J=13.6, 6.0, 2.7 Hz, 1H), 1.49 (q, J=7.0 Hz, 2H), 1.33 (p, J=6.9 Hz, 2H), 1.14 (dtd, J=27.9, 9.0, 4.8 Hz, 5H); MS$^+$ 554, 556.

Example 7

Figure 4:
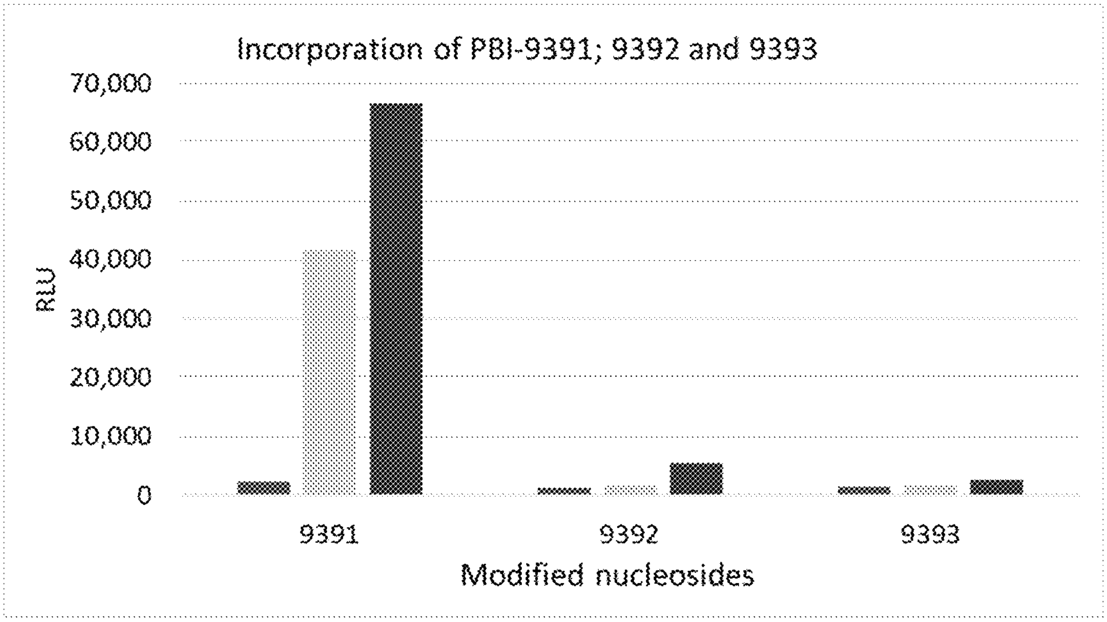
FIG. 4. Modified nucleosides PBI-9391, PBI-9392, and PBI-9393 were incorporated into newly synthesized DNA and detected via NanoBiT.

Experiments were conducted during development of embodiments herein to demonstrate incorporation of modified nucleosides (PBI-9391, PBI-9392, and PBI-9393) into newly synthesized DNA and detection with NanoBiT technology (FIG. 4). A549 cells plated at 5000 cells/well were cultured in medium containing PBI-9391, PBI-9392, or PBI-9393 at 20 uM (light blue bars) or 50 uM (dark blue bars) final concentration for 4.5 hours. Cells without modified nucleosides were used as a control (brown bars). Incorporation of modified nucleosides into DNA was determined by removing the media, fixing and permeabilizing the cells, denaturing DNA, and incubating with HaloTag-LgBiT (HT-LgBiT) and HaloTag-SmBiT (HT-SmBiT) diluted in PBS with 0.01% BSA at 50 nM final concentration. After 2 hours incubation, the reagents were removed, the samples were washed with PBS, NanoLuc substrate was added, and luminescence was measured (FIG. 4).

Example 8

Figure 5:
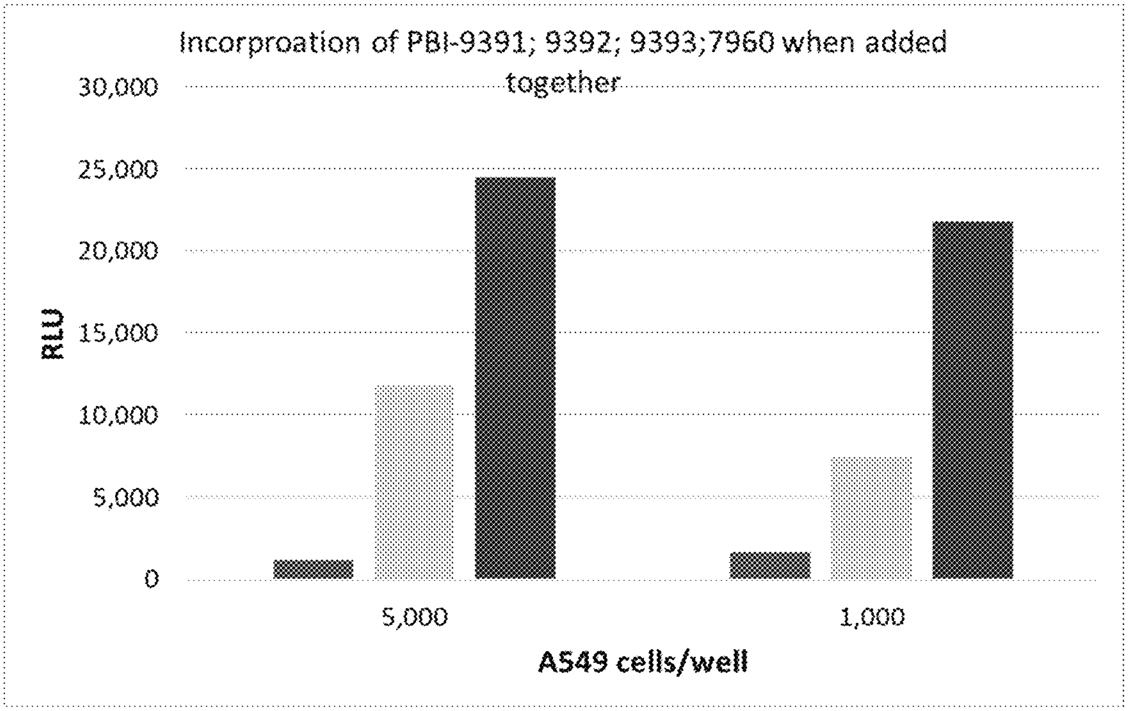
FIG. 5. Modified nucleosides PBI-9391, PBI-9392, PBI-9393, and PBI-7960 were simultaneously incorporated into newly synthesized DNA and detected via NanoBiT. An increase in light output is seen in the presence of the modified nucleosides.

Experiments were conducted during development of embodiments herein to demonstrate incorporation of modified nucleosides (PBI-9391, PBI-9392, PBI-9393, and PBI-7960) into newly synthesized DNA and detection with NanoBiT technology with all the probes added together at final 5 or 12.5 uM each (FIG. 5). The experiment was conducted with A549 cells plated at 5,000 and 1,000 cells per well as described in Example 7. FIG. 5 shows increase in light output in the presence of modified nucleosides added at 5 uM (light blue bars) or 12.5 uM (dark blue bars) as compared to control cells (brown bars).

Example 9

Figure 6:
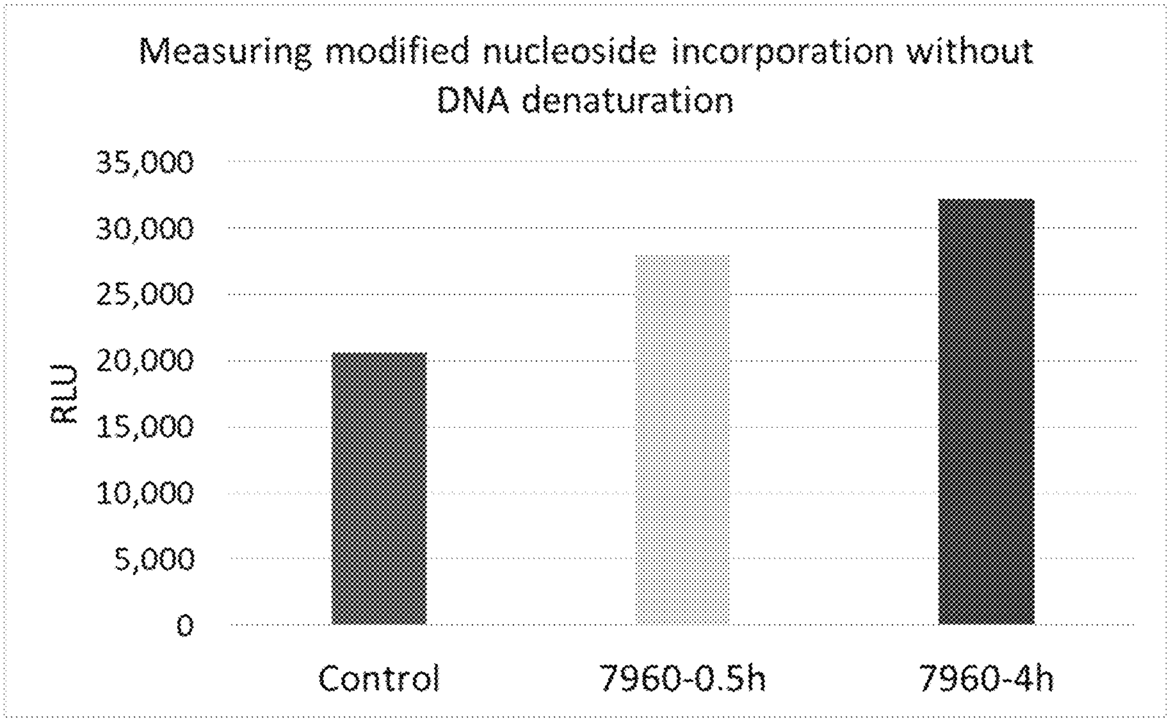
FIG. 6. Incorporation of modified chloroalkane nucleoside PBI-7960 was detected without DNA denaturation.

Experiments were conducted during development of embodiments herein to demonstrate that incorporation of modified chloroalkane nucleosides can be measured without DNA denaturation (FIG. 6). A549 cells plated at 5000 cells/well were cultured in medium containing PBI-7960 at 10 uM final concentration for 0.5 hours (light blue bar) or 4 hours (dark blue bar). Cells without modified nucleosides were used as control (brown bar). Incorporation of modified nucleosides into DNA was determined by removing the media, fixing and permeabilizing the cells and incubating with HT-LgBiT and HT-SmBiT diluted in PBS with 0.01% BSA at 25 nM final concentration. After 1 hour incubation, the NanoLuc substrate was added, and luminescence was measured.

Example 10

Figure 7:
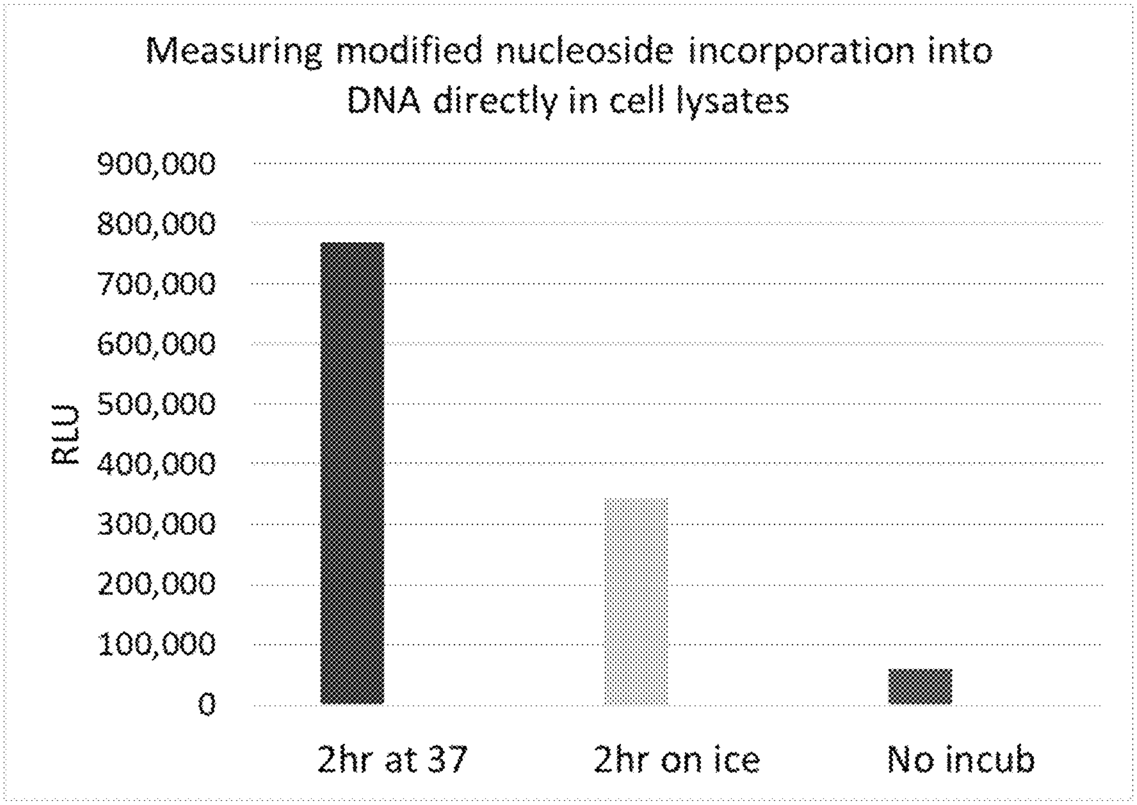
FIG. 7. Incorporation of modified chloroalkane nucleoside PBI-9191 was detected directly in cell lysates using NanoBiT without cell fixing or DNA denaturation.

Experiments were conducted during development of embodiments herein to demonstrate that incorporation of modified chloroalkane nucleosides into newly synthesized DNA can be measured directly in cell lysates (FIG. 7). A549 cells plated at 5,000 cells/well were cultured in medium containing PBI-9191 at 20 uM final concentration for 2 hours at 37° C. (dark blue bar), on ice (light blue bar), or probe was added and immediately removed (brown bar). Incorporation of modified nucleosides into DNA was determined by removing the media, washing the cells with PBS, and lysing in passive lysis buffer (Promega; Cat. No E1941) containing HT-LgBiT and HT-SmBiT at 3.2 nM final concentration. After 1 hour incubation, the NanoLuc substrate was added, and luminescence was measured.

| SEQUENCES |
|---|

WT OgLuc (SEQ ID NO: 1):
MFTLADFVGDWQQTAGYNQDQVLEQGGLSSLFQALGVSVTPIQKVVLSGENGLKADIH
VIIPYEGLSGFQMGLIEMIFKVVYPVDDHHFKIILHYGTLVIDGVTPNMIDYFGRPYPGIA
VFDGKQITVTGTLWNGNKIYDERLINPDGSLLFRVTINGVTGWRLCENILA

WT OgLuc Lg (SEQ ID NO: 2):
MFTLADFVGDWQQTAGYNQDQVLEQGGLSSLFQALGVSVTPIQKVVLSGENGLKADIH
VIIPYEGLSGFQMGLIEMIFKVVYPVDDHHFKIILHYGTLVIDGVTPNMIDYFGRPYPGIA
VFDGKQITVTGTLWNGNKIYDERLINPD

WT OgLuc β9 (SEQ ID NO: 3): GSLLFRVTIN

WT OgLuc β10 (SEQ ID NO: 4): GVTGWRLCENILA

NanoLuc (SEQ ID NO: 5):
MVFTLEDFVGDWRQTAGYNLDQVLEQGGVSSLFQNLGVSVTPIQRIVLSGENGLKIDIH
VIIPYEGLSGDQMGQIEKIFKVVYPVDDHHFKVILHYGTLVIDGVTPNMIDYFGRPYEGIA
VFDGKKITVTGTLWNGNKIIDERLINPDGSLLFRVTINGVTGWRLCERILA NanoLuc Lg (SEQ ID NO: 6):
MVFTLEDFVGDWRQTAGYNLDQVLEQGGVSSLFQNLGVSVTPIQRIVLSGENGLKIDIH
VIIPYEGLSGDQMGQIEKIFKVVYPVDDHHFKVILHYGTLVIDGVTPNMIDYFGRPYEGIA
VFDGKKITVTGTLWNGNKUDERLFNPD NanoLuc β9 (SEQ ID NO: 7): GSLLFRVTINV NanoLuc β10 (SEQ ID NO: 8): GVTGWRLCERILA LgBiT (SEQ ID NO: 9):
MVFTLEDFVGDWRQTAGYNLDQVLEQGGVSSLFQNLGVSVTPIQRIVLSGENGLKIDIH
VIIPYEGLSGDQMGQIEKIFKVVYPVDDHHFKVILHYGTLVIDGVTPNMIDYFGRPYEGIA
VFDGKKITVTGTLWNGNKIIDERLINPDGSLLFRVTIN SmBiT (SEQ ID NO: 10): VTGYRLFEEIL HiBiT (SEQ ID NO: 11): VSGWRLFKKIS LgTrip (3546) (SEQ ID NO: 12):
MKHHHHHHVFTLDDFVGDWEQTAAYNLDQVLEQGGVSSLLQNLAVSVTPIMRIVRSG
ENALKIDIHVIIPYEGLSADQMAQIEEVFKVVYPVDDHHFKVILPYGTLVIDGVTPNKLN
YFGRPYEGIAVFDGKKITTTGTLWNGNKIIDERLITPD SmTrip9 (SEQ ID NO: 13): GSMLFRVTINS β9/β10 dipeptide (SEQ ID NO: 14): GSMLFRVTINSVSGWRLFKKIS SmTrip10 (SEQ ID NO: 15): VSGWRLFKKIS -continued

SEQUENCES

HaloTag (SEQ ID NO: 16):
MAEIGTGFPFDPHYVEVLGERMHYVDVGPRDGTPVLFLHGNPTSSYVWRNIIPHVAPTH
RCIAPDLIGMGKSDKPDLGYFFDDHVRFMDAFIEALGLEEVVLVIHDWGSALGFHWAK
RNPERVKGIAFMEFIRPIPTWDEWPEFARETFQAFRTTDVGRKLIIDQNVFIEGTLPMGVV
RPLTEVEMDHYREPFLNPVDREPLWRFPNELPIAGEPANIVALVEEYMDWLHQSPVPKL
LFWGTPGVLIPPAEAARLAKSLPNCKAVDIGPGLNLLQEDNPDLIGSEIARWLSTLEISG Collective base sequence of bioluminescent complex (SEQ ID NO: 17):
MVFTLDDFVGDWEQTAAYNLDQVLEQGGVSSLLQNLAVSVTPIMRIVRSGENALKIDIH
VIIPYEGLSADQMAQIEEVFKVVYPVDDHHFKVILPYGTLVIDGVTPNKLNYFGRPYEGI
AVFDGKKITTTGTLWNGNKIIDERLITPDGSMLFRVTINSVTGYRLFEEIL WT strand 9-SmBiT (SEQ ID NO: 18): GSMLFRVTINSVTGYRLFEEIL LgTrip 3546 (1-8) (SEQ ID NO: 19):
MVFTLDDFVGDWEQTAAYNLDQVLEQGGVSSLLQNLAVSVTPIMRIVRSGENALKIDIH
VIIPYEGLSADQMAQIEEVFKVVYPVDDHHFKVILPYGTLVIDGVTPNKLNYFGRPYEGI
AVFDGKKITTTGTLWNGNKIIDERLITPD

The invention claimed is:
1. A compound of formula (I):
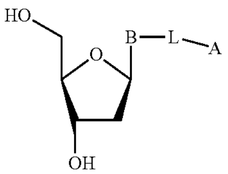
(I)
or a salt thereof, wherein:
B is a nucleobase selected from adenine, guanine, uracil, and cytosine;
L is a linker selected from:
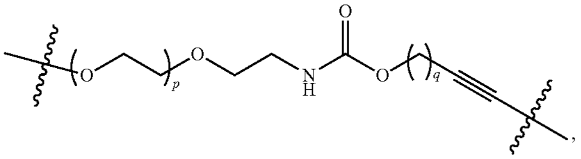
,
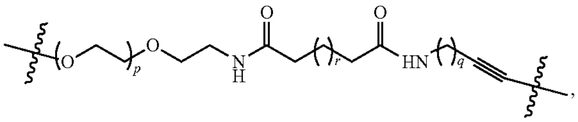
,
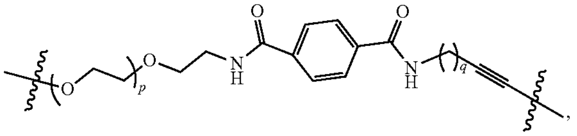
,
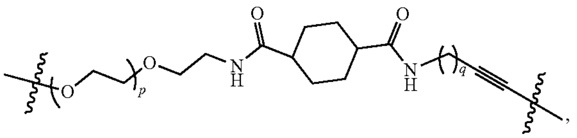
,
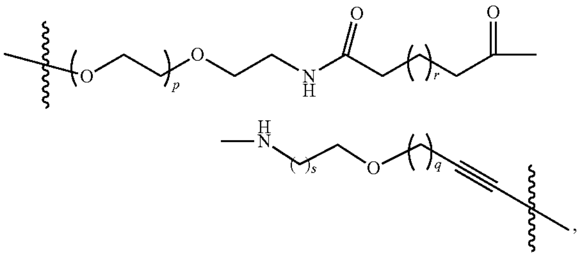
,
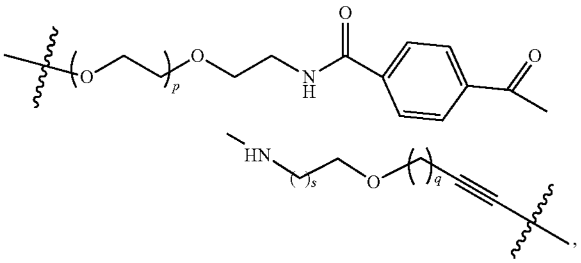
,
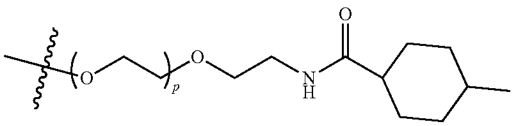
-continued
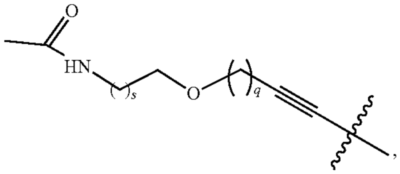
,
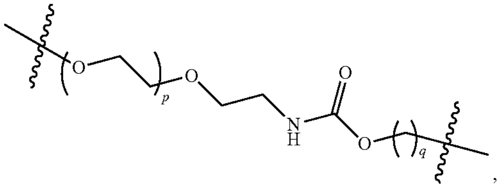
,
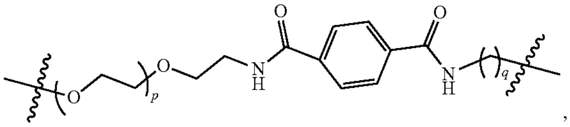
,
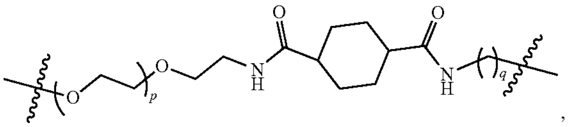
,
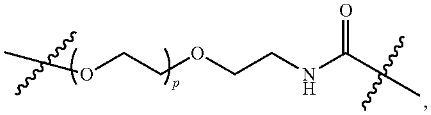
,
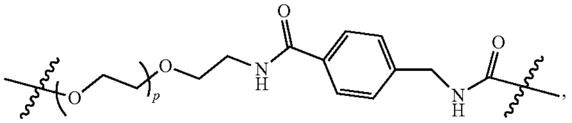
,
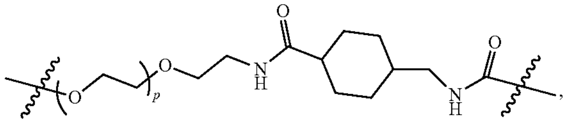
,
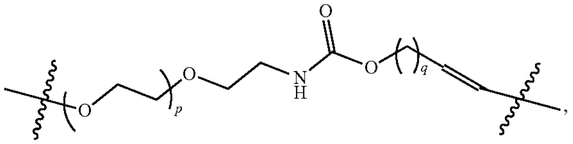
,
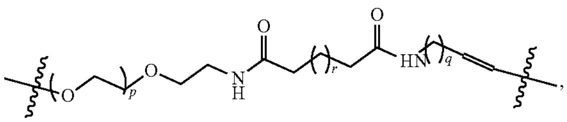
,
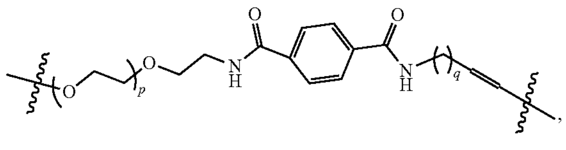
,
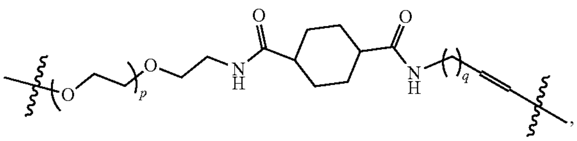
,
wherein p, q, r, and s are each independently 1-6; and
A is a haloalkyl group.

2. The compound of claim 1, or a salt thereof, wherein formula (I) comprises:

(ii)

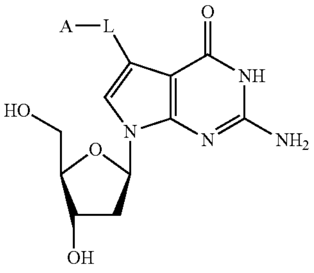

(III)

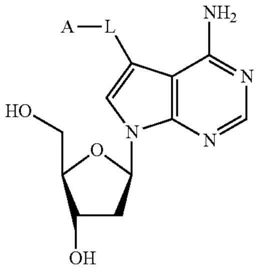

(iv)

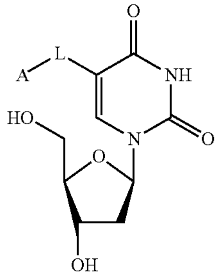

(V)

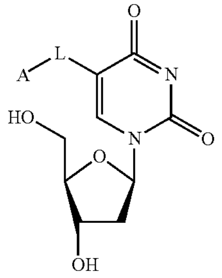

3. The compound of claim 1, or a salt thereof, wherein A is a $C_2$-$C_{12}$ haloalkyl group.

4. A kit comprising:

(a) the compound of claim 1;

(b) a fusion comprising a modified dehalogenase capable of forming a covalent bond with a haloalkyl substrate and a peptide component of a bioluminescent complex;

(c) a fusion comprising a modified dehalogenase capable of forming a covalent bond with a haloalkyl substrate and a polypeptide component of a bioluminescent complex; and (d) a substrate for the bioluminescent complex.

5. A method of incorporating haloalkyl group modified nucleosides into DNA replication within a cell, the method comprising contacting the cell with the compound claim 1, and allowing the compound to enter the cell, allowing the compound to be converted into a modified deoxynucleotide triphosphate by enzymes within a cell, and further allowing the modified deoxynucleotide triphosphate to be incorporated into DNA replication during DNA synthesis.

6. A method of detecting a nucleic acid within a cell comprising:

(a) labeling the nucleic acid with a haloalkyl group by the method of claim 5 Previously presented;

(b) lysing the cell to produce a cell lysate comprising the haloalkyl-labelled nucleic acid;

(c) contacting the cell lysate with:

(i) a first fusion of (A) a first modified dehalogenase enzyme capable of covalently binding the haloalkyl group and (B) a peptide component of a luminescent complex;

(ii) a second fusion of (A) a second modified dehalogenase enzyme capable of covalently binding the haloalkyl group and (B) a polypeptide component of the luminescent complex; and (iii) a substrate for the luminescent complex; and (d) detecting luminescence from the luminescent complex, wherein the luminescent complex produces greater luminescence in the presence of the substrate than the peptide component of polypeptide component alone, and wherein luminescence indicates sufficient density of haloalkyl labeling of the nucleic acid to allow binding of the first fusion and the second fusion at locations along the nucleic that facilitate formation of the luminescent complex.

7. A method of detecting a nucleic acid within a cell comprising:

(a) expressing within the cell:

(i) a first fusion of (A) a first modified dehalogenase enzyme capable of covalently binding the haloalkyl group and (B) a peptide component of a luminescent complex;

(ii) a second fusion of (A) a second modified dehalogenase enzyme capable of covalently binding the haloalkyl group and (B) a polypeptide component of the luminescent complex;

(b) labeling the nucleic acid with a haloalkyl group by the method of claim 5;

(c) contacting the cell with a substrate for the luminescent complex; and (d) detecting luminescence from the luminescent complex, wherein luminescence indicates sufficient density of haloalkyl labeling of the nucleic acid to allow binding of the first fusion and the second fusion at locations along the nucleic that facilitate formation of the luminescent complex.

8. A method of detecting a nucleic acid within a cell comprising:

(a) labeling the nucleic acid with a haloalkyl group by the method of claim 5;

(b) lysing the cell to produce a cell lysate comprising the haloalkyl-labelled nucleic (b) acid;

(c) contacting the cell lysate with:

(i) a fusion of (A) a modified dehalogenase enzyme capable of covalently binding the haloalkyl group and (B) a luminescent protein; and (iii) a substrate for the luminescent protein; and (d) detecting luminescence from the luminescent protein, wherein the luminescence is proportional to the amount of haloalkyl-labeled nucleic acid.

9. A method of detecting a nucleic acid within a cell comprising:
(a) labeling the nucleic acid with a haloalkyl group by the method of claim 5;
(b) lysing the cell to produce a cell lysate comprising the haloalkyl-labelled nucleic acid;
(c) contacting the cell lysate with:
(i) a first fusion of (A) a first modified dehalogenase enzyme capable of covalently binding the haloalkyl group and (B) a first peptide component of a luminescent complex;
(ii) a second fusion of (A) a second modified dehalogenase enzyme capable of covalently binding the haloalkyl group and (B) a second peptide component of the luminescent complex;
(iii) a polypeptide component of the luminescent complex; and
(iv) a substrate for the luminescent complex; and
(d) detecting luminescence from the luminescent complex, wherein luminescence indicates sufficient density of haloalkyl labeling of the nucleic acid to allow binding of the first fusion and the second fusion at locations along the nucleic that facilitate formation of the luminescent complex.

10. A method of incorporating haloalkyl group modified nucleosides into DNA replication within a cell and detecting a resulting haloalkyl-labelled nucleic acid comprising incorporating haloalkyl group modified nucleosides into DNA replication within the cell by the method of claim 5 and further comprising:
(a) lysing the cell to produce a cell lysate comprising the haloalkyl-labelled nucleic acid;
(b) contacting the cell lysate with (i) a modified dehalogenase capable of covalently binding the haloalkyl group and (ii) a reporter capable of producing a detectable signal;
(c) allowing the modified dehalogenase to bind to the haloalkyl groups on the nucleic acid; and
(d) detecting the detectable signal from the reporter.

11. A nucleic acid produced by incorporating haloalkyl group modified nucleosides into DNA replication within a cell, the method comprising contacting the cell with the compound of formula (I):

(I)

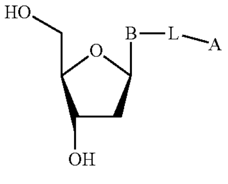

or a salt thereof, wherein:
B is a nucleobase selected from adenine, guanine, uracil, and cytosine;
L is a linker selected from:

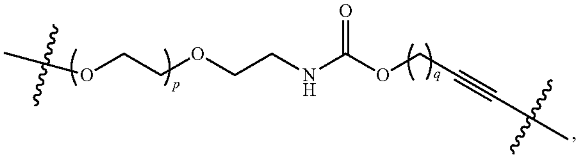
,

-continued

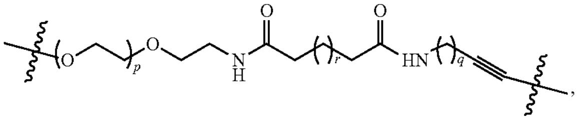
,

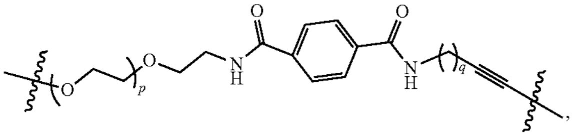
,

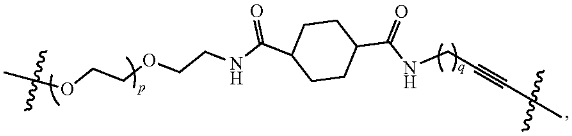
,

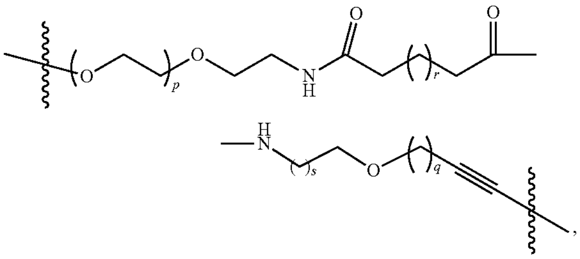
,

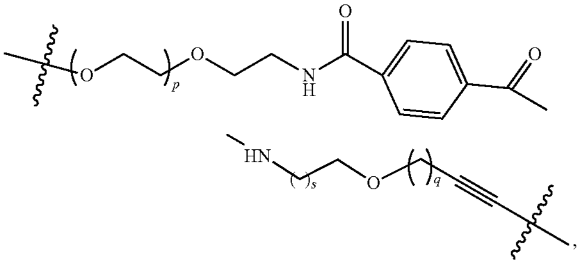
,

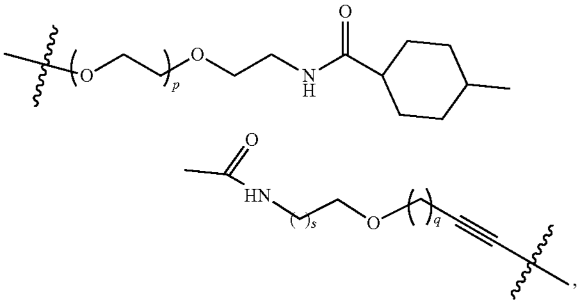
,

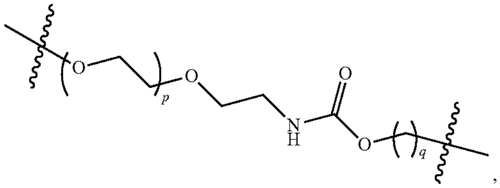
,

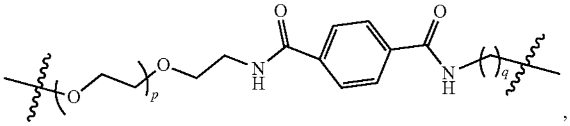
,

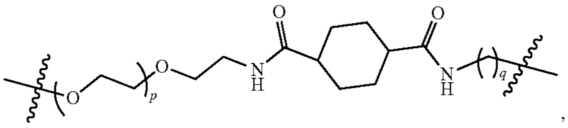
,

-continued

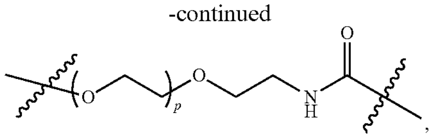,

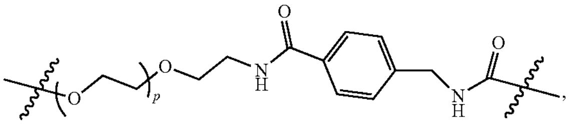,

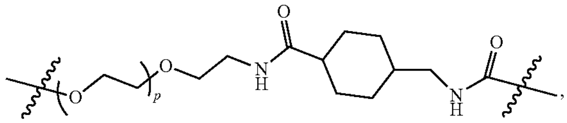,

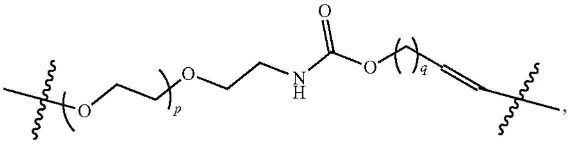,

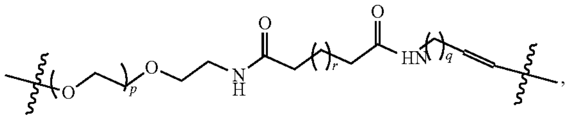,

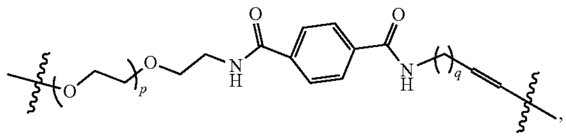,

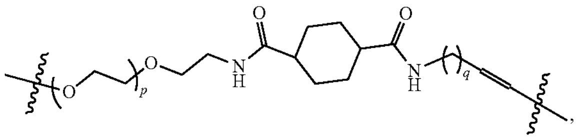, wherein p, q, r, and s are each independently 1-6; and

A is a haloalkyl group;

allowing the compound to enter the cell;

allowing the compound to be converted into a modified deoxynucleotide triphosphate by enzymes within a cell; and further allowing the modified deoxynucleotide triphosphate to be incorporated into DNA replication during DNA synthesis.

12. A cell comprising a nucleic acid of claim 11.

13. A method of detecting haloalkyl-labelled nucleic acid within a cell comprising:

(a) lysing the cell to produce a cell lysate comprising the haloalkyl-labelled nucleic acid;

(b) contacting the cell lysate with (i) a first fusion of (A) a modified dehalogenase capable of covalently binding the haloalkyl group and (B) a first component of a reporter complex, and (ii) a second fusion of (A) a modified dehalogenase capable of covalently binding the haloalkyl group and (B) a second component of a reporter complex, wherein the detectable complex is capable of producing a detectable signal upon the first component being brought in contact or physical proximity with the second component;

(c) allowing the modified dehalogenase to bind to the haloalkyl groups on the nucleic acid; and (d) detecting the detectable signal from the reporter complex.

14. A method of detecting haloalkyl-labelled nucleic acid within a cell comprising:

(a) lysing the cell to produce a cell lysate comprising the haloalkyl-labelled nucleic acid;

(b) contacting the cell lysate with (i) (A) a modified dehalogenase capable of covalently binding the haloalkyl group tethered to (B) a reporter capable of emitting light at a first wavelength, and (ii) (A) a modified dehalogenase capable of covalently binding the haloalkyl group and (B) fluorophore with an excitation spectrum that overlaps the first wavelength and an emission spectrum;

(c) allowing the modified dehalogenase to bind to the haloalkyl groups on the nucleic acid; and (d) detecting a wavelength within the emission spectrum of the fluorophore.

* * * * *